US006927222B2

(12) United States Patent
Hansen et al.

(10) Patent No.: US 6,927,222 B2
(45) Date of Patent: Aug. 9, 2005

(54) COMPOUNDS

(75) Inventors: Peter Hansen, Staffanstorp (SE); Lars Pettersson, Södra Sandby (SE)

(73) Assignee: AstraZeneca AB (SE)

( * ) Notice: Subject to any disclaimer, the term of this patent is extended or adjusted under 35 U.S.C. 154(b) by 6 days.

(21) Appl. No.: 10/204,789

(22) PCT Filed: Feb. 23, 2001

(86) PCT No.: PCT/SE01/00405

§ 371 (c)(1),
(2), (4) Date: Oct. 18, 2002

(87) PCT Pub. No.: WO01/62757

PCT Pub. Date: Aug. 30, 2001

(65) Prior Publication Data

US 2003/0144267 A1 Jul. 31, 2003

(30) Foreign Application Priority Data

Feb. 25, 2000 (SE) ................................................ 0000620
Jun. 14, 2000 (SE) ................................................ 0002234
Oct. 31, 2000 (SE) ................................................ 0003979

(51) Int. Cl.$^7$ .................... A61K 31/437; C07D 471/04; A61P 11/00; A61P 29/00
(52) U.S. Cl. ......................................... 514/292; 546/85
(58) Field of Search .............................. 546/85; 514/292

(56) References Cited

U.S. PATENT DOCUMENTS

| 3,203,992 | A |   | 8/1965  | Kunz et al.         |
|-----------|---|---|---------|---------------------|
| 3,577,432 | A |   | 5/1971  | Helsley             |
| 3,755,584 | A | * | 8/1973  | Plotnikoff ... 514/292 |
| 3,818,017 | A |   | 6/1974  | Janssen et al.      |
| 3,894,030 | A |   | 7/1975  | Janssen et al.      |
| 4,029,801 | A |   | 6/1977  | Cavalla et al.      |
| 4,166,119 | A |   | 8/1979  | Effland et al.      |
| 4,264,613 | A |   | 4/1981  | Regnier et al.      |
| 4,338,323 | A |   | 7/1982  | Regnier et al.      |
| 5,576,321 | A |   | 11/1996 | Krushinski, Jr. et al. |
| 5,614,523 | A |   | 3/1997  | Audia et al.        |
| 5,614,533 | A |   | 3/1997  | Anderson et al.     |
| 5,627,196 | A |   | 5/1997  | Audia et al.        |
| 5,741,789 | A |   | 4/1998  | Hibschman et al.    |
| 5,789,402 | A |   | 8/1998  | Audia et al.        |

FOREIGN PATENT DOCUMENTS

| DE | 37 23 568      | 1/1989  |
|----|----------------|---------|
| DE | 37 23 648      | 1/1989  |
| DE | 197 03 131 A1  | 7/1998  |
| DE | 197 55 268     | 6/1999  |
| EP | 0 095 454 A2   | 11/1983 |
| EP | 0 128 007 A2   | 12/1984 |
| EP | 0 496 691 A1   | 7/1992  |
| EP | 0 587 311 A1   | 3/1994  |
| EP | 0 722 941 A2   | 7/1996  |
| EP | 0 0903 349 A2  | 3/1999  |
| FR | 2 190 430      | 2/1974  |
| GB | 1368012        | 9/1974  |
| WO | WO 93/25528    | 12/1993 |
| WO | WO 97/23458    | 7/1997  |
| WO | WO 98/32442    | 7/1998  |
| WO | WO 99/25686    | 5/1999  |
| WO | WO 99/31092    | 6/1999  |
| WO | WO 99/65895    | 12/1999 |
| WO | WO 00/35449    | 6/2000  |
| WO | WO 00/35451    | 6/2000  |
| WO | WO 00/53600    | 9/2000  |
| WO | WO 00/58305    | 10/2000 |
| WO | WO 00/69850    | 11/2000 |
| WO | WO 01/14333 A1 | 3/2001  |
| WO | WO 01/43744    | 6/2001  |
| WO | WO 01/44227    | 6/2001  |
| WO | WO 01/87839 A1 | 11/2001 |

OTHER PUBLICATIONS

Howard OMZ et al. (1996) TIBTECH. 14, 46–51.*
Hesselgesser J et al. (1998) J. Biol. Chem. 273(25), 15687–15692.*
Marc Payard, et al., "Dérivés N aminométhyles de quelques acides hydroxamiques à visée anti–inflammatoire," Eur. J. Med. Chem., vol. 10, No. 2, pp. 125–128 (Mar.–Apr. 1975).
Frank Navas III, et al., "The Design and Synthesis of a Hapten for 1192U90, A Potential Atypical Antipsychotic Agent," Synthetic Communications, vol. 26, No. 7, pp. 1411–1421 (1996).
Jon L. Wright et al., "Discovery of Selective Dopamine D4 Receptor Antagonists: 1–Aryloxy–3–(4–Aryloxypiperidinyl)–2–Propanols", vol. 7, No. 11, Bioorganic & Medicinal Chemistry Letters, 1377–1380 (1997).
Cattanach et al., "Studies in the Indole Series . . . ", 1968, J. Chem. Soc.;1235–1243.
STN International, File CAPLUS, CAPLUS Accession No. 1968.402884.
O.M. Zack Howard, et al., "Chemokines: progress toward identifying molecular targets for therapeutic agents," Trends in Biotechnology, vol. 14, pp. 46–51 (1996).
Joseph Hesselgesser, et al., "Identification and Characterization of Small Molecule Functional Antagonists of the CCR1 Chemokine Receptor," The Journal of Biological Chemistry, vol. 273, No. 25, pp. 15687–15692 (1998).
Marc Payard, et al., "N–Aminomethylated Derivatives of Some Hydroxamic Acids as Anti–Inflammatories," Eur. J. Med. Chem., pp. 1–10 (Jan. 21, 1975).
J. Chem. Soc. C., vol. 10, 1968, Cattanach, Christopher J. et al., "Indole Series. IV. Tetrahydro–5H–pyrido[4, 3–b] indoles as serotonin antagonists" p. 1235–1243.

(Continued)

Primary Examiner—Evelyn Mei Huang
(74) Attorney, Agent, or Firm—Fish & Richardson P.C.

(57) ABSTRACT

The invention provides compounds of general formula (I) wherein Q, R, $R^1$, $R^2$, $R^3$, $R^4$, $R^5$, $R^6$, $R^7$ and $R^8$ are as defined in the specification, processes for their preparation, pharmaceutical compositions containing them and their use in therapy.

12 Claims, No Drawings

OTHER PUBLICATIONS

U.S. Appl. No. 10/311,667, filed Dec. 17, 2002, Eriksson et al.
U.S. Appl. No. 10/468,179, filed Aug. 18, 2003, Brough et al.
U.S. Appl. No. 10/472,412, filed Sep. 16, 2003, Eriksson et al.
Archibald et al., "Antiinflammatory 4–acylaminopiperidines", *CAPLUS* 77:34355 (1972).
Cohen et al., "Cytokine function: A study in biologic diversity", *CAPLUS* 125:31527 (1996).
Friebe et al., "Piperidinopropyl derivatives and pharmaceutical compositions containing them", *CAPLUS* 94:103172 (1981).
Leclerc et al., "Derivatives Related to Betaxolol with α–and β–Adrenergic Activities", *Arzneim.–Forsch/Drug. Res.* 35(11):1357–1367 (1985).
Rubini et al., "Synthesis of Isosteric Methylene–Oxy Pseudodipeptide Analogues as Novel Amide Bond Surrogate Units", *Tetrahedron* 42(21):6039–6045 (1986).
Timmermans et al., "Hypotensive Properties of Benzodioxane Derivatives Structurally Related to R28935. Comparison of Activity with some Receptor Affinities", *Arch. int. Pharmacodyn.* 255:321–334 (1982).
Tomoaki Komai, et al., "Structure–Activity Relationships of HIV–1 PR Inhibitors Containing AHPBA–II. Modification of Pyrrolidine Ring at P1' Proline," Bioorganic & Medicinal Chemistry, vol. 4, No. 8, pp. 1365–1933 (1996).
Manabu Hori Kim D. Janda, "A Soluble Polymer Approach to the "Fishing Out" Principle: Synthesis and Purification of β–Amino Alcohols," J. Org. Chem, vol. 63, pp. 889–894 (1998).
Meurer et al., "Discovery of potent human CCR5 antagonists for the treatment of HIV–1 infection—II.", *CAPLUS* 2000:331722 (2000).
U.S. Appl. No. 10/204,754, filed Aug. 23, 2002, Hansen et al.
U.S. Appl. No. 10/204,790, filed Aug. 23, 2002, Bodkin et al.
U.S. Appl. No. 10/311,667, filed Dec. 17, 2002, Eriksson et al.
U.S. Appl. No. 10/311,841, filed Dec. 17, 2002, Eriksson et al.
U.S. Appl. No. 10/468,179, filed Aug. 18, 2003, Brough et al.
U.S. Appl. No. 10/472,017, filed Sep. 19, 2003, Eriksson et al.
U.S. Appl. No. 10/472,412, filed Sep. 16, 2003, Eriksson et al.
U.S. Appl. No. 10/204,789, filed Jul. 31, 2002, Hansen et al.
U.S. Appl. No. 10/471,499, filed Sep. 11, 2003, Brough et al.

* cited by examiner

COMPOUNDS

CROSS REFERENCE TO RELATED APPLICATIONS

The present application is a national phase application under 35 U.S.C. Section 371 filed from International Patent Application PCT/SE01/00405, filed 23 Feb. 2001, which claims priority to Swedish patent application Serial. No. 0000620-5, filed 25 Feb. 2000, Swedish patent application Serial. No. 0002234-3, filed 14 Jun. 2000, and Swedish patent application Serial. No. 0003979-2, filed 31 Oct. 2000. The contents of these applications, are incorporated herein by reference in their entirety.

The present invention relates to novel compounds, processes for their preparation, pharmaceutical compositions containing them and their use in therapy.

U.S. Pat. No. 5,789,402 describes certain indole derivatives which are said to be useful for the treatment of diseases which are caused or affected by disorders of the serotonin-affected neurological systems, particularly those relating to the serotonin $1_A$ receptor and those relating to the uptake of serotonin.

Chemokines play an important role in immune and inflammatory responses in various diseases and disorders, including asthma and allergic diseases, as well as autoimmune pathologies such as rheumatoid arthritis and atherosclerosis. These small secreted molecules are a growing superfamily of 8–14 kDa proteins characterised by a conserved is four cysteine motif. The chemokine superfamily can be divided into two main groups exhibiting characteristic structural motifs, the Cys-X-Cys (C-X-C) and Cys-Cys (C-C) families. These are distinguished on the basis of a single amino acid insertion between the NH-proximal pair of cysteine residues and sequence similarity.

The C-X-C chemokines include several potent chemoattractants and activators of neutrophils such as interleukin-8 (IL-8) and neutrophil-activating peptide 2 (NAP-2).

The C-C chemokines include potent chemoattractants of monocytes and lymphocytes but not neutrophils such as human monocyte chemotactic proteins 1–3 (MCP-1, MCP-2 and MCP-3), RANTES (Regulated on Activation, Normal T Expressed and Secreted), eotaxin and the macrophage inflammatory proteins 1α and 1β (MIP-1α and MIP-1β).

Studies have demonstrated that the actions of the chemokines are mediated by subfamilies of G protein-coupled receptors, among which are the receptors designated CCR1, CCR2, CCR2A, CCR2B, CCR3, CCR4, CCR5, CCR6, CCR7, CCR8, CCR9, CCR10, CXCR1, CXCR2, CXCR3 and CXCR4. These receptors represent good targets for drug development since agents which modulate these receptors would be useful in the treatment of disorders and diseases such as those previously mentioned.

In accordance with the present invention, there is therefore provided a compound of general formula:

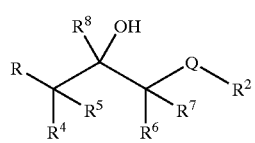

(I)

wherein,

R represents either a group:

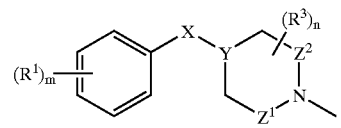

or a group:

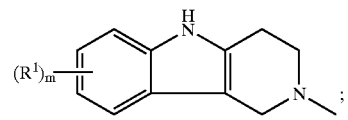

m is 0, 1, 2 or 3;

each $R^1$ independently represents halogen, cyano, nitro, carboxyl, hydroxyl, $C_3$–$C_6$ cycloalkyl, $C_1$–$C_6$ alkoxy, $C_1$–$C_6$ alkoxycarbonyl, $C_1$–$C_6$ haloalkyl, $C_1$–$C_6$ haloalkoxy, —$NR^9R^{10}$, $C_3$–$C_6$ cycloalkylamino, $C_1$–$C_6$ alkylthio, $C_1$–$C_6$ alkylcarbonyl, $C_1$–$C_6$ alkylcarbonylamino, sulphonamido (—$SO_2NH_2$), $C_1$–$C_6$ alkylsulphonyl, —$C(O)NR^{11}R^{12}$, —$NR^3C(O)$—$(NH)_pR^{14}$, phenyl, or $C_1$–$C_6$ alkyl optionally substituted by carboxyl or $C_1$–$C_6$ alkoxycarbonyl;

p is 0 or 1;

X represents an oxygen or sulphur atom or a $CH_2$, $CH(CH_3)$, $OCH_2$, $CH_2O$, $CH_2NH$, NH or carbonyl group and Y represents a nitrogen atom or a CH or C(OH) group, provided that when X represents an oxygen or sulphur atom or a $CH_2O$, $CH_2NH$ or NH group, then Y represents a CH group;

$Z^1$ represents a bond or a group $(CH_2)_q$ where q is 1 or 2;

$Z^2$ represents a bond or a group $CH_2$, with the proviso that $Z^1$ and $Z^2$ do not both simultaneously represent a bond;

Q represents an oxygen or sulphur atom or a group $CH_2$ or NH;

$R^2$ represents a group:

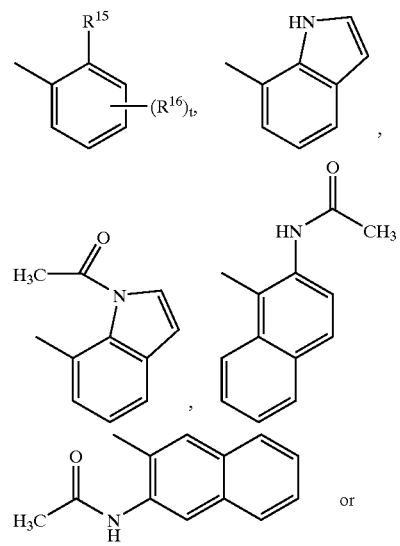

or

-continued

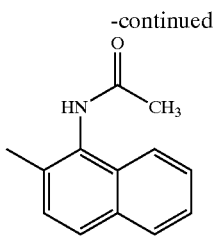

n is 0, 1 or 2;

each $R^3$ independently represents a $C_1$–$C_6$ alkyl, $C_1$–$C_6$ alkoxycarbonyl, —$CH_2OH$ or carboxyl group;

$R^4$, $R^5$, $R^6$ and $R^7$ each independently represent a hydrogen atom or a $C_1$–$C_6$ alkyl group, or $R^4$, $R^5$, $R^6$ and $R^7$ together represent a $C_1$–$C_4$ alkylene chain linking the two carbon atoms to which they are attached to form a 4- to 7-membered saturated carbocycle, or $R^5$, $R^6$ and $R^7$ each represent a hydrogen atom and $R^4$ and $R^8$ together with the carbon atoms to which they are attached form a 5- to 6-membered saturated carbocycle;

$R^8$ represents a hydrogen atom, a $C_1$–$C_6$ alkyl group or is linked to $R^4$ as defined above;

$R^9$ and $R^{10}$ each independently represent a hydrogen atom or a $C_1$–$C_6$ alkyl group, or $R^9$ and $R^{10}$ together with the nitrogen atom to which they are attached form a 4- to 7-membered saturated heterocycle;

$R^{11}$ and $R^{12}$ each independently represent a hydrogen atom or a $C_1$–$C_6$ alkyl group optionally substituted by $C_1$–$C_6$ alkoxycarbonyl;

$R^{13}$ represents a hydrogen atom or a $C_1$–$C_6$ alkyl group;

$R^{14}$ represents a hydrogen atom, or a $C_1$–$C_6$ alkyl group optionally substituted by carboxyl, $C_1$–$C_6$ alkoxy or $C_1$–$C_6$ alkoxycarbonyl;

$R^{15}$ represents carboxyl, $C_1$–$C_6$ alkylcarbonyl, $C_1$–$C_6$ alkoxycarbonyl, $C_1$–$C_6$ alkoxycarbonyl$C_1$–$C_6$ alkyl or a group —$NR^{17}R^{18}$, —$NHSO_2CH_3$, —$NHC(O)CH_3$, —$C(O)NR^{17}R^{18}$, —$NHC(O)NR^{17}R^{18}$, —$OC(O)NR^{17}R^{18}$, —$OCH_2C(O)NR^{17}R^{18}$, —$NHC(O)OR^{17'}$ or —$OR^{17''}$;

t is 0, 1, 2 or 3;

each $R^{16}$ independently represents halogen, cyano, nitro, carboxyl, hydroxyl, $C_3$–$C_6$ cycloalkyl, $C_1$–$C_6$ alkoxy, $C_1$–$C_6$ alkoxycarbonyl, $C_1$–$C_6$ haloalkyl, $C_1$–$C_6$ haloalkoxy, —$NR^{19}R^{20}$, $C_3$–$C_6$ cycloalkylamino, $C_1$–$C_6$ alkylthio, $C_1$–$C_6$ alkylcarbonyl, $C_1$–$C_6$ alkylcarbonylamino, sulphonamido (—$SO_2NH_2$), $C_1$–$C_6$ alkylsulphonyl, —$C(O)NR^{21}R^{22}$, —$NR^{23}C(O)(NH)_vR^{24}$, phenyl, or $C_1$–$C_6$ alkyl optionally substituted by carboxyl or $C_1$–$C_6$ alkoxycarbonyl;

$R^{17}$ and $R^{18}$ each independently represent (i) a hydrogen atom, (ii) a 5- to 6-membered saturated or unsaturated ring which may comprise at least one heteroatom chosen from nitrogen, oxygen and sulphur, the ring being optionally substituted with at least one substituent selected from halogen, methyl and trifluoromethyl, or (iii) a $C_1$–$C_6$ alkyl group optionally substituted by at least one substituent selected from halogen, trifluoromethyl, carboxyl, $C_1$–$C_6$ alkoxycarbonyl and, a 5- to 6-membered saturated or unsaturated ring which may comprise at least one heteroatom chosen from nitrogen, oxygen and sulphur, the ring being optionally substituted with at least one substituent selected from halogen, methyl and trifluoromethyl, or $R^{17}$ and $R^{18}$ together with the nitrogen atom to which they are attached form a 4- to 7-membered saturated heterocycle;

$R^{17'}$ represents a hydrogen atom, or a $C_1$–$C_6$ alkyl group optionally substituted by carboxyl or $C_1$–$C_6$ alkoxycarbonyl;

$R^{17''}$ is defined as for $R^{17}$ above except that $R^{17''}$ does not represent a hydrogen atom;

$R^{19}$ and $R^{20}$ each independently represent a hydrogen atom or a $C_1$–$C_6$ alkyl group, or $R^{19}$ and $R^{20}$ together with the nitrogen atom to which they are attached form a 4- to 7-membered saturated heterocycle;

$R^{21}$ and $R^{22}$ each independently represent a hydrogen atom or a $C_1$–$C_6$ alkyl group optionally substituted by $C_1$–$C_6$ alkoxycarbonyl;

v is 0 or 1;

$R^{23}$ represents a hydrogen atom or a $C_1$–$C_6$ alkyl group; and $R^{24}$ represents a hydrogen atom, or a $C_1$–$C_6$ alkyl group optionally substituted by carboxyl, $C_1$–$C_6$ alkoxy or $C_1$–$C_6$ alkoxycarbonyl; provided that when X is an oxygen atom or a group $CH_2$, Y is CH, $Z^1$ and $Z^2$ each represent a group $CH_2$ and Q is an oxygen atom, then $R^2$ is other than an unsubstituted indolyl group;

or a pharmaceutically acceptable salt or solvate thereof.

In the context of the present specification, an alkyl substituent group or an alkyl moiety in a substituent group may be linear or branched.

In one aspect of the present invention, there is provided a compound of general formula:

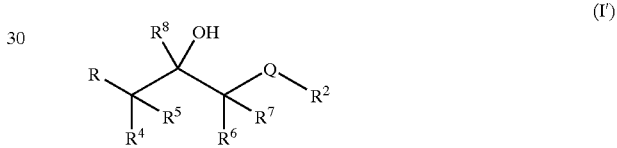

(I')

wherein,

R represents a group:

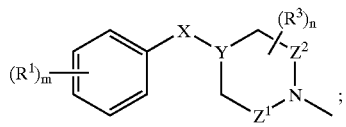

m is 0, 1, 2 or 3;

each $R^1$ independently represents halogen, cyano, nitro, carboxyl, hydroxyl, $C_3$–$C_6$ cycloalkyl, $C_1$–$C_6$ alkoxy, $C_1$–$C_6$ alkoxycarbonyl, $C_1$–$C_6$ haloalkyl, $C_1$–$C_6$ haloalkoxy, —$NR^9R^{10}$, $C_3$–$C_6$ cycloalkylamino, $C_1$–$C_6$ alkylthio, $C_1$–$C_6$ alkylcarbonyl, $C_1$–$C_6$ alkylcarbonylamino, sulphonamido, $C_1$–$C_6$ alkylsulphonyl, —$C(O)NR^{11}R^{12}$, —$NR^{13}C(O)(NH)_pR^{14}$, phenyl, or $C_1$–$C_6$ alkyl optionally substituted by carboxyl or $C_1$–$C_6$ alkoxycarbonyl;

p is 0 or 1;

X represents an oxygen or sulphur atom or a $CH_2$, $CH(CH_3)$, $OCH_2$, $CH_2O$, $CH_2NH$, NH or carbonyl group and Y represents a nitrogen atom or a CH or C(OH) group, provided that when X represents an oxygen or sulphur atom or a $CH_2O$, $CH_2NH$ or NH group, then Y represents a CH group;

$Z^1$ represents a bond or a group $(CH_2)_q$ where q is 1 or 2;

$Z^2$ represents a bond or a group $CH_2$, with the proviso that $Z^1$ and $Z^2$ do not both simultaneously represent a bond;

Q represents an oxygen or sulphur atom or a group $CH_2$ or NH;

$R^2$ represents a group

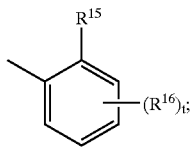

n is 0, 1 or 2;

each $R^3$ independently represents a $C_1$–$C_6$ alkyl, $C_1$–$C_6$ alkoxycarbonyl, —$CH_2OH$ or carboxyl group;

$R^4$, $R^5$, $R^6$ and $R^7$ each independently represent a hydrogen atom or a $C_1$–$C_6$ alkyl group, or $R^4$, $R^5$, $R^6$ and $R^7$ together represent a $C_1$–$C_4$ alkylene chain linking the two carbon atoms to which they are attached to form a 4- to 7-membered saturated carbocycle, or $R^5$, $R^6$ and $R^7$ each represent a hydrogen atom and $R^4$ and $R^8$ together with the carbon atoms to which they are attached form a 5- to 6-membered saturated carbocycle;

$R^8$ represents a hydrogen atom, a $C_1$–$C_6$ alkyl group or is linked to $R^4$ as defined above;

$R^9$ and $R^{10}$ each independently represent a hydrogen atom or a $C_1$–$C_6$ alkyl group, or $R^9$ and $R^{10}$ together with the nitrogen atom to which they are attached form a 4- to 7-membered saturated heterocycle;

$R^{11}$ and $R^{12}$ each independently represent a hydrogen atom or a $C_1$–$C_6$ alkyl group optionally substituted by $C_1$–$C_6$ alkoxycarbonyl;

$R^{13}$ represents a hydrogen atom or a $C_1$–$C_6$ alkyl group;

$R^{14}$ represents a hydrogen atom, or a $C_1$–$C_6$ alkyl group optionally substituted by carboxyl, $C_1$–$C_6$ alkoxy or $C_1$–$C_6$ alkoxycarbonyl;

$R^{15}$ represents carboxyl, $C_1$–$C_6$ alkylcarbonyl, $C_1$–$C_6$ alkoxycarbonyl, $C_1$–$C_6$ alkoxycarbonyl$C_1$–$C_6$ alkyl or a group —$NR^{17}R^{18}$, —$NHSO_2CH_3$, —$NHC(O)CH_3$, —$C(O)NR^{17}R^{18}$, —$NHC(O)NR^{17}R^{18}$, —$OC(O)NR^{17}R^{18}$, —$OCH_2C(O)NR^{17}R^{18}$, —$NHC(O)OR^{17'}$ or —$OR^{17''}$;

t is 0, 1, 2 or 3;

each $R^{16}$ independently represents halogen, cyano, nitro, carboxyl, hydroxyl, $C_3$–$C_6$ cycloalkyl, $C_1$–$C_6$ alkoxy, $C_1$–$C_6$ alkoxycarbonyl, $C_1$–$C_6$ haloalkyl, $C_1$–$C_6$ haloalkoxy, —$NR^{19}R^{20}$, $C_3$–$C_6$ cycloalkylamino, $C_1$–$C_6$ alkylthio, $C_1$–$C_6$ alkylcarbonyl, $C_1$–$C_6$ alkylcarbonylamino, sulphonamido (—$SO_2NH_2$), $C_1$–$C_6$ alkylsulphonyl, —$C(O)NR^{21}R^{22}$, —$NR^{23}C(O)(NH)_vR^{24}$, phenyl, or $C_1$–$C_6$ alkyl optionally substituted by carboxyl or $C_1$–$C_6$ alkoxycarbonyl;

$R^{17}$ and $R^{18}$ each independently represent (i) a hydrogen atom, (ii) a 5- to 6-membered saturated or unsaturated ring which may comprise at least one heteroatom chosen from nitrogen, oxygen and sulphur, the ring being optionally substituted with at least one substituent selected from halogen, methyl and trifluoromethyl, or (iii) a $C_1$–$C_6$ alkyl group optionally substituted by at least one substituent selected from halogen, trifluoromethyl, carboxyl, $C_1$–$C_6$ alkoxycarbonyl and a 5- to 6-membered saturated or unsaturated ring which may comprise at least one heteroatom chosen from nitrogen, oxygen and sulphur, the ring being optionally substituted with at least one substituent selected from halogen, methyl and trifluoromethyl, or $R^{17}$ and $R^{18}$ together with the nitrogen atom to which they are attached form a 4- to 7-membered saturated heterocycle;

$R^{17'}$ represents a hydrogen atom, or a $C_1$–$C_6$ alkyl group optionally substituted by carboxyl or $C_1$–$C_6$ alkoxycarbonyl;

$R^{17''}$ is defined as for $R^{17}$ above except that $R^{17''}$ does not represent a hydrogen atom;

$R^{19}$ and $R^{20}$ each independently represent a hydrogen atom or a $C_1$–$C_6$ alkyl group, or $R^{19}$ and $R^{20}$ together with the nitrogen atom to which they are attached form a 4- to 7-membered saturated heterocycle;

$R^{21}$ and $R^{22}$ each independently represent a hydrogen atom or a $C_1$–$C_6$ alkyl group optionally substituted by $C_1$–$C_6$ alkoxycarbonyl;

v is 0 or 1;

$R^{23}$ represents a hydrogen atom or a $C_1$–$C_6$ alkyl group; and $R^{24}$ represents a hydrogen atom, or a $C_1$–$C_6$ alkyl group optionally substituted by carboxyl, $C_1$–$C_6$ alkoxy or $C_1$–$C_6$ alkoxycarbonyl;

or a pharmaceutically acceptable salt or solvate thereof.

In another aspect of the invention, there is provided a compound of general formula:

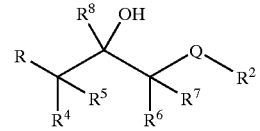

(I'')

wherein,

R represents a group:

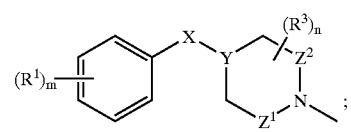

m is 0 1, 2 or 3;

each $R^1$ independently represents halogen, cyano, nitro, carboxyl, hydroxyl, $C_3$–$C_6$ cycloalkyl, $C_1$–$C_6$ alkoxy, $C_1$–$C_6$ alkoxycarbonyl, $C_1$–$C_6$ haloalkyl, $C_1$–$C_6$ haloalkoxy, —$NR^9R^{10}$, $C_3$–$C_6$ cycloalkylamino, $C_1$–$C_6$ alkylthio, $C_1$–$C_6$ alkylcarbonyl, $C_1$–$C_6$ alkylcarbonylamino, sulphonamido, $C_1$–$C_6$ alkylsulphonyl, —$C(O)NR^{11}R^{12}$, —$NR^{13}C(O)(NH)_p R^{14}$, phenyl, or $C_1$–$C_6$ alkyl optionally substituted by carboxyl or $C_1$–$C_6$ alkoxycarbonyl;

p is 0 or 1;

X represents an oxygen or sulphur atom or a $CH_2$, $CH(CH_3)$, $OCH_2$, $CH_2O$, $CH_2NH$, NH or carbonyl group and Y represents a nitrogen atom or a CH or C(OH) group, provided that when X represents an oxygen or sulphur atom or a $CH_2O$, $CH_2NH$ or NH group, then Y represents a CH group;

$Z^1$ represents a bond or a group $(CH_2)_q$ where q is 1 or 2;

$Z^2$ represents a bond or a group $CH_2$, with the proviso that $Z^1$ and $Z^2$ do not both simultaneously represent a bond;

Q represents an oxygen or sulphur atom or a group $CH_2$ or NH;

$R^2$ represents a group:

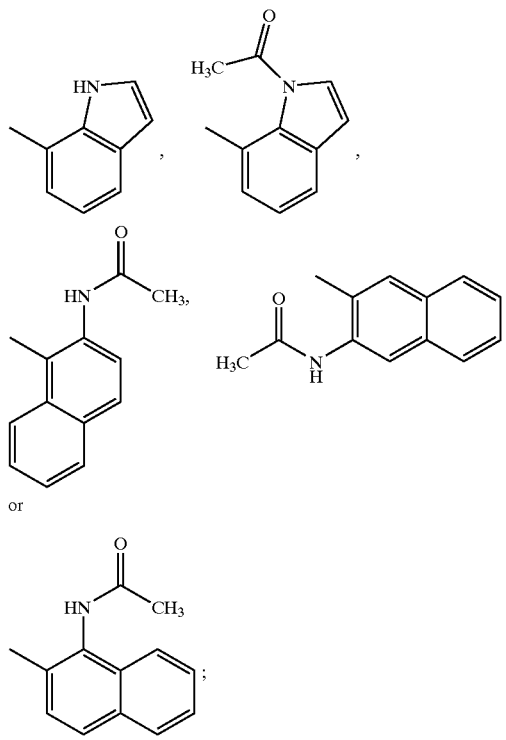

n is 0, 1 or 2;

each $R^3$ independently represents a $C_1$–$C_6$ alkyl, $C_1$–$C_6$ alkoxycarbonyl, —$CH_2OH$ or carboxyl group;

$R^4$, $R^5$, $R^6$ and $R^7$ each independently represent a hydrogen atom or a $C_1$–$C_6$ alkyl group, or $R^4$, $R^5$, $R^6$ and $R^7$ together represent a $C_1$–$C_4$ alkylene chain linking the two carbon atoms to which they are attached to form a 4- to 7-membered saturated carbocycle, or $R^5$, $R^6$ and $R^7$ each represent a hydrogen atom and $R^4$ and $R^8$ together with the carbon atoms to which they are attached form a 5- to 6-membered saturated carbocycle;

$R^8$ represents a hydrogen atom, a $C_1$–$C_6$ alkyl group or is linked to $R^4$ as defined above;

$R^9$ and $R^{10}$ each independently represent a hydrogen atom or a $C_1$–$C_6$ alkyl group, or $R^9$ and $R^{10}$ together with the nitrogen atom to which they are attached form a #4- to 7-membered saturated heterocycle;

$R^{11}$ and $R^{12}$ each independently represent a hydrogen atom or a $C_1$–$C_6$ alkyl group optionally substituted by $C_1$–$C_6$ alkoxycarbonyl;

$R^{13}$ represents a hydrogen atom or a $C_1$–$C_6$ alkyl group; and $R^{14}$ represents a hydrogen atom, or a $C_1$–$C_6$ alkyl group optionally substituted by carboxyl, $C_1$–$C_6$ alkoxy or $C_1$–$C_6$ alkoxycarbonyl; provided that when X is an oxygen atom or a group $CH_2$, Y is CH, $Z^1$ and $Z^2$ each represent a group $CH_2$ and Q is an oxygen atom, then R is other than an unsubstituted indolyl group;

or a pharmaceutically acceptable salt or solvate thereof.

In a further aspect of the invention, there is provided a compound of general formula:

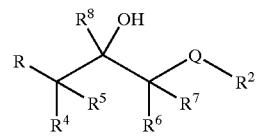

(I''')

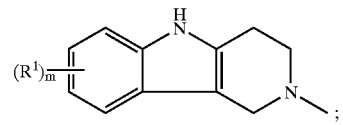

wherein,

R represents a group:

m is 0, 1, 2 or 3;

each $R^1$ independently represents halogen, cyano, nitro, carboxyl, hydroxyl, $C_3$–$C_6$ cycloalkyl, $C_1$–$C_6$ alkoxy, $C_1$–$C_6$ alkoxycarbonyl, $C_1$–$C_6$ haloalkyl, $C_1$–$C_6$ haloalkoxy, —$NR^9R^{10}$, $C_3$–$C_6$ cycloalkamino, $C_1$–$C_6$ alkylthio, $C_1$–$C_6$ alkylcarbonyl, $C_1$–$C_6$ alkylcarbonylamino, sulphonamido, $C_1$–$C_6$ alkylsulphonyl, —$C(O)NR^{11}R^{12}$, —$NR^{13}C(O)$—$(NH)_p R^{14}$, phenyl, or $C_1$–$C_6$ alkyl optionally substituted by carboxyl or $C_1$–$C_6$ alkoxycarbonyl;

p is 0 or 1;

Q represents an oxygen or sulphur atom or a group $CH_2$ or NH;

$R^2$ represents a group:

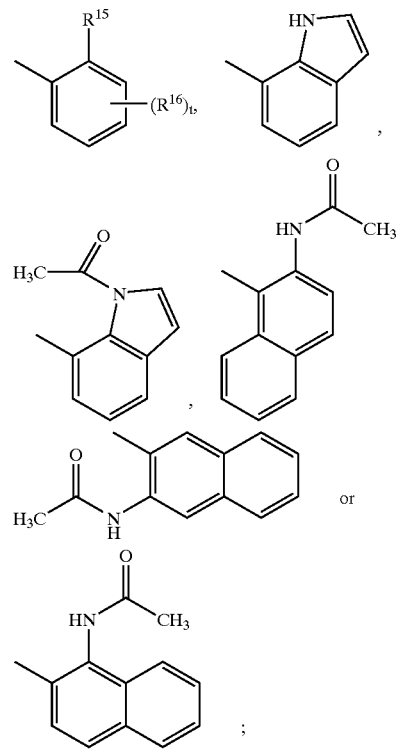

$R^4$, $R^5$, $R^6$ and $R^7$ each independently represent a hydrogen atom or a $C_1$–$C_6$ alkyl group, or $R^4$, $R^5$, $R^6$ and $R^7$ together represent a $C_1$–$C_4$ alkylene chain linking the two carbon atoms to which they are attached to form a 4- to 7-membered saturated carbocycle, or $R^5$, $R^6$ and $R^7$ each represent a hydrogen atom and $R^4$ and $R^8$ together with the carbon atoms to which they are attached form a 5- to 6-membered saturated carbocycle;

$R^8$ represents a hydrogen atom, a $C_1$–$C_6$ alkyl group or is linked to $R^4$ as defined above;

$R^9$ and $R^{10}$ each independently represent a hydrogen atom or a $C_1$–$C_6$ alkyl group, or $R^9$ and $R^{10}$ together with the nitrogen atom to which they are attached form a 4- to 7-membered saturated heterocycle;

$R^{11}$ and $R^{12}$ each independently represent a hydrogen atom or a $C_1$–$C_6$ alkyl group optionally substituted by $C_1$–$C_6$ alkoxycarbonyl;

$R^{13}$ represents a hydrogen atom or a $C_1$–$C_6$ alkyl group;

$R^{14}$ represents a hydrogen atom, or a $C_1$–$C_6$ alkyl group optionally substituted by carboxyl, $C_1$–$C_6$ alkoxy or $C_1$–$C_6$ alkoxycarbonyl;

$R^{15}$ represents carboxyl, $C_1$–$C_6$ alkylcarbonyl, $C_1$–$C_6$ alkoxycarbonyl, $C_1$–$C_6$ alkoxycarbonyl$C_1$–$C_6$ alkyl or a group —$NR^{17}R^{18}$, —$NHSO_2CH_3$, —$NHC(O)CH_3$, —$C(O)NR^{17}R^{18}$, —$NHC(O)NR^{17}R^{18}$, —$OC(O)NR^{17}R^{18}$, —$OCH_2C(O)NR^{17}R^{18}$, —$NHC(O)OR^{17'}$ or —$OR^{17''}$;

t is 0, 1, 2 or 3;

each $R^{16}$ independently represents halogen, cyano, nitro, carboxyl, hydroxyl, $C_3$–$C_6$ cycloalkyl, $C_1$–$C_6$ alkoxy, $C_1$–$C_6$ alkoxycarbonyl, $C_1$–$C_6$ haloalkyl, $C_1$–$C_6$ haloalkoxy, —$NR^{19}R^{20}$, $C_3$–$C_6$ cycloalkylamino, $C_1$–$C_6$ alkylthio, $C_1$–$C_6$ alkylcarbonyl, $C_1$–$C_6$ alkylcarbonylamino, sulphonamido (—$SO_2NH_2$), $C_1$–$C_6$ alkylsulphonyl, —$C(O)NR^{21}R^{22}$, —$NR^{23}C(O)(NH)_vR^{24}$, phenyl, or $C_1$–$C_6$ alkyl optionally substituted by carboxyl or $C_1$–$C_6$ alkoxycarbonyl;

$R^{17}$ and $R^{18}$ each independently represent (i) a hydrogen atom, (ii) a 5- to 6-membered saturated or unsaturated ring which may comprise at least one heteroatom chosen from nitrogen, oxygen and sulphur, the ring being optionally substituted with at least one substituent selected from halogen, methyl and trifluoromethyl, or (iii) a $C_1$–$C_6$ alkyl group optionally substituted by at least one substituent selected from halogen, trifluoromethyl, carboxyl, $C_1$–$C_6$ alkoxycarbonyl and a 5- to 6-membered saturated or unsaturated ring which may comprise at least one heteroatom chosen from nitrogen, oxygen and sulphur, the ring being optionally substituted with at least one substituent selected from halogen, methyl and trifluoromethyl, or $R^{17}$ and $R^{18}$ together with the nitrogen atom to which they are attached form a 4- to 7-membered saturated heterocycle;

$R^{17'}$ represents a hydrogen atom, or a $C_1$–$C_6$ alkyl group optionally substituted by carboxyl or $C_1$–$C_6$ alkoxycarbonyl;

$R^{17''}$ is defined as for $R^{17'}$ above except that $R^{17''}$ does not represent a hydrogen atom;

$R^{19}$ and $R^{20}$ each independently represent a hydrogen atom or a $C_1$–$C_6$ alkyl group, or $R^{19}$ and $R^{20}$ together with the nitrogen atom to which they are attached form a 4- to 7-membered saturated heterocycle;

$R^{21}$ and $R^{22}$ each independently represent a hydrogen atom or a $C_1$–$C_6$ alkyl group optionally substituted by $C_1$–$C_6$ alkoxycarbonyl;

v is 0 or 1;

$R^{23}$ represents a hydrogen atom or a $C_1$–$C_6$ alkyl group; and $R^{24}$ represents a hydrogen atom, or a $C_1$–$C_6$ alkyl group optionally substituted by carboxyl, $C_1$–$C_6$ alkoxy or $C_1$–$C_6$ alkoxycarbonyl; or a pharmaceutically acceptable salt or solvate thereof.

The integer m is preferably 0, 1 or 2.

Each $R^1$ independently represents halogen (e.g. chlorine, fluorine, bromine or iodine), cyano, nitro, carboxyl, hydroxyl, $C_3$–$C_6$ cycloalkyl (cyclopropyl, cyclobutyl, cyclopentyl or cyclohexyl), $C_1$–$C_6$, preferably $C_1$–$C_4$, alkoxy (e.g. methoxy, ethoxy, n-propoxy or n-butoxy), $C_1$–$C_6$, preferably $C_1$–$C_4$, alkoxycarbonyl (e.g. methoxycarbonyl or ethoxycarbonyl), $C_1$–$C_6$, preferably $C_1$–$C_4$, haloalkyl (e.g. trifluoromethyl), $C_1$–$C_6$, preferably $C_1$–$C_4$, haloalkoxy (e.g. trifluoromethoxy), —$NR^9R^{10}$, $C_3$–$C_6$ cycloalkylamino (e.g. cyclopropylamino, cyclobutylamino, cyclopentylamino or cyclohexylamino), $C_1$–$C_6$, preferably $C_1$–$C_4$, alkylthio (e.g. methylthio or ethylthio), $C_1$–$C_6$, preferably $C_1$–$C_4$, alkylcarbonyl (e.g. methylcarbonyl, ethylcarbonyl, n-propylcarbonyl, isopropylcarbonyl, n-butylcarbonyl, n-pentylcarbonyl or n-hexylcarbonyl), $C_1$–$C_6$, preferably $C_1$–$C_4$, alkylcarbonylamino (e.g. methylcarbonylamino or ethylcarbonylamino), sulphonamido, $C_1$–$C_6$, preferably $C_1$–$C_4$, alkylsulphonyl (e.g. methylsulphonyl, ethylsulphonyl, n-propylsulphonyl, isopropylsulphonyl, n-butylsulphonyl, pentylsulphonyl or n-hexylsulphonyl), —$C(O)NR^{11}R^{12}$, —$NR^{13}C(O)$—$(NH)_pR^{14}$, phenyl, or $C_1$–$C_6$, preferably $C_1$–$C_4$, alkyl (e.g. methyl, ethyl, n-propyl, isopropyl, n-butyl, isobutyl, tert-butyl, n-pentyl or n-hexyl) optionally substituted by carboxyl or $C_1$–$C_6$, preferably $C_1$–$C_4$, alkoxycarbonyl (e.g. methoxycarbonyl or ethoxycarbonyl).

Most preferably, each $R^1$ independently represents halogen (particularly chlorine or fluorine), cyano, nitro, $C_1$–$C_6$ alkoxy (especially methoxy), $C_1$–$C_6$ alkylcarbonyl (especially methylcarbonyl) or $C_1$–$C_6$ alkylcarbonylamino (particularly methylcarbonylamio).

Preferably X represents an oxygen atom or a $CH_2$, $OCH_2$, $CH_2O$, NH or carbonyl group.

Preferably Y represents a nitrogen atom or CH group.

Preferred combinations of X—Y include O—CH, $OCH_2$—CH, NH—CH, $CH_2O$—CH, $CH_2$—N, C(O)—N and $CH_2$—CH.

Preferred combinations of Y, $Z^1$ and $Z^2$ include:

| Y | $Z^1$ | $Z^2$ |
| --- | --- | --- |
| CH | $CH_2$ | bond |
| CH | bond | $CH_2$ |
| CH | $CH_2$ | $CH_2$ |
| CH | $(CH_2)_2$ | bond |
| N | $CH_2$ | $CH_2$ |

Q preferably represents an oxygen atom.

Each $R^3$ independently represents a $C_1$–$C_6$, preferably $C_1$–$C_4$, alkyl (e.g. methyl, ethyl, n-propyl, isopropyl, n-butyl, isobutyl, tert-butyl, n-pentyl or n-hexyl), $C_1$–$C_6$, preferably $C_1$–$C_4$, alkoxycarbonyl (e.g. methoxycarbonyl or ethoxycarbonyl), —$CH_2OH$ or carboxyl group. It is preferred that $R^3$ represents a methyl, methoxycarbonyl, ethoxycarbonyl, —$CH_2OH$ or carboxyl group.

$R^4$, $R^5$, $R^6$ and $R^7$ each independently represent a hydrogen atom or a $C_1$–$C_6$, preferably $C_1$–$C_4$, alkyl (e.g. methyl, ethyl, n-propyl, isopropyl, n-butyl, isobutyl, tert-butyl, n-pentyl or n-hexyl), or $R^4$, $R^5$, $R^6$ and $R^7$ together represent a $C_1$–$C_4$ alkylene chain linking the two carbon atoms to which they are attached to form a #4- to 7-membered saturated carbocycle (e.g. cyclohexyl or preferably cyclopentyl), or $R^5$, $R^6$ and $R^7$ each represent a hydrogen atom and $R^4$ and $R^8$ together with the carbon atoms to which they are attached form a 5- to 6-membered saturated carbocycle (preferably cyclopentyl).

$R^8$ represents a hydrogen atom, a $C_1$–$C_6$, preferably $C_1$–$C_4$, alkyl group (e.g. methyl, ethyl, n-propyl, isopropyl, n-butyl, isobutyl, tert-butyl, n-pentyl or n-hexyl) or is linked to $R^4$ as defined above.

$R^9$ and $R^{10}$ each independently represent a hydrogen atom or a $C_1$–$C_6$, preferably $C_1$–$C_4$, alkyl group (e.g. methyl, ethyl, n-propyl, isopropyl, n-butyl, isobutyl, tert-butyl, n-pentyl or n-hexyl), or $R^9$ and $R^{10}$ together with the nitrogen atom to which they are attached form a 4- to 7-membered saturated heterocycle (preferably pyrrolidinyl or piperidinyl).

$R^{11}$ and $R^{12}$ each independently represent a hydrogen atom or a $C_1$–$C_6$, preferably $C_1$–$C_4$, alkyl group (e.g. methyl, ethyl, n-propyl, isopropyl, n-butyl, isobutyl, tert-butyl, n-pentyl or n-hexyl) optionally substituted by a $C_1$–$C_6$, preferably $C_1$–$C_4$, alkoxycarbonyl substituent group.

$R^{13}$ represents a hydrogen atom or a $C_1$–$C_6$, preferably $C_1$–$C_4$, alkyl group (e.g. methyl, ethyl, n-propyl, isopropyl, n-butyl, isobutyl, tert-butyl, n-pentyl or n-hexyl).

$R^{14}$ represents a hydrogen atom, or a $C_1$–$C_6$, preferably $C_1$–$C_4$, alkyl group (e.g. methyl, ethyl, n-propyl, isopropyl, n-butyl, isobutyl, tert-butyl, n-pentyl or n-hexyl) optionally substituted by carboxyl, $C_1$–$C_6$, preferably $C_1$–$C_4$, alkoxy or $C_1$–$C_6$, preferably $C_1$–$C_4$, alkoxycarbonyl.

$R^{15}$ represents carboxyl, $C_1$–$C_6$, preferably $C_1$–$C_4$, alkylcarbonyl (e.g. methylcarbonyl, ethylcarbonyl, n-propylcarbonyl, isopropylcarbonyl, n-butylcarbonyl, n-pentylcarbonyl or n-hexylcarbonyl), $C_1$–$C_6$, preferably $C_1$–$C_4$, alkoxycarbonyl (e.g. methoxycarbonyl or ethoxycarbonyl), $C_1$–$C_6$ alkoxycarbonyl$C_1$–$C_6$ alkyl, preferably $C_1$–$C_4$ alkoxycarbonyl$C_1$–$C_4$ alkyl (e.g. methoxycarbonylmethyl or methoxycarbonylethyl), or a group —$NR^{17}R^{18}$, —$NHSO_2CH_3$, —$NHC(O)CH_3$, —$C(O)NR^{17}R^{18}$, —$NHC(O)NR^{17}R^{18}$, —$OC(O)NR^{17}R^{18}$, —$OCH_2C(O)NR^{17}R^{18}$, —$NHC(O)OR^{17'}$ or —$OR^{17''}$.

It is preferred that $R^{15}$ represents $C_1$–$C_4$ alkoxy (especially methoxy), $C_1$–$C_4$ alkylcarbonyl (especially methylcarbonyl or ethylcarbonyl), $C_1$–$C_4$ alkoxycarbonyl$C_1$–$C_4$ alkyl (particularly methoxycarbonylmethyl or methoxycarbonylethyl), —$NHC(O)CH_3$, —$C(O)NR^{17}R^{18}$, —$NHSO_2CH_3$ or —$NHC(O)NR^{17}R^{18}$.

Each $R^{16}$ independently represents halogen (e.g. chlorine, fluorine, bromine or iodine), cyano, nitro, carboxyl, hydroxyl, $C_3$–$C_6$ cycloalkyl (cyclopropyl, cyclobutyl, cyclopentyl or cyclohexyl), $C_1$–$C_6$, preferably $C_1$–$C_4$, alkoxy (e.g. methoxy, ethoxy, n-propoxy or n-butoxy), $C_1$–$C_6$, preferably $C_1$–$C_4$, alkoxycarbonyl (e.g. methoxycarbonyl or ethoxycarbonyl), $C_1$–$C_6$, preferably $C_1$–$C_4$, haloalkyl (e.g. trifluoromethyl), $C_1$–$C_6$, preferably $C_1$–$C_4$, haloalkoxy (e.g. trifluoromethoxy), —$NR^{19}R^{20}$, $C_3$–$C_6$ cycloalkylamino (e.g. cyclopropylamino, cyclobutylamino, cyclopentylamino or cyclohexylamino), $C_1$–$C_6$, preferably $C_1$–$C_4$, alkylthio (e.g. methylthio or ethylthio), $C_1$–$C_6$, preferably $C_1$–$C_4$, alkylcarbonyl (e.g. methylcarbonyl, ethylcarbonyl, n-propylcarbonyl, isopropylcarbonyl, n-butylcarbonyl, n-pentylcarbonyl or n-hexylcarbonyl), $C_1$–$C_6$, preferably $C_1$–$C_4$, alkylcarbonylamino (e.g. methylcarbonylamino or ethylcarbonylamino), sulphonamido, $C_1$–$C_6$, preferably $C_1$–$C_4$, alkylsulphonyl (e.g. methylsulphonyl, ethylsulphonyl, n-propylsulphonyl, isopropylsulphonyl, n-butylsulphonyl, n-pentylsulphonyl or n-hexylsulphonyl), —$C(O)NR^{21}R^{22}$, —$NR^{23}C(O)$—$(NH)_yR^{24}$, phenyl, or $C_1$–$C_6$, preferably $C_1$–$C_4$, alkyl (e.g. methyl, ethyl, n-propyl, isopropyl, n-butyl, isobutyl, tert-butyl, n-pentyl or n-hexyl) optionally substituted by carboxyl or $C_1$–$C_6$, preferably $C_1$–$C_4$, alkoxycarbonyl (e.g. methoxycarbonyl or ethoxycarbonyl).

Preferably, each $R^{16}$ independently represents halogen (particularly chlorine or fluorine), hydroxyl, cyano, $C_1$–$C_4$ alkoxy (especially methoxy), $C_1$–$C_4$ alkoxycarbonyl (especially methoxycarbonyl), $C_1$–$C_4$ haloalkyl (especially trifluoromethyl), $C_1$–$C_4$ alkylcarbonyl (particularly methylcarbonyl), phenyl or $C_1$–$C_4$ alkyl (e.g. methyl or tert-butyl).

$R^{17}$ and $R^{18}$ each independently represent (i) a hydrogen atom, (ii) a 5- to 6-membered saturated or unsaturated ring which may comprise at least one heteroatom (e.g. one, two or three heteroatoms independently) chosen from nitrogen, oxygen and sulphur (such as cyclopentyl, cyclohexyl, pyrolyl, imidazolyl, pyridinyl, pyrazinyl, pyridazinyl, pyrimidinyl, thienyl or furanyl), the ring being optionally substituted with at least one substituent (e.g. one, two or three substituents independently) selected from halogen (e.g. fluorine, chlorine, bromine or iodine), methyl and trifluoromethyl, or (iii) a $C_1$–$C_6$, preferably $C_1$–$C_4$, alkyl group (e.g. methyl, ethyl, n-propyl, isopropyl, n-butyl, isobutyl, tert-butyl, n-pentyl or n-hexyl) optionally substituted by at least one substituent (e.g. one, two or three substituents independently) selected from halogen (e.g. fluorine, chlorine, bromine or iodine), trifluoromethyl, carboxyl, $C_1$–$C_6$, preferably $C_1$–$C_4$, alkoxycarbonyl, especially methoxycarbonyl, and a 5- to 6-membered saturated or unsaturated ring which may comprise at least one heteroatom (e.g. one, two or three heteroatoms independently) chosen from nitrogen, oxygen and sulphur (such as cyclopentyl, cyclohexyl, pyrolyl, imidazolyl, pyridinyl, pyrazinyl, pyridazinyl, pyrimidinyl, thienyl or furanyl), the ring being optionally substituted with at least one substituent (e.g. one, two or three substituents independently) selected from halogen (e.g. fluorine, chlorine, bromine or iodine), methyl and trifluoromethyl, or $R^{17}$ and $R^{18}$ together with the nitrogen atom to which they are attached form a 4- to 7-membered saturated heterocycle (preferably pyrrolidinyl or piperidinyl).

$R^{17'}$ represents a hydrogen atom or a $C_1$–$C_6$, preferably $C_1$–$C_4$, alkyl group (e.g. methyl, ethyl, n-propyl, isopropyl, n-butyl, isobutyl, tert-butyl, n-pentyl or n-hexyl) optionally substituted by carboxyl or, more preferably, $C_1$–$C_6$, preferably $C_1$–$C_4$, alkoxycarbonyl, especially methoxycarbonyl, $R^{19}$ and $R^{20}$ each independently represent a hydrogen atom or a $C_1$–$C_6$, preferably $C_1$–$C_4$, alkyl group (e.g. methyl, ethyl, n-propyl, isopropyl, n-butyl, isobutyl, tert-butyl, n-pentyl or n-hexyl), or $R^{19}$ and $R^{20}$ together with the nitrogen atom to which they are attached form a 4- to 7-membered saturated heterocycle (preferably pyrrolidinyl or piperidinyl).

$R^{21}$ and $R^{22}$ each independently represent a hydrogen atom or a $C_1$–$C_6$, preferably $C_1$–$C_4$, alkyl group (e.g. methyl, ethyl, n-propyl, isopropyl, n-butyl, isobutyl, tert-butyl, n-pentyl or n-hexyl) optionally substituted by a $C_1$–$C_6$, preferably $C_1$–$C_4$, alkoxycarbonyl substituent group.

$R^{23}$ represents a hydrogen atom or a $C_1$–$C_6$, preferably $C_1$–$C_4$, alkyl group (e.g. methyl, ethyl, n-propyl, isopropyl, n-butyl, isobutyl, tert-butyl, n-pentyl or n-hexyl).

$R^{24}$ represents a hydrogen atom, or a $C_1$–$C_6$, preferably $C_1$–$C_4$, alkyl group (e.g. methyl, ethyl, n-propyl, isopropyl, n-butyl, isobutyl, tert-butyl, n-pentyl or n-hexyl) optionally substituted by carboxyl, $C_1$–$C_6$, preferably $C_1$–$C_4$, alkoxy or $C_1$–$C_6$, preferably $C_1$–$C_4$, alkoxycarbonyl.

Preferred compounds of the invention include:
N-(2-{3-[3R,S-(4-Chloro-phenoxy)-pyrrolidin-1-yl]-2R,S-hydroxy-propoxy}-phenyl)-acetamide hydrochloride,
N-(5-Chloro-2-{3-[3R,S-(4-Chloro-phenoxy)-pyrrolidin-1-yl]-2R,S-hydroxy-propoxy}-phenyl)-acetamide hydrochloride,
N-(2-{3-[4-(3,4-Dichlorophenoxy)-1-piperidinyl]-2-hydroxypropoxy}phenyl)-acetamide,
1-(2-Aminophenoxy)-3-[4-(3,4-dichlorophenoxy)-1-piperidinyl]-2-propanol dihydrochloride,
N-(2-{3-[3-(3,4-dichlorophenoxy)-1-pyrrolidinyl)-2-hydroxypropoxy}phenyl)-acetamide hydrochloride,
2-{3-[4-(4-Fluoro-phenoxy)-piperidin-1-yl]-2-hydroxy-propoxy}-benzoic acid methyl ester,
2-(2-{3-[4-(3,4-Difluoro-phenoxy)-piperidin-1-yl]-2-hydroxy-propoxy}-benzoylamino)-2-methyl-propionic acid methyl ester,
N-[2-({(1R,2S,3R)*-3-[4-(3,4-dichlorophenoxy)-1-piperidinyl)-2-hydroxycyclopentyl}oxy)phenyl] acetamide,
N-[2-({(1S,2S,3R)*-3-[4-(3,4-dichlorophenoxy)-1-piperidinyl)-2-hydroxycyclopentyl}oxy)phenyl] acetamide,
N-[2-({(2,3-trans)-3-[4-(3,4-dichlorophenoxy)-1-piperidinyl)-2-hydroxycyclohexyl}oxy)phenyl] acetamide,
N-(5-Chloro-2-{3-[3-(3,4-dichloro-phenoxy)-pyrrolidin-1-yl]-2-hydroxy-propoxy}-phenyl)-acetamide,
N-(3-Acetyl-2-{3-[3-(3,4-dichloro-phenoxy)-pyrrolidin-1-yl]-2-hydroxy-propoxy}-5-methyl-phenyl)-acetamide,
N-(2-{3-[3-(3,4-Dichloro-phenoxy)-pyrrolidin-1-yl]-2-hydroxy-propoxy}-4-methyl-phenyl)-acetamide,
N-(2-{3-[3-(3,4-Dichloro-phenoxy)-pyrrolidin-1-yl]-2-hydroxy-propoxy}-5-fluoro-phenyl)-acetamide,
1-[3-(3,4-Dichloro-phenoxy)-pyrrolidin-1-yl]-3-(1H-indol-7-yloxy)-propan-2-ol,
1-(7-{3-[3-(3,4-Dichloro-phenoxy)-pyrrolidin-1-yl]-2-hydroxy-propoxy}-indol-1-yl)-ethanone,
N-(4-{3-[3-(3,4-Dichloro-phenoxy)-pyrrolidin-1-yl]-2-hydroxy-propoxy}-biphenyl-3-yl)-acetamide,
N-(2-{3-[3-(3,4-Dichloro-phenoxy)-pyrrolidin-1-yl]-2-hydroxy-propoxy}-4-fluoro-phenyl)-acetamide,
N-(2-{3-[3-(3,4-Dichloro-phenoxy)-pyrrolidin-1-yl]-2-hydroxy-propoxy}-5-methyl-phenyl)-acetamide,
N-(2-{3-[3-(3,4-Dichloro-phenoxy)-pyrrolidin-1-yl]-2-hydroxy-propoxy}-phenyl)-acetamide,
N-(5-Chloro-2-{3-[3-(4-chloro-phenoxy)-pyrrolidin-1-yl]-2-hydroxy-propoxy}-phenyl)-acetamide,
N-(3-Acetyl-2-{3-[3-(4-chloro-phenoxy)-pyrrolidin-1-yl]-2-hydroxy-propoxy}-5-methyl-phenyl)-acetamide,
N-(2-{3-[3-(4-Chloro-phenoxy)-pyrrolidin-1-yl]-2-hydroxy-propoxy}-4-methyl-phenyl)-acetamide,
N-(2-{3-[3-(4-Chloro-phenoxy)-pyrrolidin-1-yl]-2-hydroxy-propoxy}-5-fluoro-phenyl)-acetamide,
1-[3-(4-Chloro-phenoxy)-pyrrolidin-1-yl]-3-(1H-indol-7-yloxy)-propan-2-ol,
1-(7-{3-[3-(4-Chloro-phenoxy)-pyrrolidin-1-yl]-2-hydroxy-propoxy}-indol-1-yl)-ethanone,
N-(4-{3-[3-(4-Chloro-phenoxy)-pyrrolidin-1-yl]-2-hydroxy-propoxy}-biphenyl-3-yl)-acetamide,
N-(2-{3-[3-(4-Chloro-phenoxy)-pyrrolidin-1-yl]-2-hydroxy-propoxy}-4-fluoro-phenyl)-acetamide,
N-(2-{3-[3-(4-Chloro-phenoxy)-pyrrolidin-1-yl]-2-hydroxy-propoxy}-5-methyl-phenyl)-acetamide,
N-(2-{3-[3-(4-Chloro-phenoxy)-pyrrolidin-1-yl]-2-hydroxy-propoxy}-phenyl)-acetamide
N-(5-Chloro-2-{3-[3-(4-fluoro-phenoxy)-pyrrolidin-1-yl]-2-hydroxy-propoxy}-phenyl)-acetamide,
N-(3-Acetyl-2-{3-[3-(4-fluoro-phenoxy)-pyrrolidin-1-yl]-2-hydroxy-propoxy}-5-methyl-phenyl)-acetamide,
N-(2-{3-[3-(4-Fluoro-phenoxy)-pyrrolidin-1-yl]-2-hydroxy-propoxy}-4-methyl-phenyl)-acetamide,
N-(5-Fluoro-2-{3-[3-(4-fluoro-phenoxy)-pyrrolidin-1-yl]-2-hydroxy-propoxy}-phenyl)-acetamide,
1-[3-(4-Fluoro-phenoxy)-pyrrolidin-1-yl]-3-(1H-indol-7-yloxy)-propan-2-ol,
1-(7-{3-[3-(4-Fluoro-phenoxy)-pyrrolidin-1-yl]-2-hydroxy-propoxy}-indol-1-yl)-ethanone,
N-(4-{3-[3-(4-Fluoro-phenoxy)-pyrrolidin-1-yl]-2-hydroxy-propoxy}-biphenyl-3-yl)-acetamide,
N-(4-Fluoro-2-{3-[3-(4-fluoro-phenoxy)-pyrrolidin-1-yl]-2-hydroxy-propoxy}-phenyl)-acetamide,
N-(2-{3-[3-(4-Fluoro-phenoxy)-pyrrolidin-1-yl]-2-hydroxy-propoxy}-5-methyl-phenyl)-acetamide,
N-(2-{3-[3-(4-Fluoro-phenoxy)-pyrrolidin-1-yl]-2-hydroxy-propoxy}-phenyl)-acetamide,
N-(5-Chloro-2-{3-[3-(3,4-difluoro-phenoxy)-pyrrolidin-1-yl]-2-hydroxy-propoxy}-phenyl)-acetamide,
N-(3-Acetyl-2-{3-[3-(3,4-difluoro-phenoxy)-pyrrolidin-1-yl]-2-hydroxy-propoxy}-5-methyl-phenyl)-acetamide,
N-(2-{3-[3-(3,4-Difluoro-phenoxy)-pyrrolidin-1-yl]-2-hydroxy-propoxy}-4-methyl-phenyl)-acetamide,
N-(2-{3-[3-(3,4-Difluoro-phenoxy)-pyrrolidin-1-yl]-2-hydroxy-propoxy}-5-fluoro-phenyl)-acetamide,
1-[3-(3,4-Difluoro-phenoxy)-pyrrolidin-1-yl]-3-(1H-indol-7-yloxy)-propan-2-ol,
1-(7-{3-[3-(3,4-Difluoro-phenoxy)-pyrrolidin-1-yl]-2-hydroxy-propoxy}-indol-1-yl)-ethanone,
N-(4-{3-[3-(3,4-Difluoro-phenoxy)-pyrrolidin-1-yl]-2-hydroxy-propoxy}-biphenyl-3-yl)-acetamide,
N-(2-{3-[3-(3,4-Difluoro-phenoxy)-pyrrolidin-1-yl]-2-hydroxy-propoxy}-4-fluoro-phenyl)-acetamide,
N-(2-{3-[3-(3,4-Difluoro-phenoxy)-pyrrolidin-1-yl]-2-hydroxy-propoxy}-5-methyl-phenyl)-acetamide,
N-(2-{3-[3-(3,4-Difluoro-phenoxy)-pyrrolidin-1-yl]-2-hydroxy-propoxy}-phenyl)-acetamide,
N-(5-Chloro-2-{3-[4-(3,4-dichloro-phenoxy)-piperidin-1-yl]-2-hydroxy-propoxy}-phenyl)-acetamide,
N-(3-Acetyl-2-{3-[4-(3,4-dichloro-phenoxy)-piperidin-1-yl]-2-hydroxy-propoxy}-5-methyl-phenyl)-acetamide,
N-(2-{3-[4-(3,4-Dichloro-phenoxy)-piperidin-1-yl]-2-hydroxy-propoxy}-4-methyl-phenyl)-acetamide,
N-(2-{3-[4-(3,4-Dichloro-phenoxy)-piperidin-1-yl]-2-hydroxy-propoxy}-5-fluoro-phenyl)-acetamide,
1-(7-{3-[4-(3,4-Dichloro-phenoxy)-piperidin-1-yl]-2-hydroxy-propoxy}-indol-1-yl)-ethanone,
N-(4-{3-[4-(3,4-Dichloro-phenoxy)-piperidin-1-yl]-2-hydroxy-propoxy}-biphenyl-3-yl)-acetamide,
N-(2-{3-[4-(3,4-Dichloro-phenoxy)-piperidin-1-yl]-2-hydroxy-propoxy}-4-fluoro-phenyl)-acetamide,
N-(2-{3-[4-(3,4-Dichloro-phenoxy)-piperidin-1-yl]-2-hydroxy-propoxy}-5-methyl-phenyl)-acetamide,
N-(2-{3-[4-(3,4-Dichloro-phenoxy)-piperidin-1-yl]-2-hydroxy-propoxy}-phenyl)-acetamide,
N-(5-Chloro-2-{3-[4-(4-chloro-phenoxy)-piperidin-1-yl]-2-hydroxy-propoxy}-phenyl)-acetamide,
N-(3-Acetyl-2-{3-[4-(4-chloro-phenoxy)-piperidin-1-yl]-2-hydroxy-propoxy}-5-methyl-phenyl)-acetamide,
N-(2-{3-[4-(4-Chloro-phenoxy)-piperidin-1-yl]-2-hydroxy-propoxy}-4-methyl-phenyl)-acetamide,
N-(2-{3-[4-(4-Chloro-phenoxy)-piperidin-1-yl]-2-hydroxy-propoxy}-5-fluoro-phenyl)-acetamide,
1-(7-{3-[4-(4-Chloro-phenoxy)-piperidin-1-yl]-2-hydroxy-propoxy}-indol-1-yl)-ethanone,
N-(4-{3-[4-(4-Chloro-phenoxy)-piperidin-1-yl]-2-hydroxy-propoxy}-biphenyl-3-yl)-acetamide, N-(2-{3-[4-(4-Chloro-phenoxy)-piperidin-1-yl]-2-hydroxy-propoxy}-4-fluoro-phenyl)-acetamide,
N-(2-{3-[4-(4-Chloro-phenoxy)-piperidin-1-yl]-2-hydroxy-propoxy}-5-methyl-phenyl)-acetamide,
N-(2-{3-[4-(4-Chloro-phenoxy)-piperidin-1-yl]-2-hydroxy-propoxy}-phenyl)-acetamide,
N-{5-Chloro-2-[3-(8-chloro-1,3,4,5-tetrahydro-pyrido[4,3-b]indol-2-yl)-2-hydroxy-propoxy]-phenyl}-acetamide,
N-{3-Acetyl-2-[3-(8-chloro-1,3,4,5-tetrahydro-pyrido[4,3-b]indol-2-yl)-2-hydroxy-propoxy]-5-methyl-phenyl}-acetamide,
N-{2-[3-(8-Chloro-1,3,4,5-tetrahydro-pyrido[4,3-b]indol-2-yl)-2-hydroxy-propoxy]-4-methyl-phenyl}-acetamide,
N-{2-[3-(8-Chloro-1,3,4,5-tetrahydro-pyrido[4,3-b]indol-2-yl)-2-hydroxy-propoxy]-5-fluoro-phenyl}-acetamide,
1-(8-Chloro-1,3,4,5-tetrahydro-pyrido[4,3-b]indol-2-yl)-3-(1H-indol-7-yloxy)-propan-2-ol,
1-{7-[3-(8-Chloro-1,3,4,5-tetrahydro-pyrido[4,3-b]indol-2-yl)-2-hydroxy-propoxy]-indol-1-yl}-ethanone,
N-{4-[3-(8-Chloro-1,3,4,5-tetrahydro-pyrido[4,3-b]indol-2-yl)-2-hydroxy-propoxy]-biphenyl-3-yl}-acetamide,
N-{2-[3-(8-Chloro-1,3,4,5-tetrahydro-pyrido[4,3-b]indol-2-yl)-2-hydroxy-propoxy]-4-fluoro-phenyl}-acetamide,
N-{2-[3-(8-Chloro-1,3,4,5-tetrahydro-pyrido[4,3-b]indol-2-yl)-2-hydroxy-propoxy]-5-methyl-phenyl}-acetamide,
N-{2-[3-(8-Chloro-1,3,4,5-tetrahydro-pyrido[4,3-b]indol-2-yl)-2-hydroxy-propoxy]-phenyl}-acetamide,
N-{5-Chloro-2-[3-(8-fluoro-1,3,4,5-tetrahydro-pyrido[4,3-b]indol-2-yl)-2-hydroxy-propoxy]-phenyl}-acetamide,
N-{3-Acetyl-2-[3-(8-fluoro-1,3,4,5-tetrahydro-pyrido[4,3-b]indol-2-yl)-2-hydroxy-propoxy]-5-methyl-phenyl}-acetamide,
N-{2-[3-(8-Fluoro-1,3,4,5-tetrahydro-pyrido[4,3-b]indol-2-yl)-2-hydroxy-propoxy]4-methyl-phenyl}-acetamide,
N-{5-Fluoro-2-[3-(8-fluoro-1,3,4,5-tetrahydro-pyrido[4,3-b]indol-2-yl)-2-hydroxy-propoxy]-phenyl}-acetamide,
1-(8-Fluoro-1,3,4,5-tetrahydro-pyrido[4,3-b]indol-2-yl)-3-(1H-indol-7-yloxy)-propan-2-ol,
1-{7-[3-(8-Fluoro-1,3,4,5-tetrahydro-pyrido[4,3-b]indol-2-yl)-2-hydroxy-propoxy]-indol-1-yl}-ethanone,
N-{4-[3-(8-Fluoro-1,3,4,5-tetrahydro-pyrido[4,3-b]indol-2-yl)-2-hydroxy-propoxy]-biphenyl-3-yl}-acetamide,
N-{4-Fluoro-2-[3-(8-fluoro-1,3,4,5-tetrahydro-pyrido[4,3-b]indol-2-yl)-2-hydroxy-propoxy]-phenyl}-acetamide,
N-{2-[3-(8-Fluoro-1,3,4,5-tetrahydro-pyrido[4,3-b]indol-2-yl)-2-hydroxy-propoxy]-5-methyl-phenyl}-acetamide,
N-{2-[3-(8-Fluoro-1,3,4,5-tetrahydro-pyrido[4,3-b]indol-2-yl)-2-hydroxy-propoxy]-phenyl}-acetamide,
N-(2-{3-[4-(3,4-Dichloro-phenoxy)-piperidin-1-yl]-2-hydroxy-propoxy}-phenyl)-acetamide,
3-(2-{3-[4-(3,4-Dichloro-phenoxy)-piperidin-1-yl]-2-hydroxy-propoxy}-phenyl)-propionic acid methyl ester,
1-[4-(3,4-Dichloro-phenoxy)-piperidin-1-yl]-3-(2,6-dimethoxy-phenoxy)-propan-2-ol,
1-[4-(3,4-Dichloro-phenoxy)-piperidin-1-yl]-3-(2-methoxy-phenoxy)-propan-2-ol,
2-{3-[(3,4-Dichloro-phenoxy)-piperidin-1-yl]-2-hydroxy-propoxy}-N,N-dimethyl-benzamide,
1-(2-{3-[4-(3,4-Dichloro-phenoxy)-piperidin-1-yl]-2-hydroxy-propoxy}-phenyl)-propan-1-one,
1-(2-{3-[4-(3,4-Dichloro-phenoxy)-piperidin-1-yl]-2-hydroxy-propoxy}-phenyl)-ethanone,
3-(2-{3-[3-(4-Fluoro-phenoxy)-pyrrolidin-1-yl]-2-hydroxy-propoxy}-phenyl)-propionic acid methyl ester,
1-(2,6-Diethoxy-phenoxy)-3-[3-(4-fluoro-phenoxy)-pyrrolidin-1-yl]-propan-2-ol,
1-[3-(4-Fluoro-phenoxy)-pyrrolidin-1-yl]-3-(2-methoxy-phenoxy)-propan-2-ol,
(2-{3-[3-(4-Fluoro-phenoxy)-pyrrolidin-1-yl]-2-hydroxy-propoxy}-benzoylamino)-acetic acid methyl ester,
(2-{3-[3-(4-Chloro-phenoxymethyl)-piperidin-1-yl]-2-hydroxy-propoxy}-benzoylamino)-acetic acid methyl ester,
2-(2-{3-[3-(4-Fluoro-phenoxy)-pyrrolidin-1-yl]-2-hydroxy-propoxy}-benzoylamino)-2-methyl-propionic acid methyl ester,
2-{3-[3-(4-Fluoro-phenoxy)-pyrrolidin-1-yl]-2-hydroxy-propoxy}-N,N-dimethyl-benzamide,
1-(2-{3-[3-(4-Fluoro-phenoxy)-pyrrolidin-1-yl]-2-hydroxy-propoxy}-6-methoxy-pheny)-ethanone,
1-(2-{3-[3-(4-Fluoro-phenoxy)-pyrrolidin-1-yl]-2-hydroxy-propoxy}-phenyl)-propan-1-one,
1-(2-{3-[3-(4-Fluoro-phenoxy)-pyrrolidin-1-yl]-2-hydroxy-propoxy}-phenyl)-ethanone,
N-[2-(3-{[1-(3,4-dichlorobenzyl)-4-piperidinyl]amino}-2-hydroxypropoxy)-4-methylphenyl]acetamide,
3-(2-{3-[3-(3,4-Difluoro-phenoxy)-pyrrolidin-1-yl]-2-hydroxy-propoxy}-phenyl)-propionic acid methyl ester,
1-[3-(3,4-Difluoro-phenoxy)-pyrrolidin-1-yl]-3-(2-methoxy-phenoxy)-propan-2-ol,
(2-{3-[3-(3,4-Difluoro-phenoxy)-pyrrolidin-1-yl]-2-hydroxy-propoxy}-benzoylamino)-acetic acid methyl ester,
2-{3-[3-(3,4-Difluoro-phenoxy)-pyrrolidin-1-yl]-2-hydroxy-propoxy}-N,N-dimethyl-benzamide,
1-(2-{3-[3-(3,4-Difluoro-phenoxy)-pyrrolidin-1-yl]-2-hydroxy-propoxy}-6-methoxy-phenyl)-ethanone,
1-(2-{3-[3-(3,4-Difluoro-phenoxy)-pyrrolidin-1-yl]-2-hydroxy-propoxy)-phenyl)-propan-1-one,
1-(2-{3-[3-(3,4-Difluoro-phenoxy)-pyrrolidin-1-yl]-2-hydroxy-propoxy}-phenyl)-ethanone,
N-(2-{3-[4-(3,4-dichloroanilino)-1-piperidinyl]-2-hydroxypropoxy}phenyl)acetamide,
3-(2-{3-[3-(4-Chloro-phenoxy)-pyrrolidin-1-yl]-2-hydroxy-propoxy}-phenyl)-propionic acid methyl ester,
1-[3-(4-Chloro-phenoxy)-pyrrolidin-1-yl]-3-(2,6-dimethoxy-phenoxy)-propan-2-ol,
1-[3-(4-Chloro-phenoxy)-pyrrolidin-1-yl]-3-(2-methoxy-phenoxy)-propan-2-ol,
(2-{3-[3-(4-Chloro-phenoxy)-pyrrolidin-1-yl]-2-hydroxy-propoxy}-benzoylamino)-acetic acid, methyl ester,
2-(2-{3-[3-(4-Chloro-phenoxy)-pyrrolidin-1-yl]-2-hydroxy-propoxy}-benzoylamino)-2-methyl-propionic acid methyl ester,
2-{3-[3-(4-Chloro-phenoxy)-pyrrolidin-1-yl]-2-hydroxy-propoxy}-N,N-dimethyl-benzamide,
1-(2-{3-[3-(4-Chloro-phenoxy)-pyrrolidin-1-yl]-2-hydroxy-propoxy}-6-methoxy-phenyl)-ethanone,
1-(2-{3-[3-(4-Chloro-phenoxy)-pyrrolidin-1-yl]-2-hydroxy-propoxy}-phenyl)-propan-1-one,
1-(2-{3-[3-(4-Chloro-phenoxy)-pyrrolidin-1-yl]-2-hydroxy-propoxy}-phenyl)-ethanone,
N-(2-{3-[3-(4-Cyano-phenoxy)-pyrrolidin-1-yl]-2-hydroxy-propoxy}-phenyl)-acetamide,
3-(2-{3-[3-(4-Cyano-phenoxy)-pyrrolidin-1-yl]-2-hydroxy-propoxy}-phenyl)-propionic acid methyl ester,
(2-{3-[3-(4-Cyano-phenoxy)-pyrrolidin-1-yl]-2-hydroxy-propoxy}-benzoylamino)-acetic acid methyl ester,
2-{3-[3-(4-Cyano-phenoxy)-pyrrolidin-1-yl]-2-hydroxy-propoxy}-N,N-dimethyl-benzamide,
4-{1-[2-Hydroxy-3-(2-propionyl-phenoxy)-propyl]-pyrrolidin-3-yloxy}-benzonitrile,
N-(2-{2-Hydroxy-3-[3-(4-methoxy-phenoxy)-pyrrolidin-1-yl]-propoxy}-phenyl)-acetamide,
N-(4-chloro-2-{3-[4-(3,4-dichloroanilino)-1-piperidinyl]-2-hydroxypropoxy}phenyl)acetamide, 3-(2-{3-[3-(3,4-Dichloro-phenoxy)-pyrrolidin-1-yl]-2-hydroxy-propoxy}-phenyl)-propionic acid methyl ester,
1-[3-(3,4-Dichloro-phenoxy)-pyrrolidin-1-yl]-3-(2-methoxy-phenoxy)-propan-2-ol,
(2-{3-[3-(3,4-Dichloro-phenoxy)-pyrrolidin-1-yl]-2-hydroxy-propoxy}-benzoylamino)-acetic acid methyl ester,
2-(2-{3-[3-(3,4-Dichloro-phenoxy)-pyrrolidin-1-yl]-2-hydroxy-propoxy}-benzoylamino)-2-methyl-propionic acid methyl ester,
2-{3-[3-(3,4-Dichloro-phenoxy)-pyrrolidin-1-yl]-2-hydroxy-propoxy}-N,N-dimethyl-benzamide,
1-(2-{3-[3-(3,4-Dichloro-phenoxy)-pyrrolidin-1-yl]-2-hydroxy-propoxy}-6-methoxy-phenyl)-ethanone,
1-(2-{3-[3-(3,4-Dichloro-phenoxy)-pyrrolidin-1-yl]-2-hydroxy-propoxy}-phenyl)-propan-1-one,
1-(2-{3-[3-(3,4-Dichloro-phenoxy)-pyrrolidin-1-yl]-2-hydroxy-propoxy}-phenyl)-ethanone,
N-(2-{3-[4-(3,4-Difluoro-phenoxy)-piperidin-1-yl]-2-hydroxy-propoxy}-phenyl)-acetamide,
3-(2-{3-[4-(3,4-Difluoro-phenoxy)-piperidin-1-yl]-2-hydroxy-propoxy}-phenyl)-propionic acid methyl ester,
2-{3-[4-(3,4-Difluoro-phenoxy)-piperidin-1-yl]-2-hydroxy-propoxy}-N,N-dimethyl-benzamide,
1-(2-{3-[4-(3,4-Difluoro-phenoxy)-piperidin-1-yl]-2-hydroxy-propoxy}-phenyl)-propan-1-one,
(2-{3-[4-(3,4-Difluoro-phenoxy)-piperidin-1-yl]-2-hydroxy-propoxy}-benzoylamino)-acetic acid methyl ester,
N-(2-{3-[3-(3,4-Difluoro-phenoxymethyl)-piperidin-1-yl]-2-hydroxy-propoxy}-phenyl)-acetamide,
N-(2-{3-[4-(4-Fluoro-phenoxy)-piperidin-1-yl]-2-hydroxy-propoxy}-phenyl)-acetamide,
3-(2-{3-[4-(4-Fluoro-phenoxy)-piperidin-1-yl]-2-hydroxy-propoxy}-phenyl)-propionic acid methyl ester,
1-(2,6-Dimethoxy-phenoxy)-3-[4-(4-fluoro-phenoxy)-piperidin-1-yl]-propan-2-ol,
1-[4-(4-Fluoro-phenoxy)-piperidin-1-yl]-3-(2-methoxy-phenoxy)-propan-2-ol,
1-(2-{3-[4-(4-Fluoro-phenoxy)-piperidin-1-yl]-2-hydroxy-propoxy}-phenyl)-ethanone,
2-{3-[4-(4-Fluoro-phenoxy)-piperidin-1-yl]-2-hydroxy-propoxy}-N,N-dimethyl-benzamide,
1-(2-{3-[4-(4-Fluoro-phenoxy)-piperidin-1-yl]-2-hydroxy-propoxy}-phenyl)-propan-1-one,
(2-{3-[4-(4-Fluoro-phenoxy)-piperidin-1-yl]-2-hydroxy-propoxy}-benzoylamino)-acetic acid methyl ester,
N-(2-{3-[3-(4-Fluoro-phenoxymethyl)-piperidin-1-yl]-2-hydroxy-propoxy}-phenyl)-acetamide,
3-(2-{3-[3-(4-Fluoro-phenoxymethyl)-piperidin-1-yl]-2-hydroxy-propoxy}-phenyl)-propionic acid methyl ester,
1-[34-Fluoro-phenoxymethyl)-piperidin-1-yl]-3-(2-methoxy-phenoxy)-propan-2-ol,
1-(2-{3-[3-(4-Fluoro-phenoxymethyl)-piperidin-1-yl]-2-hydroxy-propoxy}-phenyl)-ethanone
2-(2-{3-[3-(4-Fluoro-phenoxymethyl)-piperidin-1-yl]-2-hydroxy-propoxy}-benzoylamino)-2-methyl-propionic acid methyl ester,
2-{3-[3-(4-Fluoro-phenoxymethyl)-piperidin-1-yl]-2-hydroxy-propoxy}-N,N-dimethyl-benzamide,
1-(2-{3-[3-(4-Fluoro-phenoxymethyl)-piperidin-1-yl]-2-hydroxy-propoxy}-6-methoxy-phenyl)-ethanone,
N-(2-{3-[4-(4-Acetylamino-phenoxy)-piperidin-1-yl]-2-hydroxy-propoxy}-phenyl)-acetamide,
N-(4-{1-[3-(2-Acetyl-phenoxy)-2-hydroxy-propyl]-piperidin-4-yloxy}-phenyl)-acetamide,
N-(4-cyano-2-{3-[4-(3,4-dichloroanilino)-1-piperidinyl]-2-hydroxypropoxy}phenyl)acetamide,
3-(2-{3-[4-(4-Chloro-phenoxy)-piperidin-1-yl]-2-hydroxy-propoxy}-phenyl)-propionic acid methyl ester,
1-[4-(4-Chloro-phenoxy)-piperidin-1-yl]-3-(2-methoxy-phenoxy)-propan-2-ol,
1-(2-{3-[4-(4-Chloro-phenoxy)-piperidin-1-yl]-2-hydroxy-propoxy}-phenyl)-ethanone,
2-(2-{3-[4-(4-Chloro-phenoxy)-piperidin-1-yl]-2-hydroxy-propoxy}-benzoylamino)-2-methyl-propionic acid methyl ester,
2-3-[4-(4-Chloro-phenoxy)-piperidin-1-yl]-2-hydroxy-propoxy}-N,N-dimethyl-benzamide,
1-(2-{3-[4-(4-Chloro-phenoxy)-piperidin-1-yl]-2-hydroxy-propoxy}-6-methoxy-phenyl)-ethanone,
1-(2-{3-[4-(4-Chloro-phenoxy)-piperidin-1-yl]-2-hydroxy-propoxy}-phenyl)-propan-1-one,
(2-{3-[4-(4-Chloro-phenoxy)-piperidin-1-yl]-2-hydroxy-propoxy}-benzoylamino)-acetic acid methyl ester,
N-(2-{3-[3-(4-Chloro-phenoxymethyl)-piperidin-1-yl]-2-hydroxy-propoxy}-phenyl)-acetamide,
3-(2-{3-[3-(4-Chloro-phenoxymethyl)-piperidin-1-yl]-2-hydroxy-propoxy}-phenyl)-propionic acid methyl ester,
1-(2-{3-[3-(4-Chloro-phenoxymethyl)-piperidin-1-yl]-2-hydroxy-propoxy}-phenyl)-ethanone
2-{3-[3-(4-Chloro-phenoxymethyl)-piperidin-1-yl]-2-hydroxy-propoxy}-N,N-dimethyl-benzamide,
1-(2-{3-[3-(4-Chloro-phenoxymethyl)-piperidin-1-yl]-2-hydroxy-propoxy}-phenyl)-propan-1-one,
N-[2-({(1R,2R)-2-[4-(3,4-dichlorophenoxy)-1-piperidinyl]-1-hydroxycyclopentyl}methoxy)phenyl]acetamide,
Methyl (2S,4R)-1-{3-[2-(acetylamino)phenoxy]-2-hydroxypropyl}-4-[(4-chlorobenzyl)oxy]-2-pyrrolidinecarboxylate hydrochloride,
N-(2-{3-[4-(3,4-Dichloroanilino)-1-piperidinyl]-2-hydroxypropoxy}-4-methylphenyl)acetamide,
N-(2-{3-[4-(4-Chloroanilino)-1-piperidinyl]-2-hydroxypropoxy}phenyl)acetamide,
N-(4-Chloro-2-{3-[4-(4-chloroanilino)-1-piperidinyl]-2-hydroxypropoxy}phenyl)-acetamide
N-(2-{3-[4-(4-Chloroanilino)-1-piperidinyl]-2-hydroxypropoxy}-4-cyanophenyl)acetamide,
N-(2-{3-[4-(4-Chloroanilino)-1-piperidinyl]-2-hydroxypropoxy}-4-methylphenyl)acetamide,
N-(5-Chloro-2-{3-[4-(4-fluoroanilino)-1-piperidinyl]-2-hydroxypropoxy}phenyl)acetamide,
N-(5-Chloro-2-{3-[4-(3,4-difluoroanilino)-1-piperidinyl]-2-hydroxypropoxy}phenyl)acetamide,
N-(5-Cyano-2-{3-[4-(4-fluoroanilino)-1-piperidinyl]-2-hydroxypropoxy}-phenyl)acetamide,
N-(5-Cyano-2-{3-[4-(3,4-difluoroanilino)-1-piperidinyl]-2-hydroxypropoxy}phenyl)acetamide,
N-(2-{3-[4-(4-Fluoroanilino)-1-piperidinyl]-2-hydroxypropoxy}-4-methylphenyl)acetamide,
N-(2-{3-[4-(3,4-Difluoroanilino)-1-piperidinyl]-2-hydroxypropoxy}-4-methylphenyl)acetamide,
N-(2-{3-[3(S)-(4-Chloro-phenoxy)-pyrrolidin-1-yl]-2-(R)-hydroxy-propoxy-phenyl)acetamide,
N-(2-{3-[3S-(4-Chloro-phenoxy)-pyrrolidin-1-yl]-2S-hydroxy-propoxy}-phenyl)-acetamide hydrochloride,
N-(2-{3-[3(R)-(4-Chloro-phenoxy)-pyrrolidin-1-yl]-2-(S)-hydroxy-propoxy-phenyl)acetamide,
N-[5-Chloro-2-({(2S)-3-[(3S)-3-(4-chloro-phenoxy)pyrrolidinyl]-2-hydroxypropyl}oxy)phenyl]acetamide,
N-[5-Chloro-2-({(2R)-3-[(3R)-3-(4-chloro-phenoxy)pyrrolidinyl]-2-hydroxypropyl}oxy)phenyl]acetamide,
N-[5-Chloro-2-({(2S)-3-[(3R)-3-(4-chloro-phenoxy)pyrrolidinyl])-2-hydroxypropyl}oxy)phenyl]acetamide,
N-[5-Chloro-2-({(2R)-3-[(3S)-3-(4-chloro-phenoxy)pyrrolidinyl]-2-hydroxypropyl}oxy)phenyl]acetamide, N-(2-{3-[3-(4-Chloro-phenoxy)-pyrrolidin-1-yl]-2-hydroxy-propoxy}-4,5-difluoro-phenyl)-acetamide,
N-{5-Chloro-2-[2-hydroxy-3-(3-phenoxy-pyrrolidin-1-yl)-propoxy]-phenyl}-acetamide,
N-(5-Chloro-2-{2-hydroxy-3-[3-(4-nitro-phenoxy)-pyrrolidin-1-yl]-propoxy}-phenyl)-acetamide,
N-(5-Acetyl-2-{3-[3-(3,4-dichloro-phenoxy)-pyrrolidin-1-yl]-2-hydroxy-propoxy}-phenyl)-acetamide,
4-Acetylamino-3-{3-[3-(3,4-dichloro-phenoxy)-pyrrolidin-1-yl]-2-hydroxy-propoxy}-benzoic acid methyl ester,
N-(3-{3-[3-(3,4-Dichloro-phenoxy)-pyrrolidin-1-yl]-2-hydroxy-propoxy}-naphthalen-2-yl)-acetamide,
N-(2-{3-[3-(4-Chloro-phenoxy)-pyrrolidin-1-yl]-2-hydroxy-propoxy}-5-cyano-phenyl)-acetamide,
4-Acetylamino-3-{3-[3-(4-chloro-phenoxy)-pyrrolidin-1-yl]-2-hydroxy-propoxy}-benzoic acid methyl ester,
N-(3-{3-[3-(4-Chloro-phenoxy)-pyrolidin-1-yl]-2-hydroxy-propoxy}-naphthalen-2-yl)-acetamide,
N-(5-Cyano-2-{3-[4-(3,4-dichloro-phenoxy)-piperidin-1-yl]-2-hydroxy-propoxy}-phenyl)-acetamide,
N-(2-{3-[4-(3,4-Dichloro-phenoxy)-piperidin-1-yl]-2-hydroxy-propoxy}-5-trifluoromethyl-phenyl)-acetamide,
N-(5-Chloro-2-{3-[3-(4-fluoro-phenoxy)-pyrrolidin-1-yl]-2-hydroxy-propoxy}-phenyl)-acetamide trifluoroacetate,
N-(5-Acetyl-2-{3-[3-(4-chloro-phenoxy)-pyrrolidin-1-yl]-2-hydroxy-propoxy}-phenyl)-acetamide trifluoroacetate,
N-(2-{3-[3-(4-Chlorophenoxy)-1-pyrrolidinyl]-2-hydroxypropoxy}phenyl)-methanesulfonamide,
N-(5-Chloro-2-[3-[3,4-dichlorophenoxy)-1-pyrrodinyl]-2-hydroxypropoxy]-phenyl)urea,
1-(3-{2-[(Aminocarbonyl)amino]phenoxy}-2-hydroxypropyl)-3-(4-chlorophenoxy)pyrrolidinium 2,2,2-trifluoroacetate,
1-(3-{2-[(Aminocarbonyl)amino]phenoxy}-2-hydroxypropyl)-3-(3,4-dichlorophenoxy)pyrrolidinium 2,2,2-trifluoroacetate,
1-(3-{2-[(Aminocarbonyl)amino]chlorophenoxy}-2-hydroxypropyl)-3-(4-chlorophenoxy)pyrrolidinium 2,2,2-trifluoroacetate,
N-(2-{3-[3-(4-Chlorophenoxy)-1-pyrrolidinyl]-2-hydroxypropoxy}phenyl)-N'-ethylurea hydrochloride,
N-(2-{3-[3-(4-Chlorophenoxy)-1-pyrrolidinyl]-2-hydroxypropoxy}phenyl)-N'-methylurea hydrochloride,
(2S,4S)-1-{3-[2-(Acetylamino)phenoxy]-2-hydroxypropyl}-4-(4-chlorophenoxy)-2-pyrrolidinecarboxylic acid; compound with trifluoroacetic acid,
Ethyl (2S,4S)-1-{3-[2-(acetylamino)phenoxy]-2-hydroxypropyl}-4-(3,4-dichlorophenoxy)-2-pyrrolidinecarboxylate; trifluoroacetic acid salt,
N-[2-({(2S)-3-[(2S,4S)-4-(4-Chlorophenoxy)-2-(hydroxymethyl)pyrrolidinyl]-2-hydroxypropyl}oxy)phenyl]acetamide; trifluoroacetic acid salt,
N-[2-({(2R)-3-[(2,4S)-4-(4-Chlorophenoxy)-2-(hydroxymethyl)pyrrolidinyl]-2-hydroxypropyl}oxy)phenyl]acetamide; trifluoroacetic acid salt,
N-(2-{3-[3-(4-Chlorophenoxy)-1-pyrrolidinyl]-2-hydroxy-2-methylpropoxyphenyl)acetamide hydrochloride,
N-(2-{(1S*,2R*,3S*)-3-[3-(4-Chloro-phenoxy)-pyrrolidin-1-yl]-2-hydroxy-cyclopentyloxy}-phenyl)-acetamide,
N-(2-{(1R*,2R*,3*)-3-[3-(4-Chloro-phenoxy)-pyrrolidin-1-yl]-2-hydroxy-cyclopentyloxy}-phenyl)-acetamide,
N-(2-{(2R*,3R*)-3-[4-(3,4-Dichloro-phenoxy)-piperidin-1-yl]-2-hydroxy-butoxy}-phenyl)-acetamide,
N-(2-{(1S*,2R*,3S*)-3-(4-(4-Chloro-phenoxy)-piperidin-1-yl]-2-hydroxy-cyclopentyloxy}-phenyl)-acetamide,
N-(2-{(2R*,3S*)-3-[4-(3,4-Dichloro-phenoxy)-piperidin-1-yl]-2-hydroxy-butoxy}-phenyl)-acetamide,
N-(2-{(2R*,3R*)-3-[3-(4-Chloro-phenoxy)-pyrrolidin-1-yl]-2-hydroxy-butoxy}-phenyl)-acetamide,
N-(2-{(2R*,3S*)-3-[3-(4-Chloro-phenoxy)-pyrrolidin-1-yl]-2-hydroxy-butoxy}-phenyl)-acetamide,
N-(2-{(1S*,2R*,3S*)-3-[4-(3-Chloro-phenoxy)-piperidin-1-yl]-2-hydroxy-cyclopentyloxy}-phenyl)-acetamide,
N-[5-Chloro-2-({(1S,2R,3S)*-3-[4-(3,4-dichlorophenoxy)-1-piperidinyl]-2-hydroxycyclopentyl}oxy)phenyl]acetamide,
N-[4-Fluoro-2-({(1S,2R,3S)*-3-[4-(3,4-dichlorophenoxy)-1-piperidinyl]-2-hydroxycyclopentyl}oxy)phenyl]acetamide,
N-(2-{3-[4-(3,4-Dichlorobenzyl)-1-piperazinyl]-2-hydroxypropoxy}-phenyl)acetamide dihydrochloride,
N-(2-{3-[4-(3,4-Dichlorobenzyl)-1-piperazinyl]-2-hydroxypropoxy}-4-fluorophenyl)acetamide,
N-(2-{3-[4-(3,4-Dichlorobenzyl)-2,5-dimethyl-1-piperazinyl]-2-hydroxypropoxy}phenyl)acetamide,
N-(5-Chloro-2-{3-[4-(3,4-dichlorobenzyl)-1-piperazinyl]-2-hydroxypropoxy}phenyl)acetamide,
N-(5-Chloro-2-{3-[4-(3,4-dichlorobenzyl)-2,5-dimethyl-1-piperazinyl]-2-hydroxypropoxy}phenyl)acetamide,
N-(2-{3-[4-(3,4-Dichlorobenzyl)-2,5-dimethyl-1-piperazinyl]-2-hydroxypropoxy}-4methylphenyl)acetamide,
N-(2-{3-[4-(3,4-Dichlorobenzyl)-2,5-dimethyl-1-piperazinyl]-2-hydroxypropoxy}-4fluorophenyl)acetamide,
N-(2-{3-[(S*R*)-4-(3,4-Dichlorobenzyl)-2,5-dimethyl-1-piperazinyl]-2-hydroxypropoxy}phenyl)acetamide,
N-(2-{3-[(S*R*)-4-(4-Chlorobenzyl)-2,5-dimethyl-1-piperazinyl]-2-hydroxypropoxy}phenyl)acetamide,
N-(5-Chloro-2-{3-[(S*R*)-4-(3,4-dichlorobenzyl)-2,5-dimethylpiperazinyl]-2-hydroxypropoxy}phenyl)acetamide,
N-(5-Chloro-2-{3-[(S*R*)-4-(4-chlorobenzyl)-2,5-dimethylpiperazinyl]-2-hydroxypropoxy}phenyl)acetamide,
1-(5-Chloro-2-{3-[4-(4-chlorobenzoyl)-1-piperazinyl]-2-hydroxypropoxy}phenyl)-1-ethanone,
N-(5-Cyano-2-{3-[(S*R*)-4-(3,4-dichlorobenzyl)-2,5-dimethylpiperazinyl]-2-hydroxypropoxy}phenyl)acetamide,
N-(2-{3-[(S*R*)-4-(4-Chlorobenzyl)-2,5-dimethylpiperazinyl]-2-hydroxypropoxy}-5-cyanophenyl)acetamide,
N-(5-Chloro-2-3-[4-(4-chlorobenzyl)-1-piperazinyl]-2-hydroxypropoxy}-phenyl)acetamide,
N-(4-Chloro-2-{3-[4-(4-chlorobenzyl)-2,5-dimethyl-1-piperazinyl]-2-hydroxypropoxy}phenyl)acetamide,
N-(2-{3-[4-(4-Chlorobenzoyl)-1-piperazinyl]-2-hydroxypropoxy}-5-cyanophenyl)acetamide,
N-(2-{3-[4-(4-Chlorobenzoyl)-1-piperazinyl]-2-hydroxypropoxy}-4-methylphenyl)acetamide,
N-[5-Chloro-2-({(1R,2S,3R)-3-[(3S)-3-(4-chlorophenoxy)pyrrolidinyl]-2-hydroxycyclopentyl}oxy)phenyl]acetamide,
N-{2-[(2S)-(3-{(3S)-3-[(4-Chlorophenyl)oxy]-1-pyrrolidinyl}-2-hydroxypropyl)oxy]-4-fluorophenyl}-acetamide,
N-[2-({(2S)-3-[(3S)-3-(4-Chlorobenzyl)pyrrolidinyl]-2-hydroxypropyl}oxy)phenyl]acetamide hydrochloride,
N-(5-Chloro-2-{3-[3-(4-chloro-benzyl)-pyrrolidin-1-yl]-2-hydroxy-propoxy}phenyl)-acetamide trifluoroacetic acid salt,
N-(2-{3-[3-(4-Chlorophenoxy)-1-pyrrolidinyl]-2-hydroxypropoxy}-4-methylphenyl)-1-pyrrolidinecarboxamide trifluoroacetate, N-(2-{3-[3-(4-Chlorophenoxy)-1-pyrrolidinyl]-2-hydroxypropoxy}-4-hydroxyphenyl)acetamide trifluoroacetate,
N-[2-({(2S)-3-[4-(3,4-Dichlorophenoxy)-1-piperidinyl]-2-hydroxypropyl}oxy)-4-fluorophenyl]acetamide trifluoroacetic acid salt,
N-(2-(3-(4-Chloro-phenoxy)-pyrrolidin-1-yl)-2-hydroxy-propoxy)-4,6-difluoro-phenyl)-acetamide hydrochloride,
N-[2-({(2S)-3-[(2S,4S)-4-(4-Chlorophenoxy)-2-methylpyrrolidinyl]-2-hydroxypropyl}oxy)-4-fluorophenyl]acetamide trifluoroacetic acid salt,
N-[2-({(2S)-3-[(3R)-3-(4-Chlorobenzyl)pyrrolidinyl]-2-hydroxypropyl}oxy)phenyl]acetamide hydrochloride,
N-{2-[(2R)-(3-{(3S)-3-[(4-Chlorophenyl)oxy]-1-pyrrolidinyl}-2-hydroxypropyl)oxy]-4-fluorophenyl}-acetamide,
N-[2-({(2S)-3-[(2R,4S)-4-(4-Chlorophenoxy)-2-methylpyrrolidinyl]-2-hydroxypropyl}oxy) phenyl]acetamide trifluoroacetic acid salt,
N-{2-[(2S)-(3-{(3R)-3-[(4-Chlorophenyl)oxy]-1-pyrrolidinyl}-2-hydroxypropyl)oxy]-4-fluorophenyl}-acetamide,
N'-(2-{3-[3-(4-Chlorophenoxy)-1-pyrrolidinyl]-2-hydroxypropoxy}-4-methylphenyl)-N,N-dimethylurea trifluoroacetate,
N-(2-{3-[3-(4-Chloroanilino)-1-pyrrolidinyl]-2-hydroxypropoxy}phenyl)acetamide,
N-{2-[(3-{3-[(4-Chlorophenyl)oxy]-1-pyrrolidinyl}-2-hydroxy-1-methylpropyl)oxy]phenyl}acetamide hydrochloride,
N-(2-{3-[3-(4-Chlorophenoxy)-1-pyrrolidinyl]-2-hydroxypropoxy}-4-methoxyphenyl)acetamide hydrochloride,
N-2-[3-(4-Chloro-benzyloxy)-pyrrolidin-1-yl]-2-hydroxy-propoxy)-phenyl)-acetamide trifluoroacetic acid salt,
N-(2-{3-[3-(4-Chloro-phenoxy)-pyrrolidin-1-yl]-2-hydroxy-2-methyl-propoxy}-phenyl)-acetamide,
N-(2-{(1S,2R,3S)-3-[(3S-3-(3,4-Difluoro-phenoxy)-pyrrolidin-1-yl]-2-hydroxy-cyclopentyloxy}-5-chlorophenyl)-acetamide (diastereomeric mixture),
N-[2-({(2R,3S)*-3-[(3S)-3-(4-Chlorophenoxy)pyrrolidinyl]-2-hydroxybutyl}oxy)-4-methylphenyl]acetamide (diastereomeric mixture),
N-{2-[(3-{4-[(3,4-Dichlorophenyl)oxy]-1-piperidinyl}-2-hydroxy-2-methylpropyl)oxy]-4-fluorophenyl}acetamide hydrochloride,
N-(2-{(1S,2R,3S)*-3-[(3S-3-(4-Chloro-phenoxy)-pyrrolidin-1-yl]-2-hydroxy-cyclopentyloxy}-4-fluoro-phenyl)-acetamide (diastereomeric mixture),
N-(5-Chloro-2-{3-[3-(3,4-difluoro-phenoxy)-pyrrolidin-1-yl]-2-hydroxy-propoxy}-phenyl)-acetamide,
N-(5-Chloro-2-{3-[3-(4-fluoro-phenoxy)-pyrrolidin-1-yl]-2-hydroxy-propoxy}-phenyl)-acetamide,
N-(4-Cyano-2-{3-[4-(3,4-dichloroanilino)-1-piperidinyl]-2-hydroxypropoxy}phenyl)acetamide,
N-(4-Hydroxy-2-{(1S,2R,3S)*-3-[(3S)-3-(4-chlorophenoxy)-pyrrolidin-1-yl]-2-hydroxy-cyclopentyloxy}-phenyl)-acetamide (diastereomeric mixture),
N-(4-Hydroxy-2-{(1S,2R,3S)-3-[(3S)-3-(4-chlorophenoxy)-pyrrolidin-1-yl]-2-hydroxy-cyclopentyloxy}-phenyl)-acetamide,
N-(4-Hydroxy-2-{(1R,2S,3R)-3-[(3S)-3-(4-chlorophenoxy)-pyrrolidin-1-yl]-2-hydroxy-cyclopentyloxy}-phenyl)-acetamide,
N-[2-({(1S,2R,3S)-3-[(3S)-3-(4-Chlorophenoxy)pyrrolidinyl]-2-hydroxycyclopentyl}oxy)phenyl]acetamide,
N-[2-({(1R,2S,3R)-3-[(3S)-3-(4-Chlorophenoxy)pyrrolidinyl]-2-hydroxycyclopentyl}oxy)phenyl]acetamide,
N-[5-Chloro-2-({(1S,2R,3S)-3-[(3S)-3-(4-chlorophenoxy)pyrrolidinyl]-2-hydroxycyclopentyl}oxy)phenyl]acetamide,
N-{5-Chloro-2-[((1S,2R,3S)*-3-{[1-(4-chlorobenzyl)-4-piperidinyl]amino}-2-hydroxycyclopentyl)oxy]phenyl}acetamide (racemic mixture), and
N-[2-({(2S)-3-[(3S)-3-(4-Chlorophenoxy)pyrrolidinyl]-2-hydroxypropyl}oxy)-4-hydroxyphenyl]acetamide.

The present invention further provides a process for the preparation of a compound of formula (I) as defined above which comprises, (a) reacting a compound of general formula:

wherein R is as defined in formula (I), with a compound of general formula:

wherein Q, $R^2$, $R^4$, $R^5$, $R^6$, $R^7$ and $R^8$ are as defined in formula (I); or (b) reacting a compound of general formula:

wherein R, $R^4$, $R^5$, $R^6$, $R^7$ and $R^8$ are as defined in formula (I), with a compound of general formula:

wherein $L^1$ represents a hydrogen atom or an activating group (e.g. Li when Q is $CH_2$) and Q and $R^2$ are as defined in formula (I);

and optionally thereafter converting the compound of formula (I) to a further compound of formula (I); and, if desired, forming a pharmaceutically acceptable salt or solvate of the compound of formula (I).

In one aspect, the invention provides a process for the preparation of a compound of formula (I') as hereinbefore defined which comprises, (a) reacting a compound of general formula:

wherein R is as defined in formula (I'), with a compound of general formula:

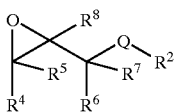

(III')

wherein Q, $R^2$, $R^4$, $R^5$, $R^6$, $R^7$ and $R^8$ are as defined in formula (I'); or (b) reacting a compound of general formula:

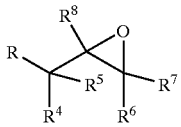

(IV')

wherein R, $R^4$, $R^5$, $R^6$, $R^7$ and $R^8$ are as defined in formula (I'), with a compound of general formula:

   (V')

wherein $L^1$ represents a hydrogen atom or an activating group (e.g. Li when Q is $CH_2$) and Q and $R^2$ are as defined in formula (I');

and optionally thereafter converting the compound of formula (I') to a further compound of formula (I'); and, if desired, forming a pharmaceutically acceptable salt or solvate of the compound of formula (I').

In another aspect, the invention provides a process for the preparation of a compound of formula (I") as hereinbefore defined which comprises, (a) reacting a compound of general formula:

R—H   (V")

wherein R is as defined in formula (I"), with a compound of general formula:

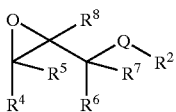

(III")

wherein Q, $R^2$, $R^4$, $R^5$, $R^6$, $R^7$ and $R^8$ are as defined in formula (I"); or (b) reacting a compound of general formula:

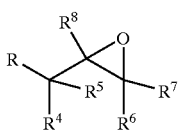

(IV")

wherein R, $R^4$, $R^5$, $R^6$, $R^7$ and $R^8$ are as defined in formula (I"), with a compound of general formula:

   (V")

wherein $L^1$ represents a hydrogen atom or an activating group (e.g. Li when Q is $CH_2$) and Q and $R^2$ are as defined in formula (I");

and optionally thereafter converting the compound of formula (I") to a further compound of formula (I"); and, if desired, forming a pharmaceutically acceptable salt or solvate of the compound of formula (I").

In yet another aspect, the invention provides a process for the preparation of a compound of formula (I''') as hereinbefore defined which comprises, (a) reacting a compound of general formula:

R—H   (II''')

wherein R is as defined in formula (I'''), with a compound of general formula:

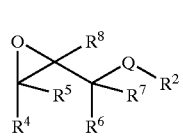

(III''')

wherein Q, $R^2$, $R^4$, $R^5$, $R^6$, $R^7$ and $R^8$ are as defined in formula (I'''); or (b) reacting a compound of general formula:

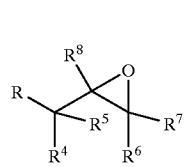

(IV''')

wherein R, $R^4$, $R^5$, $R^6$, $R^7$ and $R^8$ are as defined in formula (I'''), with a compound of general formula:

   (V''')

wherein $L^1$ represents a hydrogen atom or an activating group (e.g. Li when Q is $CH_2$) and Q and $R^2$ are as defined in formula (I''');

and optionally thereafter converting the compound of formula (I''') to a further compound of formula (I'''); and, if desired, forming a pharmaceutically acceptable salt or solvate of the compound of formula (I''').

The processes of the invention may conveniently be carried out in a solvent, e.g. an organic solvent such as an alcohol (e.g. methanol or ethanol), a hydrocarbon (e.g. toluene) or acetonitrile at a temperature of, for example, 15° C. or above such as a temperature in the range from 20 to 120° C.

Compounds of formulae (II), (II'), (II"), (II'''), (III), (III'), (III"), (III'''), (IV), (IV'), (IV"), (IV'''), (V), (V'), (V") and (V''') are either commercially available, are well known in the literature or may be prepared easily using known techniques.

Compounds of formula (I), (I'), (I") or (I''') can be converted into further compounds of formula (I), (I'), (I") or (I''') using standard procedures. For example, a compound of formula (I) in which $R^{15}$ represents —NHC(O)$CH_3$ can be converted to a further compound of formula (I) in which $R^{15}$ represents —$NH_2$ by a hydrolysis reaction in the presence of hydrochloric acid.

It will be appreciated by those skilled in the art that in the processes of the present invention certain functional groups such as hydroxyl or amino groups in the starting reagents or intermediate compounds may need to be protected by protecting groups. Thus, the preparation of the compounds of formula (I), (I'), (I") or (I'") may involve, at an appropriate stage, the removal of one or more protecting groups.

The protection and deprotection of functional groups is described in 'Protective Groups in Organic Chemistry', edited by J. W. F. McOmie, Plenum Press (1973) and 'Protective Groups in Organic Synthesis', 2nd edition, T. W. Greene and P. G. M. Wuts, Wiley-Interscience (1991).

The compounds of formula (I), (I'), (I") or (I'") above may be converted to a pharmaceutically acceptable salt or solvate thereof, preferably an acid addition salt such as a hydrochloride, hydrobromide, phosphate, acetate, fumarate, maleate, tartrate, citrate, oxalate, methanesulphonate or p-toluenesulphonate.

Compounds of formula (I), (I'), (I") or (I'") are capable of existing in stereoisomeric forms. It will be understood that the invention encompasses the use of all geometric and optical isomers of the compounds of formula (I), (I'), (I") or (I'") and mixtures thereof including racemates. The use of tautomers and mixtures thereof also form an aspect of the present invention Enantiomerically pure forms are particularly desired.

The compounds of formula (I), (I'), (I") or (I'") have activity as pharmaceuticals, in particular as modulators of chemokine receptor (especially MIP-1α chemokine receptor) activity, and may be used in the treatment of autoimmune, inflammatory, proliferative and hyperproliferative diseases and immunologically-mediated diseases including rejection of transplanted organs or tissues and Acquired Immunodeficiency Syndrome (AIDS).

Examples of these conditions are:
(1) (the respiratory tract) airways diseases including chronic obstructive pulmonary disease (COPD) such as irreversible–COPD; asthma, such as bronchial, allergic, intrinsic, extrinsic and dust asthma, particularly chronic or inveterate asthma (e.g. late asthma and airways hyperresponsiveness); bronchitis; acute, allergic, atrophic rhinitis and chronic rhinitis including rhinitis caseosa, hypertrophic rhinitis, rhinitis purulenta, rhinitis sicca and rhinitis medicamentosa; membranous rhinitis including croupous, fibrinous and pseudomembranous rhinitis and scrofoulous rhinitis; seasonal rhinitis including rhinitis nervosa (hay fever) and vasomotor rhinitis; sarcoidosis, farmer's lung and related diseases, fibroid lung and idiopathic interstitial pneumonia;
(2) (bone and joints) rheumatoid arthritis, seronegative spondyloarthropathies (including ankylosing spondylitis, psoriatic arthritis and Reiter's disease), Behcet's disease, Sjogren's syndrome and systemic sclerosis;
(3) (skin) psoriasis, atopical dermatitis, contact dermatitis and other eczmatous dermitides, seborrhoetic dermatitis, Lichen planus, Pemphigus, bullous Pemphigus, Epidermolysis bullosa, urticaria, angiodermas, vasculitides, erythemas, cutaneous eosinophilias, uveitis, Alopecia areata and vernal conjunctivitis;
(4) (gastrointestinal tract) Coeliac disease, proctitis, eosinopilic gastro-enteritis, mastocytosis, Crohn's disease, ulcerative colitis, food-related allergies which have effects remote from the gut, e.g., migraine, rhinitis and eczema;
(5) (other tissues and systemic disease) multiple sclerosis, atherosclerosis, Acquired Immunodeficiency Syndrome (AIDS), lupus erythematosus, systemic lupus, erythematosus, Hashimoto's thyroiditis, myasthenia gravis, type I diabetes, nepbrotic syndrome, eosinophilia fascitis, hyper IgE syndrome, lepromatous leprosy, seary syndrome and idiopathic thrombocytopenia pupura;
(6) (allograft rejection) acute and chronic following, for example, transplantation of kidney, heart, liver, lung, bone marrow, skin and cornea; and chronic graft versus host disease;
(7) cancers, especially non-small cell lung cancer (NSCLC) and squamous sarcoma;
(8) diseases in which angiogenesis is associated with raised CXCR2 chemokine levels (e.g. NSCLC); and
(9) cystic fibrosis, stroke, re-perfusion injury in the heart, brain, peripheral limbs and sepsis.

Thus, the present invention provides a compound of formula (I), (I'), (I") or (I'"), or a pharmaceutically-acceptable salt or solvate thereof, as hereinbefore defined for use in therapy.

In a further aspect, the present invention provides the use of a compound of formula (I), (I'), (I") or (I'"), or a pharmaceutically acceptable salt or solvate thereof, as hereinbefore defined in the manufacture of a medicament for use in therapy.

In the context of the present specification, the term "therapy" also includes "prophylaxis" unless there are specific indications to the contrary. The terms "therapeutic" and "therapeutically" should be construed accordingly.

The invention also provides a method of treating an inflammatory disease in a patient suffering from, or at risk of; said disease, which comprises administering to the patient a therapeutically effective amount of a compound of formula (I), (I'), (I") or (I'"), or a pharmaceutically acceptable salt or solvate thereof, as hereinbefore defined, The invention still further provides a method of treating an airways disease in a patient suffering from, or at risk of, said disease, which comprises administering to the patient a therapeutically effective amount of a compound of formula (I), (I'), (I") or (I'"), or a pharmaceutically acceptable salt or solvate thereof, as hereinbefore defined.

For the above-mentioned therapeutic uses the dosage administered will, of course, vary with the compound employed, the mode of administration, the treatment desired and the disorder indicated. The daily dosage of the compound of formula (I), (I'), (I") or (I'") may be in the range from 0.001 mg/kg to 30 mg/kg.

The compounds of formula (I), (I'), (I") or (I'") and pharmaceutically acceptable salts and solvates thereof may be used on their own but will generally be administered in the form of a pharmaceutical composition in which the formula (I), (I'), (I") or (I'") compound/salt/solvate (active ingredient) is in association with a pharmaceutically acceptable adjuvant, diluent or carrier. Depending on the mode of administration, the pharmaceutical composition will preferably comprise from 0.05 to 99% w (percent by weight), more preferably from 0.05 to 80% w, still more preferably from 0.10 to 70% w, and even more preferably from 0.10 to 50% w, of active ingredient, all percentages by weight being based on total composition.

The present invention also provides a pharmaceutical composition comprising a compound of formula (I), (I'), (I") or (I'"), or a pharmaceutically acceptable salt or solvate thereof, as hereinbefore defined, in association with a pharmaceutically acceptable adjuvant, diluent or carrier.

The invention further provides a process for the preparation of a pharmaceutical composition of the invention which comprises mixing a compound of formula (I), (I'), (I") or (I'"), or a pharmaceutically acceptable salt or solvate thereof, as hereinbefore defined, with a pharmaceutically acceptable adjuvant, diluent or carrier.

The pharmaceutical compositions may be administered topically (e.g. to the lung and/or airways or to the skin) in the form of solutions, suspensions, heptafluoroalkane aerosols and dry powder formulations; or systemically, e.g. by oral administration in the form of tablets, capsules, syrups, powders or granules, or by parenteral administration in the form of solutions or suspensions, or by subcutaneous administration or by rectal administration in the form of suppositories or transdermally.

The invention will now be further explained by reference to the following illustrative examples, in which $^1$H NMR spectra were recorded on Varian Unity Inova 400. The is central solvent peak of chloroform-d ($\delta_H$ 7.27 ppm) were used as internal standard. Low resolution mass spectra and accurate mass determination were recorded on a Hewlett-Packard 1100 LC-MS system equipped with APCI/ESI ionisation chambers. All solvents and commercial reagents were laboratory grade and used as received. The nomenclature used for the compounds was generated with ACD/IUPAC Name Pro.

EXAMPLE 1

N-(2-{3-[3R,S-(4-Chloro-phenoxy)-pyrrolidin-1-yl]-2R,S-hydroxy-propoxy}-phenyl)-acetamide hydrochloride (i) 3-Hydroxy-pyrrolidine-1-carboxylic acid tert-butyl ester A solution of pyrrolidin-3-ol (16.25 g, 186.5 mmol) and di-tert-butyl-dicarbonate (40.7 g, 186.5 mmol) in dry THF (50 ml) under nitrogen was stirred over night. Concentration at reduced pressure and purification by flash chromatography on silica (EtOAc:heptane, 7:3) gave 31.9 g (91%) of the subtitle compound.

$^1$H-NMR (400 MHz, DMSO-d6): δ 4.87 (d, 1H, J=3.4 Hz), 4.21 (bs, 1H), 3.31–3.22 (m, 3H), 3.10 (d, 1H, J=11.5 Hz), 1.83 (m, 1H), 1.72 (m, 1H), 1.39 (s, 9H).

APCI-MS: m/z 132 [MH$^+$-56]

(ii) 3-(4-Chloro-phenoxy)-pyrrolidine

3-Hydroxy-pyrrolidine-1-carboxylic acid tert butyl ester (2.1 g, 9.9 mmol) and triphenyl phosphine (2.59 g, 9.9 mmol) were dissolved in dry THF (35 ml) under nitrogen. The solution was cooled to 0° C. and 4-chlorophenol (1.28 g, 9.9 mmol) dissolved in dry THF (10 ml) was added followed by diethyl azodicarboxylate (DEAD) (1.55 ml, 9.9 mmol). After 15 minutes the ice bath was removed and the reaction was stirred overnight The reaction mixture was concentrated under reduced pressure and the residue was stirred with ether. The solid triphenyl phosphine oxide was filtered off. The solution was washed three times with sodium hydroxide (1M) and concentrated. The BOC-protected product was purified by flash chromatography on silica using EtOAc/heptane as eluant. It was dissolved in dichloromethane (35 ml) and trifluoroacetic acid (17 ml). The reaction mixture was stirred at room temperature overnight, concentrated and purified by flash chromatography on silica (MeOH:CHCl$_3$:NH$_3$, 100:100:1) to give the subtitle compound (1.72 g, 88%).

$^1$H-NMR (400 MHz, DMSO-d6): δ 7.30 (d, 2H, J=8.9 Hz), 6.91 (d, 2H, J=8.9 Hz), 4.83 (m, 1H), 3.03 (dd, 1H, J=12.3, 5.4 Hz), 2.82 (m, 3H), 1.99 (m, 1H), 1.72 (m, 1H).

APCI-MS: m/z 198 [MH$^+$]

(iii) N-(2-{3-[3R,S-(4-Chloro-phenoxy)-pyrrolidin-1-yl]-2R,S-hydroxy-propoxy}-phenyl)-acetamide hydrochloride A solution of 3-(4-Chloro-phenoxy)-pyrrolidine (0.059 g, 0.298 mmol) and N-acetyl-2-(2,3-epoxypropoxy)aniline (0.062 g, 0.299 mmol) in EtOH (1.5 ml, 99.5%) was stirred for 3 hours at 75° C. in a sealed vial. The solvent was evaporated after completion of the reaction and the residue was purified on silica (CH$_2$Cl$_2$:MeOH, 98:2 to 97:3) to give 88 mg of the free amine of the title compound. The amine was dissolved in MeOH:water 1:1 (30 ml), and the solution was acidified with 2M hydrochloric acid. The methanol was evaporated and the residual water solution was lyophilized to give 92 mg (70%) of the title compound as a white solid.

APCI-MS: m/z 405.2, 407.2 [MH$^+$, isotope pattern]

EXAMPLE 2

N-(5-Chloro-2-{3-[3R,S-(4-Chloro-phenoxy)-pyrrolidin-1-yl]-2R,S-hydroxy-propoxy}-phenyl)-acetamide hydrochloride (i) N-(5-Chloro-2-hydroxy-phenyl)acetamide A solution of 4-amino-2-chlorophenol (2.0 g, 13.9 mmol) and acetic anhydride (1.77 g, 17.3 mmol) in water (40 ml) was stirred vigorously for 5 minutes. The reaction mixture was then heated with stirring to 60° C. for 30 minutes, and was then allowed to cool. A pink solid was formed and the precipitate was collected by filtration, washed twice with water, and dried to give 1.8 g (70%) of the subtitle compound.

$^1$H-NMR (400 MHz, DMSO-d$_6$): δ 10.09 (1H, s); 9.25 (1H, bs); 7.93 (1H, s); 6.93 (1H, dd, J 8.8, 2.7 Hz); 6.84 (1H, d, J 8.6 Hz); 2.09 (3H, s)

APCI-MS: m/z 186.0 [MH$^+$]

(ii) N-(5-Chloro-2-oxiranylmethoxy-phenyl)-acetamide

A solution of N-(5-Chloro-2-hydroxy-phenyl)-acetamide (0.499 g, 2.68 mmol), K$_2$CO$_3$ (0.60 g, 4.35 mmol) and epibromohydrin (0.405 g, 2.95 mmol) in DMF (5 ml) was heated with stirring at 50° C. for 2 hours. The mixture was then partitioned between EtOAc and water 40+40 ml. The organic phase was washed twice with water and once with brine and finally concentrated in vacuo to give a crude product. The crude product was purified on silica (heptane:EtOAc, 1:1), to give 0.43 g (66%) of a white solid.

$^1$H-NMR (400 MHz, CDCl$_3$): δ 8.46 (1H, d, J 2.3 Hz); 7.90 (1H, bs); 6.98 (1H, dd, J 8.7, 2.4 Hz); 6.83 (1H, d, J 8.8 Hz); 4.36 (1H, dd, J 11.5, 2.4 Hz); 3.94 (1H, dd, J 11.6, 6.0 Hz); 3.41–3.36 (1H, m); 2.97 (1H, dd, J 4.7, 4.2 Hz); 2.80 (1H, dd, J 4.6, 2.6 Hz); 2.23 (3H, s)

(iii) N-(5-Chloro-2-{3-[3R,S-(4-Chloro-phenoxy)-pyrrolidin-1-yl]-2R,S-hydroxy -propoxy}-phenyl)-acetamide hydrochloride Prepared by a process analogous to that described in Example 1, step (iii).

EXAMPLE 3

N-(2-{3-[4(3,4-dichlorophenoxy)-1-piperidinyl]-2-hydroxypropoxy}phenyl)-acetamide Prepared according to the methods described in Example 1. Purified and isolated as the free amine in 73% yield by C$_{18}$-column chromatography (H$_2$O:CH$_3$CN, 0.1M NH$_4$OAc buffer, gradient 30% to 95% CH$_3$CN).

APCI-MS m/z: 453, 455 [MH$^+$]

$^1$H NMR (400 MHz, CDCl$_3$): δ 7.32(d, 1H), 7.01(d, 1H), 6.85–8.80(m, 2H), 6.78–6.69 (m, 3H), 4.31 (m, 1H), 4.15–4.09(m, 1H), 4.18–3.18(bs, 3H), 2.91(m, 1H), 2.71(m, 1H), 2.62–2.52(m, 3H), 2.35(m, 1H), 2.05–1.93(m, 2H), 1.89–1.77(m, 2H)

EXAMPLE 4

1-(2-aminophenoxy)-3-[4-(3,4-dichlorophenoxy)-1-piperidinyl]-2-propanol dihydrochloride N-(2-{3-[4-(3,4-dichlorophenoxy)-1-piperidinyl]-2-hydroxypropoxy}phenyl)acetamide (1.418 g, 3.13 mmol) was dissolved in 50 ml HCl (35%/aq, puriss) and refluxed overnight The product precipitated and was filtered and dried to give 0.835 g (65%) of the title compound.

APCI-MS m/z: 411, 413 [MH$^+$]

$^1$H NMR (400 MHz, CDCl$_3$): δ 8.39–3.31 (m, 2H), 7.31(d, 1H), 7.01–6.98(m, 3H), 6.94–6.91(m, 1H), 6.75(dd, 1H), 4.31(m, 1H), 4.12–4.02 (m, 2H), 3.92(dd, 1H), 2.90(m, 1H), 2.69(m, 1H), 2.62–2.51(m, 2H), 2.46(dd, 1H), 2.34(m, 1H), 2.18(s, 3H), 2.04–1.93(m, 2H), 1.89–1.77(m, 2H).

EXAMPLE 5

N-(2-{3-[3-(3,4-dichlorophenoxy)-1-pyrrolidinyl)-2-hydroxypropoxy}phenyl)-acetamide hydrochloride Prepared according to the methods described in Example 1 to give 68 mg (68%) of the title compound as a white solid.

APCI-MS m/z: 439, 441 [MH$^+$]

EXAMPLE 6

2-{3-[4-(4-Fluoro-phenoxy)-piperidin-1-yl]-2-hydroxy-propoxy}-benzoic acid methyl ester (i) 2-Oxiranylmethoxy-benzoic acid methyl ester Prepared according to the method described in Example 2, step (ii).

$^1$H-NMR: (400 MHz, CDCl$_3$): δ 7.81 (1H, dd, J 7.7, 1.7 Hz); 7.46 (1H, dt, J 7.7, 1.7 Hz); 7.05–6.98 (2H, m); 4.33 (1H, dd, J 11.3, 3.0 Hz); 4.11 (1H, dd, J 11.3, 4.8 Hz); 3.90 (3H, s); 3.43–3.37 (1H, m); 2.93–2.90 (2H, m)

(ii) 2-{3-[4-(4-Fluoro-phenoxy)-piperidin-1-yl]-2-hydroxy-propoxy}-benzoic acid methyl ester Prepared according to the method described in Example 1, step (ii). Isolated as the free amine $^1$H-NMR: (400 MHz, CDCl$_3$): δ 7.81 (1H, dd, J 8.1, 1.8 Hz); 7.46 (1H, dt, J 7.8, 1.7 Hz); 7.03–6.91 (4H, m); 6.86–6.82 (2H, m); 4.28–4.10 (3H, m); 4.08–4.00 (1H,m); 3.88 (3H, s); 2.92–2.84 (1H, m); 2.83–2.76 (1H, m); 2.66–2.53 (2H, m); 2.46 (1H, t, J 10.2 Hz); 2.36 (1H, t, J 10.2 Hz); 2.02–1.92 (2H, m); 1.86–1.74 (2H, m); 1.63 (1H, bs)

APCI-MS: m/z 404.2 [MH$^+$]

EXAMPLE 7

2-(2-{3-[4-(3,4-Difluoro-phenoxy)-piperidin-1-yl]-2-hydroxy-propoxy}-benzoylamino)-2-methyl-propionic acid methyl ester (i) Methyl 2-[(2-hydroxybenzoyl)amino]-2-methylpropanoate To a solution of 2-(chlorocarbonyl)phenyl acetate (20 mmol, 3.96 g) in toluene (50 ml) were N-ethyl-N,N-diisopropylamine (22 mmol, 2.84 g) and 2-methylalamine (22 mmol, 2.27 g) added. After stirring the reaction mixture at room temperature overnight, the mixture was diluted with 250 ml toluene and was washed with 1.8% HCl/aq (250 ml) and sat. NaCl/aq (250 ml). The organic phase was dried over Na$_2$SO$_4$ and concentrated under reduced pressure. The residue was dissolved in MeOH (50 mL) and 3 drops of conc. H$_2$SO$_4$ were added. The mixture was refluxed for 2 hours and concentrated under reduced pressure. The residue was dissolved in 250 mL EtOAc and washed with sat.NaHCO$_3$/aq (250 ml) and sat. NaCl/aq (250 ml). The organic phase was dried over Na$_2$SO$_4$ and concentrated at reduced pressure. The resulting crude material was used without further purification.

APCI-MS m/z: 238 [MH$^+$]

(ii) Methyl 2-methyl-2-{[2-(2-oxiranylmethoxy)benzoyl]amino}propanoate

A solution of methyl 2-[(2-hydroxybenzoyl)amino]-2-methylpropanoate, K$_2$CO$_3$ (20 mmol, 2.68 g) and 2-(chloromethyl)oxirane (22 mmol, 2.03 g) in acetonitrile (60 ml) was stirred at reflux temperature overnight. The reaction mixture was diluted with EtOAc and washed with 1.8% HCl/aq (250 ml) and sat. NaCl/aq (250 ml). The organic phase was dried over Na$_2$SO$_4$ and concentrated at reduced pressure. The residue was purified on C$_{18}$-column (H$_2$O:CH$_3$CN, 0.1M NH$_4$OAc buffer, gradient 10% to 95% CH$_3$CN) to give the subtitle compound (244 mg, 5% yield, two steps).

APCI-MS m/z: 294 [MH$^+$]

$^1$H NMR (400 MHz, CDCl$_3$): δ 8.40(s, 1H), 8.14 (dd, 1H), 7.41 (dt, 1H), 7.07 (t, 1H), 6.90 (d, 1H), 4.44 (dd, 1H), 4.07 (dd, 1H), 3.74 (s, 3H), 3.45 (m, 1H), 2.94 (dd, 1H), 2.84 (dd, 1H), 1.64 (d, 6H)

(iii) 2-(2-{3-[4-(3,4-Difluoro-phenoxy)-piperidin-1-yl]-2-hydroxy-propoxy}-benzoylamino)-2-methyl-propionic acid methyl ester A toluene solution of 4-(3,4-difluorophenoxy)piperidine (0.03 ml, 0.5 M) was mixed with a toluene solution of methyl 2-methyl-2-{[2-(2-oxiranylmethoxy)benzoyl]amino}-propanoate (0.03 ml, 0.5 M). The mixture was diluted with 0.20 ml toluene and 0.05 ml methanol. The reaction mixture was stirred overnight at 100° C. in sealed vials. The product were concentrated in vacuo and used without any purification.

APCI-MS m/z: 507 [MH$^+$]

$^1$H NMR (400 MHz, CDCl$_3$): δ 8.13 (s, 1H), 7.90 (dd, 1H), 7.33 (dt, 1H), 7.07–6.96 (m, 2H), 6.89 (d, 1H), 6.73–6.68 (m, 1H), 6.58–6.55 (m, 1H), 4.77–4.72 (m, 1H), 4.49 (bs, 1H), 4.20–4.13 (m, 2H), 3.69 (s, 3H), 3.58–3.44 (m, 2H), 3.39–3.26 (m, 4H), 2.54–2.40 (m, 2H), 2.13–2.04 (m, 2H), 1.60 (d, 6H)

EXAMPLE 8

N-[2-({(1R,2S,3R)*-3-[4-(3,4-dichlorophenoxy)-1-piperidinyl)-2-hydroxycyclopentyl}oxy)phenyl] acetamide and N-[2-({(1S,2S,3R)*-3-[4-(3,4-dichlorophenoxy)-1-piperidinyl)-2-hydroxycyclopentyl}oxy)phenyl] acetamide (i) N-[2-(2-cyclopenten-1-yloxy)phenyl]acetamide To a suspension of sodium hydride (60 proc. in paraffin; 297 mg, 7.43 mmol, 1.1 equiv.) in DMF (3 ml) a solution of 2-acetamido-phenol (1.02 g, 6.75 mmol, 1.0 equiv.) in DMF (12 ml) was added dropwise at 0° C. After 30 minutes chlorocyclopent-2-ene (R. Moffett, *Organic Synthesis*, Wiley: New York 1963, Collect. Vol. IV, p.238–241) (762 mg, 0.76 ml, 7.43 mmol, 1.1 equiv.) was added by a syringe and stirring was continued overnight. Aqueous work-up followed by flash chromatography on silica gel (heptane/ethyl acetate, 2:1 continued to 1:1) afforded 992 mg (68%), of the subtitle compound as a dark, yellow oil.

$^1$H-NMR (400 MHz, CDCl$_3$): δ 8.35 (1H, d, J 8.0 Hz), 7.73 (1H, bs), 7.00 (1H, td, J 7.9, 1.5 Hz), 6.90–6.95 (2H, m), 6.17 (1H, m), 5.95 (1H, m), 5.36 (1H, d, J 5.9 Hz), 2.59 (1H, m), 2.38 (2H, m), 2.17 (3H, s), 1.97 (1H, m).

MS-ESI+: m/z 218.1 [MH+].

(ii) N-{2-(6-oxabicyclo[3.1.0]hex-2-yloxy)phenyl}acetamide

To an ice bath cooled solution of N-[2-(2-cyclopenten-1-yloxy)phenyl]acetamide (149 mg, 686 μmol, 1.0 equiv.) in dichloromethane (4 ml) m-chloroperbenzoic acid (85 proc.; 146 μmol, 1.1 equiv.) was added. After stirring overnight with slowly warming up to an ambient temperature the reaction mixture was diluted by tertbutyl(methyl)ether, washed successively by a sat. sodium bisulfate solution, 5 proc. sodium hydroxide and brine and dried over sodium sulfate. Evaporation of the solvent and flash chromatography on silica gel (ethyl acetate/heptane, 2:3 continued to ethyl acetate) yielded 93 mg (58%) of the subtitle compound as a mixture of the trans, (minor) and the cis (major) diastereoisomeric epoxides as a pale yellow oil. The cis/trans ratio was determined as 2:1 by $^1$H-NMR.

$^1$H-NMR (400 MHz, CDCl$_3$): δ 8.39 (1H [A], m), 8.34 (1H [B], d, J 8.2 Hz), 7.91 (1H [A], bs), 7.59 (1H, [B], bs), 6.92–7.25 (3H [A]+3H [B], m), 4.89 (1H [B], d, J 5.2 Hz), 4.77 (1H [A], td, J 8.0, 1.3 Hz), 3.66 (1H [B], m), 3.64 (1H [B], m), 3.60 (1H, [A], m), 3.54 (1H [A], m), 2.23 (1H [B], d, J 8.4 Hz), 2.21 (3H [A], s), 2.19 (3H [B], s), 2.10 (2H [A], m), 1.72–1.92 (m), 1.53–1.63 (m) (2H [A]+3H [B]). (A=trans, B=cis)

MS-ESI+: m/z 234.1 [MH+].

(iii) N-[2-({(1R,2S,3)*-3-[4-(3,4-dichlorophenoxy)-1-piperidinyl)-2-hydroxycyclopentyl}oxy)phenyl]acetamide and N-[2-({(1S,2S,3R)*-3-[4-(3,4-dichlorophenoxy)-1-piperidinyl)-2-hydroxycyclopentyl}oxy)phenyl]acetamide N-{2-(6-oxabicyclo[3.1.0]hex-2-yloxy)phenyl}acetamide (racemic mixture of the trans and cis diastereoisomers) (87 mg, 373 μmol, 1.0 equiv.) and 4-(3, 4-dichlorophenoxy)piperidine (92 mg, 394 μmol, 1.06 equiv.) were dissolved in 2 M lithium perchlorate in acetonitrile (3 ml) and heated in a sealed tube over night at 85° C. Aqueous work-up and flash chromatography of the crude on silica gel (heptane/ethyl acetate/methanol/ammonia= 1:3:0:0 continued to 0:90:10:1 to 0:80:20:3) led to the separation of two diastereoisomeric addition products to give 24 mg (14%) of the (1S,2S,3R) diastereoisomer (first eluted) and 75 mg (42%) of the second eluted (1R,2S,3R) diastereoisomer.

For (1S,2S,3R) diastereoisomer $^1$H-NMR (400 MHz, CDCl$_3$): δ 8.27 (1H, dd, J 7.6, 1.7 Hz), 7.91 (1H, s), 7.29 (1H, d, J 8.9 Hz), 6.88–7.00 (4H, m), 6.73 (1H, dd, J 8.9, 2.8 Hz), 4.45 (1H, m), 4.28 (1H, hept, J 3.6 Hz), 4.18 (1H, dd, J 7.1, 4.6 Hz), 2.87 (3H, m), 2.71 (1H, q, J 7.5 Hz), 2.15 (3H, s), 2.11 (1H, m), 1.78–2.02 (7H, m).

MS-APCI+: m/z 479.1 [MH+].

For (1R,2S,3R) diastereoisomer $^1$H-NMR (400 MHz, CDCl$_3$): δ 8.20–8.25 (2H, m), 7.29 (1H, d, J 8.9 Hz), 6.91–7.00 (4H, m), 6.74 (1H, dd, J 8.9, 2.8 Hz), 4.46 (1H, bq, J 4.8 Hz), 4.29 (1H, m), 4.13 (1H, d, J 7.2 Hz), 2.95 (2H, m), 2.84 (2H, m), 2.50 (2H, m), 2.15 (3H, s), 1.93–2.07 (5H, m), 1.82 (2H, m), 1.58 (1H, m).

MS-APCI+: m/z 479.1 [MH+].

EXAMPLE 9

N-[2-({(2,3-trans)-3-[4-(3,4-dichlorophenoxy)-1-piperdinyl]-2-hydroxycyclohexy}oxy)phenyl]acetamide (i) N-[2-(2-cyclohexen-1-yloxy)phenyl]acetamide 2-Cyclohexenol (491 mg, 0.49 ml, 5.00 mmol, 1.0 equiv.); 2-acetamidophenol (756 mg, 5.00 mmol, 1.0 equiv.) and triphenylphosphine (1.44 g, 5.50 mmol, 1.1 equiv.) were dissolved in THF (10 ml) and kept at ambient temperature by a water bath. After dropwise addition of diethyl azodicarbonic acid (871 mg, 0.78 ml, 5.00 mmol, 1.0 equiv.), dissolved in TBF (3 ml), the reaction mixture was stirred over night Extractive work-up and flash chromatography on silica gel (heptane/tertbutyl(methyl)ether=1:1) afforded 224 mg (19%) the title compound as a yellow oil.

MS-ESI+: m/z 232.2 [MH+].

(ii) N-[2-(7-oxabicyclo[4.1.0]hept-2-yloxy)phenyl]acetamide

To a solution of N-[2-(2-cyclohexen-1-yloxy)phenyl]acetamide (76 mg, 329 μmol, 1.0 equiv.) in dichloromethane (5 ml) m-chlorobenzoic acid (85 proz.; 121 mg, 559 μmol, 1.7 equiv.) was added at 0° C. Stirring was continued overnight while the reaction mixture was allowed to warm up slowly to room temperature. The heterogenous mixture was diluted with ethyl acetate and washed with sat sodium sulfite, 5% sodium hydroxide and brine. Drying over sodium sulfate, evaporation of the solvent and flash chromatography on silica gel provided 59 mg (73%) of the title compound as a mixture of the diastereoisomers (ratio A:B=trans:cis=5:3 [$^1$H-NMR]).

$^1$H-NMR (400 MHz, CDCl$_3$): δ 8.35 (1H [A]+1H [B], m), 8.02 (1H [A], bs), 7.70 (1H [B], bs), 6.95–7.04 (3H [A]+3H [B], m), 4.62 (1H [A], dd, J 8.4, 5.5, 2.1 Hz), 4.55 (1H [B], dd, J 7.5, 6.7 Hz), 3.30–3.36 (2H [A]+1H [B], m), 3.19 (1H [B], t, J 3.6 Hz), 1.26–2.23 (10H [A]+10H [B], m).

LC/MS-ESI+: m/z 248.1 [MH+(A)], 248.2 [MH+(B)].

(iii) N-[2-({(2,3-trans)-3-[4-(3,4-dichlorophenoxy)-1-piperidinyl]-2-hydroxycyclohexyl}oxy)phenyl]acetamide The diastereoisomeric mixture of N-[2-(7-oxabicyclo [4.1.0]hept-2-yloxy)phenyl]acetamide (59 mg, 239 μmol, 1.0 equiv.) and 4-(3,4-dichlorophenoxy)piperidine (56 mg, 239 μmol, 1.0 equiv.) were dissolved in 2 M lithium perchlorate in acetonitrile (2 ml) and heated in a sealed tube over night at 85° C. Aqueous work-up and flash chromatography on silica gel (heptane/ethyl acetate/methanol= 50:100:3) gave 86 mg (75%) as a yellow oil in a diastereoisomeric ratio of 69:31=A:B ($^1$H-NMR). No separation of the diastereoisomers on reversed phase columns could be observed. The relative stereochemistry of the major and minor diastereoisomers, respectively, could not be assigned due to the complex spectrum of the mixture.

$^1$H-NMR (400 MHz, CDCl$_3$): δ 9.48 (1H [A], bs), 9.25 (1H [B], bs), 8.46 (1H [A]+1H [B], t, J 9.1 Hz), 7.22–7.32 (2H [A]+1H [B], m), 6.93–7.08 (4H [A]+5H [B], m), 6.72–6.76 (1H [A]+1H [B], m), 4.08–4.30 (3H [A]+3H [B], m), 3.55–3.64 (2H [A]+1H [B], m), 2.96–3.07 (2H [A]+2H [B], m), 2.71 (2H [A]+3H [B], m), 2.19 (3H [A], s), 2.16 (3H [B], s), 1.47–2.37 (10H [A]+10H [B], m).

MS-ESI+: m/z 493.1 [MH+(A, B)].

The following compounds were prepared by routes analogous to those described in the previous Examples.

EXAMPLE 10

N-(5-Chloro-2-{3-[3-(3,4-dichloro-phenoxy)-pyrrolidin-1-yl]-2-hydroxy-propoxy}-phenyl)-acetamide APCI-MS: m/z 473.1 475.1 [MH$^+$]

EXAMPLE 11

N-(3-Acetyl-2-{3-[3-(3,4-dichloro-phenoxy)-pyrrolidin-1-yl]-2-hydroxy-propoxy)-5-methyl-phenyl)-acetamide APCI-MS: m/z 495.1 497.1 [MH$^+$]

EXAMPLE 12

N-(2-{3-[3-(3,4-Dichloro-phenoxy)-pyrrolidin-1-yl]-2-hydroxy-propoxy}-4-methyl-phenyl)-acetamide APCI-MS: m/z 453.1 455.1 [MH$^+$]

EXAMPLE 13

N-(2-{3-[3-(3,4-Dichloro-phenoxy)-pyrrolidin-1-yl]-2-hydroxy-propoxy}-5-fluoro-phenyl)-acetamide APCI-MS: m/z 457.1 459.1 [MH$^+$]

EXAMPLE 14

1-[3-(3,4-Dichloro-phenoxy)-pyrrolidin-1-yl]-3-(1H-indol-7-yloxy)-propan-2-ol

APCI-MS: m/z 421.1 423.1 [MH$^+$]

EXAMPLE 15

1-(7-{3-[3-(3,4-Dichloro-phenoxy)-pyrrolidin-1-yl]-2-hydroxy-propoxy}-indol-1-yl)-ethanone APCI-MS: m/z 463.1 465.1 [MH$^+$]

EXAMPLE 16

N-(4-{3-[-(3,4-Dichloro-phenoxy)-pyrrolidin-1-yl]-2-hydroxy-propoxy}-biphenyl-3-yl)-acetamide APCI-MS: m/z 515.1 517.1 [MH$^+$]

EXAMPLE 17

N-(2-{3-[3-(3,4-Dichloro-phenoxy)-pyrrolidin-1-yl]-2-hydroxy-propoxy}-4-fluoro-phenyl)-acetamide APCI-MS: m/z 457.1 459.1 [MH$^+$]

EXAMPLE 18

N-(2-{3-[3-(3,4-Dichloro-phenoxy)-pyrrolidin-1-yl]-2-hydroxy-propoxyl-5-methyl-phenyl)-acetamide APCI-MS: m/z 453.1 455.1 [MH$^+$]

EXAMPLE 19

N-(2-{3-[3-(3,4-Dichloro-phenoxy)-pyrrolidin-1-yl]-2-hydroxy-propoxy}-phenyl)-acetamide APCI-MS: m/z 439.1 441.1 [MH$^+$]

EXAMPLE 20

N-(5-Chloro-2-{3-[3-(4-chloro-phenoxy)-pyrrolidin-1-yl]-2-hydroxy-propoxy}-phenyl)-acetamide APCI-MS: m/z 439.1 441.1 [MH$^+$]

EXAMPLE 21

N-(3-Acetyl-2-{3-[3-(4-chloro-phenoxy)-pyrrolidin-1-yl]-2-hydroxy-propoxy}-5-methyl-phenyl)-acetamide APCI-MS: m/z 461.1 [MH$^+$]

EXAMPLE 22

N-(2-{3-[3-(4-Chloro-phenoxy)-pyrrolidin-1-yl]-2-hydroxy-propoxy}-4-methyl-phenyl)-acetamide APCI-MS: m/z 419.1 [MH$^+$]

EXAMPLE 23

N-(2-{3-[3-(4-Chloro-phenoxy)-pyrrolidin-1-yl]-2-hydroxy-propoxy}-5-fluoro-phenyl)-acetamide APCI-MS: m/z 423.1 [MH$^+$]

EXAMPLE 24

1-[3-(4-Chloro-phenoxy)-pyrrolidin-1-yl]-3-(1H-indol-7-yloxy)-propan-2-ol

APCI-MS: m/z 387.1 [MH$^+$]

EXAMPLE 25

1-(7-{3-[3-(4-Chloro-phenoxy)-pyrrolidin-1-yl]-2-hydroxy-propoxy}-indol-1-yl)-ethanone APCI-MS: m/z 429.1 [MH$^+$]

EXAMPLE 26

N-(4-{3-[3-(4-Chloro-phenoxy)-pyrrolidin-1-yl]-2-hydroxy-propoxy}-biphenyl-3-yl)-acetamide APCI-MS: m/z 481.1 [MH$^+$]

EXAMPLE 27

N-(2-{3-[3-(4-Chloro-phenoxy)-pyrrolidin-1-yl]-2-hydroxy-propoxy}-4-fluoro-phenyl)-acetamide APCI-MS: m/z 423.1 [MH$^+$]

EXAMPLE 28

N-(2-{3-[3-(4-Chloro-phenoxy)-pyrrolidin-1-yl]-2-hydroxy-propoxy}-5-methyl-phenyl)-acetamide APCI-MS: m/z 419.1 [MH$^+$]

EXAMPLE 29

N-(2-{3-[3-(4-Chloro-phenoxy)-pyrrolidin-1-yl]-2-hydroxy-propoxy}-phenyl)-acetamide APCI-MS: m/z 405.1 [MH$^+$]

EXAMPLE 30

N-(5-Chloro-2-(3-[3-(4-fluoro-phenoxy)-pyrrolidin-1-yl]-2-hydroxy-propoxy}-phenyl)-acetamide APCI-MS: m/z 423.1 [MH$^+$]

EXAMPLE 31

N-(3-Acetyl-2-{3-[3-(4-fluoro-phenoxy)-pyrrolidin-1-yl]-2-hydroxy-propoxy}-5-methyl-phenyl)-acetamide APCI-MS: m/z 445.3 MH$^+$]

EXAMPLE 32

N-(2-{3-[3-(4-Fluoro-phenoxy)-pyrrolidin-1-yl]-2-hydroxy-propoxy}-4-methyl-phenyl)acetamide APCI-MS: m/z 403.3 [MH$^+$]

EXAMPLE 33

N-(5-Fluoro-2-{3-[3-(4-fluoro-phenoxy)-pyrrolidin-1-yl]-2-hydroxy-propoxy}-phenyl)-acetamide APCI-MS: m/z 407.1 [MH$^+$]

EXAMPLE 34

1-[3-(4-Fluoro-phenoxy)-pyrrolidin-1-yl]-3-(1H-indol-7-yloxy)-propan-2-ol

APCI-MS; m/z 371.1 [MH$^+$]

EXAMPLE 35

1-(7-{3-[3-(4-Fluoro-phenoxy)-pyrrolidin-1-yl]-2-hydroxy-propoxy}-indol-1-yl)-ethanone APCI-MS: m/z 413.1 [MH$^+$]

EXAMPLE 36

N-(4-{3-[3-(4-Fluoro-phenoxy)-pyrrolidin-1-yl]-2-hydroxy-propoxy}-biphenyl-3-yl)-acetamide APCI-MS: m/z 465.3 [MH$^+$]

EXAMPLE 37

N-(4-Fluoro-2-{3-[3-(4-fluoro-phenoxy)-pyrrolidin-1-yl]-2-hydroxy-propoxy}-phenyl)-acetamide APCI-MS: m/z 407.1 [MH$^+$]

EXAMPLE 38

N-(2-{3-[3-(4-Fluoro-phenoxy)-pyrrolidin-1-yl]-2-hydroxy-propoxy}-5-methyl-phenyl)-acetamide APCI-MS: m/z 403.1 [MH$^+$]

EXAMPLE 39

N-(2-{3-[3-(4-Fluoro-phenoxy)-pyrrolidin-1-yl]-2-hydroxy-propoxy}-phenyl)-acetamide APCI-MS: m/z 389.1 [MH$^+$]

EXAMPLE 40

N-(5-Chloro-2-(3-[3-(3,4-difluoro-phenoxy)-pyrrolidin-1-yl]-2-hydroxy-propoxy}-phenyl)-acetamide APCI-MS: m/z 441.1 [MH$^+$]

EXAMPLE 41

N-(3-Acetyl-2-{3-[3-(3,4-difluoro-phenoxy)-pyrrolidin-1-yl]-2-hydroxy-propoxy}-5-methyl-phenyl)-acetamide APCI-MS: m/z 463.3 [MH$^+$]

EXAMPLE 42

N-(2-{3-[3-(3,4-Difluoro-phenoxy)-pyrrolidin-1-yl]-2-hydroxy-propoxy}-4-methyl-phenyl)-acetamide APCI-MS: m/z 421.1 [MH$^+$]

EXAMPLE 43

N-(2-{3-[3-(3,4-Difluoro-phenoxy)-pyrrolidin-1-yl]-2-hydroxy-propoxy}-5-fluoro-phenyl)-acetamide APCI-MS: m/z 425.1 [MH$^+$]

EXAMPLE 44

1-[3-(3,4-Difluoro-phenoxy)-pyrrolidin-1-yl]-3-(1H-indol-7-yloxy)-propan-2-ol

APCI-MS: m/z 389.1 [MH$^+$]

EXAMPLE 45

1-(7-{3-[3-(3,4-Difluoro-phenoxy)-pyrrolidin-1-yl]-2-hydroxy-propoxy}-indol-1-yl)-ethanone APCI-MS: m/z 431.1 [MH$^+$]

EXAMPLE 46

N-(4-{3-[3-(3,4-Difluoro-phenoxy)-pyrrolidin-1-yl]-2-hydroxy-propoxy}-biphenyl-3-yl)-acetamide APCI-MS: m/z 483.3 [MH$^+$]

EXAMPLE 47

N-(2-{3-[3-(3,4-Difluoro-phenoxy)-pyrrolidin-1-yl]-2-hydroxy-propoxy}-4-fluoro-phenyl)-acetamide APCI-MS: m/z 425.1 [MH$^+$]

EXAMPLE 48

N-(2-{3-[3-(3,4-Difluoro-phenoxy)-pyrrolidin-1-yl]-2-hydroxy-propoxy}-5-methyl-phenyl)-acetamide APCI-MS: m/z 421.1 [MH$^+$]

EXAMPLE 49

N-(2-{3-[3-(3,4-Difluoro-phenoxy)-pyrrolidin-1-yl]-2-hydroxy-propoxy}-phenyl)-acetamide APCI-MS: m/z 407.1 [MH$^+$]

EXAMPLE 50

N-(5-Chloro-2-{3-[4-(3,4-dichloro-phenoxy)-piperidin-1-yl]-2-hydroxy-propoxy}-phenyl)acetamide APCI-MS: m/z 487.1 489.1 [MH$^+$]

EXAMPLE 51

N-(3-Acetyl-2-{3-[4-(3,4-dichloro-phenoxy)-piperidin-1-yl]-2-hydroxy-propoxy}-5-methyl-phenyl)-acetamide APCI-MS: m/z 509.1 511.1 [MH$^+$]

EXAMPLE 52

N-(2-{3-[4-(3,4-Dichloro-phenoxy)-piperidin-1-yl]-2-hydroxy-propoxy}-4-methyl-phenyl)-acetamide APCI-MS: m/z 467.1 469.1 [MH$^+$]

EXAMPLE 53

N-(2-{3-[4-(3,4-Dichloro-phenoxy)-piperidin-1-yl]-2-hydroxy-propoxy)-5-fluoro-phenyl)-acetamide APCI-MS: m/z 471.1 473.1 [MH$^+$]

Comparison Example 54

1-[4-(3,4-Dichloro-phenoxy)-piperidin-1-yl]-3(1H-indol-7-yloxy)-propan-2-ol

APCI-MS: m/z 435.1 437.1 [MH$^+$]

EXAMPLE 55

1-(7-{3-[4-(3,4-Dichloro-phenoxy)-piperidin-1-yl]-2-hydroxy-propoxy-indol-1-yl)-ethanone APCI-MS: m/z 477.1 479.1 [MH$^+$]

EXAMPLE 56

N-(4-{3-[4-(3,4-Dichlorophenoxy)-piperidin-1-yl]-2-hydroxy-propoxy}-biphenyl-3-yl)-acetamide APCI-MS: m/z 429.1 431.1 [MH$^+$]

EXAMPLE 57

N-(2-{3-[4-(3,4-Dichloro-phenoxy)-piperidin-1-yl]-2-hydroxypropoxy}-4-fluoro-phenyl)-acetamide APCI-MS: m/z 471.1 473.1 [MH$^+$]

EXAMPLE 58

N-(2-{3-[4-(3,4-Dichloro-phenoxy)-piperidin-1-yl]-2-hydroxy-propoxy}-5-methyl-phenyl)-acetamide APCI-MS: m/z 467.1 469.1 [MH$^+$]

EXAMPLE 59

N-(2-{3-[4-(3,4-Dichloro-phenoxy)-piperidin-1-yl]-2-hydroxy-propoxy}-phenyl)-acetamide APCI-MS: m/z 453.1 455.1 [MH$^+$]

EXAMPLE 60

N-5-Chloro-2-{3-[4-(4-chloro-phenoxy)-piperidin-1-yl]-2-hydroxy-propoxy}-phenyl)-acetamide APCI-MS: m/z 453.1 455.1 [MH$^+$]

EXAMPLE 61

N-(3-Acetyl-2-{3-[4-(4-chloro-phenoxy)-piperidin-1-yl]-2-hydroxy-propoxy}-5-methyl-phenyl)-acetamide APCI-MS: m/z 475.3 [MH$^+$]

EXAMPLE 62

N-(2-{3-[4-(4-Chloro-phenoxy)-piperidin-1-yl]-2-hydroxy-propoxy}-4-methyl-phenyl)-acetamide APCI-MS: m/z 433.1 [MH$^+$]

EXAMPLE 63

N-(2-{3-[4-(4-Chloro-phenoxy)-piperidin-1-yl]-2-hydroxy-propoxy}-5-fluoro-phenyl)-acetamide APCI-MS: m/z 437.1 [MH$^+$]

Comparison Example 64

1-[4-(4-Chloro-phenoxy)-piperidin-1-yl]-3-(1H-indol-7-yloxy)-propan-2-ol

APCI-MS: m/z 401.1 [MH$^+$]

EXAMPLE 65

1-(7-{3-[4-(4-Chloro-phenoxy)-piperidin-1-yl]-2-hydroxy-propoxy}-indol-1-yl)-ethanone APCI-MS: m/z 443.1 [MH$^+$]

EXAMPLE 66

N-(4-{3-[4-(4-Chloro-phenoxy)-piperidin-1-yl]-2-hydroxy-propoxy}-biphenyl-3-yl)-acetamide APCI-MS: m/z 495.3 [MH$^+$]

EXAMPLE 67

N-(2-{3-[4-(4-Chloro-phenoxy)-piperidin-1-yl]-2-hydroxy-propoxy}-4-fluoro-phenyl)-acetamide APCI-MS:m/z 437.1 [MH$^+$]

EXAMPLE 68

N-(2-{3-[4-(4-Chloro-phenoxy)-piperidin-1-yl]-2-hydroxy-propoxy}-5-methyl-phenyl)-acetamide APCI-MS: m/z 433.1 [MH$^+$]

EXAMPLE 69

N-(2-{3-[4-(4-Chloro-phenoxy)-piperidin-1-yl]-2-hydroxy-propoxy}-phenyl)-acetamide APCI-MS: m/z 419.1 [MH$^+$]

EXAMPLE 70

N-55-Chloro-2-[3-(8-chloro-1,3,4,5-tetrahydro-pyrido[4,3-b]indol-2-yl)-2-hydroxy-propoxy]-phenyl}-acetamide -phenyl}-acetamide APCI-MS: m/z 448.1 450.1 [MH$^+$]

EXAMPLE 71

N-{3-Acetyl-2-[3-(8-chloro-1,3,4,5-tetrahydro-pyrido[4,3-b]indol-2-yl)-2-hydroxy-propoxy]-5-methyl-phenyl}-acetamide APCI-MS: m/z 470.1 [MH$^+$]

EXAMPLE 72

N-{2-[3-(8-Chloro-1,3,4,5-tetrahydro-pyrido[4,3-b]indol-2-yl)-2-hydroxy-propoxy]-4-methyl-phenyl}-acetamide APCI-MS: m/z 428.1 [MH$^+$]

EXAMPLE 73

N-{2-[3-(8-Chloro-1,3,4,5-tetrahydro-pyrido[4,3-b]indol-2-yl)-2-hydroxy-propoxy]-5-fluoro-phenyl}-acetamide APCI-MS: m/z 432.1 [MH$^+$]

EXAMPLE 74

1-(8-Chloro-1,3,4,5-tetrahydro-pyrido[4,3-b]indol-2-yl)-3-(1H-indol-7-yloxy)-propan-2-ol APCI-MS: m/z 396.1 [MH$^+$]

EXAMPLE 75

1-{7-[3-(8-Chloro-1,3,4,5-tetrahydro-pyrido[4,3-b]indol-2-yl)-2-hydroxy-propoxy]-indol-1-yl}-ethanone APCI-MS: m/z 438.1 [MH$^+$]

EXAMPLE 76

N-{4-[3-(8-Chloro-1,3,4,5-tetrahydro-pyrido[4,3-b]indol-2-yl)-2-hydroxy-propoxy]-biphenyl-3-yl}-acetamide APCI-MS: m/z 490.1 [MH$^+$]

EXAMPLE 77

N-{2-[3-(8-Chloro-1,3,4,5-tetrahydro-pyrido[4,3-b]indol-2-yl)-2-hydroxy-propoxy]-4-fluoro-phenyl}-acetamide APCI-MS: m/z 432.1 [MH$^+$]

EXAMPLE 78

N-{2-[3-(8-Chloro-1,3,4,5-tetrahydro-pyrido[4,3-b]indol-2-yl)-2-hydroxy-propoxy]-5-methyl-phenyl}-acetamide APCI-MS: m/z 428.1 [MH$^+$]

EXAMPLE 79

N-{2-[3-(8-Chloro-1,3,4,5-tetrahydro-pyrido[4,3-b]indol-2-yl)-2-hydroxy-propoxy]-phenyl}-acetamide APCI-MS: m/z 414.1 [MH+]

EXAMPLE 80

N-{5-Chloro-2-[3-(8-fluoro-1,3,4,5-tetrahydro-pyrido[4,3-b]indol-2-yl)-2-hydroxy-propoxy]-phenyl}-acetamide APCI-MS:m/z 432.1 [MH+]

EXAMPLE 81

N-{3-Acetyl-2-[3-(8-fluoro-1,3,4,5-tetrahydro-pyrido[4,3-b]indol-2-yl)-2-hydroxy-propoxy]-5-methyl-phenyl}-acetamide APCI-MS: m/z 454.3 [MH+]

EXAMPLE 82

N-{2-[3-(8-Fluoro-1,3,4,5-tetrahydro-pyrido[4,3-b]indol-2-yl)-2-hydroxy-propoxy]-4-methyl-phenyl}-acetamide APCI-MS: m/z 412.1 [MH+]

EXAMPLE 83

N-{5-Fluoro-2-[3-(8-fluoro-1,3,4,5-tetrahydro-pyrido[4,3-b]indol-2-yl)-2-hydroxy-propoxy]phenyl}-acetamide APCI-MS: m/z 416.1 [MH+]

EXAMPLE 84

1-(8-Fluoro-1,3,4,5-tetrahydro-pyrido[4,3-b]indol-2-yl)-3-(1H-indol-7-yloxy)-propan-2-ol APCI-MS: m/z 380.1 [MH+]

EXAMPLE 85

1-{7-[3-(8-Fluoro-1,3,4,5-tetrahydro-pyrido[4,3-b]indol-2-yl)-2-hydroxy-propoxy]-1-yl}-ethanone APCI-MS: m/z 422.1 [MH+]

EXAMPLE 86

N-{4-[3-(8-Fluoro-1,3,4,5-tetrahydro-pyrido[4,3-b]indol-2-yl)-2-hydroxy-propoxy]-biphenyl-3-yl}-acetamide APCI-MS: m/z 474.3 [MH+]

EXAMPLE 87

N-{4-Fluoro-2-[3-(8-fluoro-1,3,4,5-tetrahydro-pyrido[4,3-b]indol-2-yl)-2-hydroxy-propoxy]-phenyl}-acetamide APCI-MS: m/z 416.1 [MH+]

EXAMPLE 88

N-{2-[3-(8-Fluoro-1,3,4,5-tetrahydro-pyrido[4,3-b]indol-2-yl)-2-hydroxy-propoxy]-5-methyl-phenyl}-acetamide APCI-MS: m/z 412.1 [MH+]

EXAMPLE 89

N-{2-[3-(8-Fluoro-1,3,4,5-tetrahydro-pyrido[4,3-b]indol-2-yl)-2-hydroxy-propoxy]-phenyl}-acetamide APCI-MS: m/z 398.1 [MH+]

EXAMPLE 90

N-(2-{3-[4-(3,4-Dichloro-phenoxy)-piperidin-1-yl]-2-hydroxy-propoxy}-phenyl)-acetamide APCI-MS m/z: 453, 455 [MH+]

EXAMPLE 91

3-(2-{3-[4-(3,4-Dichloro-phenoxy)-piperidin-1-yl]-2-hydroxy-propoxy}-phenyl)-propionic acid methyl ester APCI-MS m/z: 482, 484 [MH+]

EXAMPLE 92

1-[4-(3,4-Dichloro-phenoxy)-piperidin-1-yl]-3-(2,6-dimethoxy-phenoxy)-propan-2-ol APCI-MS m/z: 456, 458 [MH+]

EXAMPLE 93

1-[4-(3,4-Dichloro-phenoxy)-piperidin-1-yl]-3-(2-methoxy-phenoxy)-propan-2-ol

APCI-MS m/z: 426, 428 [MH+]

EXAMPLE 94

2-{3-[4-(3,4-Dichloro-phenoxy)-piperidin-1-yl]-2-hydroxy-propoxy}-N,N-dimethyl-benzamide APCI-MS m/z: 467, 469 [MH+]

EXAMPLE 95

1-(2-{3-[4-(3,4-Dichloro-phenoxy)-piperidin-1-yl]-2-hydroxy-propoxy}-phenyl)-propan-1-one APCI-MS m/z: 452, 454 [MH+]

EXAMPLE 96

1-(2-{3-[4-(3,4-Dichloro-phenoxy)-piperidin-1-yl]-2-hydroxy-propoxy}-phenyl)-ethanone APCI-MS m/z: 438, 440 [MH+]

EXAMPLE 97

3-(2-{3-[3-(4-Fluoro-phenoxy)-pyrrolidin-1-yl]-2-hydroxy-propoxy}-phenyl)-propionic acid methyl ester APCI-MS m/z: 418 [MH+]

EXAMPLE 98

1-(2,6-Dimethoxy-phenoxy)-3-[3-(4-fluoro-phenoxy)-pyrrolidin-1-yl]-propan-2-ol

APCI-MS m/z: 392 [MH+]

EXAMPLE 99

1-[3-(4-Fluoro-phenoxy)-pyrrolidin-1-yl]-3-(2-methoxy-phenoxy)-propan-2-ol

APCI-MS m/z: 362 [MH+]

EXAMPLE 100

(2-{3-[3-(4-Fluoro-phenoxy)-pyrrolidin-1-yl]-2-hydroxy-propoxy}-benzoylamino)-acetic acid methyl ester APCI-MS m/z: 447 [MH+]

EXAMPLE 101

(2-{3-[3-(4-Chloro-phenoxymethyl)-piperidin-1-yl]-2-hydroxy-propoxy}-benzoylamino)-acetic acid methyl ester APCI-MS m/z: 491 [MH+]

EXAMPLE 102

2-(2-{3-[3-(4-Fluoro-phenoxy)-pyrrolidin-1-yl]-2-hydroxy-propoxy}-benzoylamino)-2-methyl-propionic acid methyl ester APCI-MS m/z: 475 [MH+]

EXAMPLE 103

2-{3-[3-(4-Fluoro-phenoxy)-pyrrolidin-1-yl]-2-hydroxy-propoxy}-N,N-dimethyl-benzamide APCI-MS m/z: 403 [MH+]

EXAMPLE 104

1-(2-{3-[3-(4-Fluoro-phenoxy)-pyrrolidin-1-yl]-2-hydroxy-propoxy}-6-methoxy-phenyl)-ethanone APCI-MS m/z: 404 [MH+]

EXAMPLE 105

1-(2-{3-[3-(4-Fluoro-phenoxy)-pyrrolidin-1-yl]-2-hydroxy-propoxy}-phenyl)-propan-1-one APCI-MS m/z: 388 [MH+]

EXAMPLE 106

1-(2-{3-[3-(4-Fluoro-phenoxy)-pyrrolidin-1-yl]-2-hydroxy-propoxy}-phenyl)-ethanone APCI-MS m/z: 374 [MH+]

EXAMPLE 107

N-[2-(3-{[1-(3,4-dichlorobenzyl)-4-piperidinyl]amino}-2-hydroxypropoxy)-4-methylphenyl]acetamide APCI-MS: m/z 480 [MH+]

EXAMPLE 108

3-(2-{3-[3-(3,4-Difluoro-phenoxy)-pyrrolidin-1-yl]-2-hydroxy-propoxy}-phenyl)-propionic acid methyl ester APCI-MS m/z: 436 [MH+]

EXAMPLE 109

1-[3-(3,4-Difluoro-phenoxy)-pyrrolidin-1-yl]-3-(2-methoxy-phenoxy)-propan-2-ol

APCI-MS m/z: 380 [MH+]

EXAMPLE 110

(2-{3-[3-(3,4-Difluoro-phenoxy)-pyrrolidin-1-yl]-2-hydroxy-propoxy}-benzoylamino)-acetic acid methyl ester APCI-MS m/z: 465 [MH+]

EXAMPLE 111

2-{3-[3-(3,4-Difluoro-phenoxy)-pyrrolidin-1-yl]-2-hydroxy-propoxy}-N,N-dimethyl-benzamide APCI-MS m/z: 421 [MH+]

EXAMPLE 112

1-(2-{3-[3-(3,4-Difluoro-phenoxy)-pyrrolidin-1-yl]-2-hydroxy-propoxy}-6-methoxy-phenyl)-ethanone APCI-MS m/z: 422 [MH+]

EXAMPLE 113

1-(2-{3-[3-(3,4-Difluoro-phenoxy)-pyrrolidin-1-yl]-2-hydroxy-propoxy}-phenyl)-propan-1-one APCI-MS m/z: 406 [MH+]

EXAMPLE 114

1-(2-{3-[3-(3,4-Difluoro-phenoxy)-pyrrolidin-1-yl]-2-hydroxy-propoxy}-phenyl)-ethanone APCI-MS m/z: 392 [MH+]

EXAMPLE 115

N-(2-{3-[4-(3,4-dichloroanilino)-1-piperidinyl]-2-hydroxypropoxy}phenyl)acetamide APCI-MS: m/z 452.1 [MH+]

EXAMPLE 116

3-(2-{3-[3-(4-Chloro-phenoxy)-pyrrolidin-1-yl]-2-hydroxy-propoxy}-phenyl)-propionic acid methyl ester APCI-MS m/z: 434 [MH+]

EXAMPLE 117

1-[3-(4-Chloro-phenoxy)-pyrrolidin-1-yl]-3-(2,6-dimethoxy-phenoxy)-propan-2-ol

APCI-MS m/z: 408 [MH+]

EXAMPLE 118

1-[3-(4-Chloro-phenoxy)-pyrrolidin-1-yl]-3-(2-methoxy-phenoxy)-propan-2-ol

APCI-MS m/z: 378 [MH+]

EXAMPLE 119

(2-{3-[3-(4-Chloro-phenoxy)-pyrrolidin-1-yl]-2-hydroxy-propoxy}-benzoylamino)-acetic acid, methyl ester APCI-MS m/z: 463 [MH+]

EXAMPLE 120

2-(2-{3-[3-(4-Chloro-phenoxy)-pyrrolidin-1-yl]-2-hydroxy-propoxy}-benzoylamino)-2-methyl-propionic acid methyl ester APCI-MS m/z: 491 [MH+]

EXAMPLE 121

2-{3-[3-(4-Chloro-phenoxy)-pyrrolidin-1-yl]-2-hydroxy-propoxy}-N,N-dimethyl-benzamide APCI-MS m/z: 419 [MH+]

EXAMPLE 122

1-(2-{3-[3-(4-Chloro-phenoxy)-pyrrolidin-1-yl]-2-hydroy-propoxy}-6-methoxy-phenyl)-ethanone APCI-MS m/z: 420 [MH+]

EXAMPLE 123

1-(2-{3-[3-(4-Chloro-phenoxy)-pyrrolidin-1-yl]-2-hydroxy-propoxy}-phenyl)-propan-1-one APCI-MS m/z: 404 [MH+]

EXAMPLE 124

1-(2-{3-[3-(4-Chloro-phenoxy)-pyrrolidin-1-yl]-2-hydroxy-propoxy}-phenyl)-ethanone APCI-MS m/z: 390 [MH+]

EXAMPLE 125

N-(2-{3-[3-(4-Cyano-phenoxy)-pyrrolidin-1-yl]-2-hydroxy-propoxy}-phenyl)-acetamide APCI-MS m/z: 396 [MH+]

EXAMPLE 126

3-(2-{3-[3-(4-Cyano-phenoxy)-pyrrolidin-1-yl]-2-hydroxy-propoxyl-phenyl}-propionic acid methyl ester APCI-MS m/z: 425 [MH+]

EXAMPLE 127

(2-{3-[3-(4-Cyano-phenoxy)-pyrrolidin-1-yl]-2-hydroxy-propoxy)-benzoylamino)-acetic acid methyl ester APCI-MS m/z: 454 [MH+]

EXAMPLE 128

2-{3-[3-(4-Cyano-phenoxy)-pyrrolidin-1-yl]-2-hydroxy-propoxy}-N,N-dimethyl-benzamide APCI-MS m/z: 410 [MH+]

EXAMPLE 129

4-{1-[2-Hydroxy-3-(2-propionyl-phenoxy)-propyl]-pyrrolidin-3-yloxy}-benzonitrile APCI-MS m/z: 395 [MH+]

EXAMPLE 130

N-(2-{2-Hydroxy-3-[3-(4-methoxy-phenoxy)-pyrrolidin-1-yl]-propoxy}-phenyl)-acetamide APCI-MS m/z: 401 [MH+]

EXAMPLE 131

N-(4-chloro-2-{3-[4-(3,4-dichloroanilino)-1-piperidinyl]-2-hydroxypropoxy}phenyl)acetamide APCI-MS: m/z 486 [MH+]

EXAMPLE 132

3-(2-{3-[3-(3,4-Dichloro-phenoxy)-pyrrolidin-1-yl]-2-hydroxy-propoxy}-phenyl)-propionic acid methyl ester APCI-MS m/z: 468, 470 [MH+]

EXAMPLE 133

1-[3-(3,4-Dichloro-phenoxy)-pyrrolidin-1-yl]-3-(2-methoxy-phenoxy)-propan-2-ol

APCI-MS m/z: 412, 414 [MH+]

EXAMPLE 134

(2-{3-[3-(3,4-Dichloro-phenoxy)-pyrrolidin-1-yl]-2-hydroxy-propoxy}-benzoylamino)-acetic acid methyl ester APCI-MS m/z: 497, 499 [MH+]

EXAMPLE 135

2-(2-{3-[3-(3,4-Dichloro-phenoxy)-pyrrolidin-1-yl]-2-hydroxy-propoxy}-benzoylamino)-2-methyl-propionic acid methyl ester APCI-MS m/z: 525, 527 [MH+]

EXAMPLE 136

2-[3-[3-(3,4-Dichloro-phenoxy)-pyrrolidin-1-yl]-2-hydroxy-propoxy}-N,N-dimethyl-benzamide APCI-MS m/z: 453, 455 [MH+]

EXAMPLE 137

1-(2-{3-[3-(3,4-Dichloro-phenoxy)-pyrrolidin-1-yl]-2-hydroxy-propoxy}-6-methoxy-phenyl)-ethanone APCI-MS m/z: 454, 456 [MH+]

EXAMPLE 138

1-(2-{3-[3-(3,4-Dichloro-phenoxy)-pyrrolidin-1-yl]-2-hydroxy-propoxy}-phenyl)-propan-1-one APCI-MS m/z: 438, 440 [MH+]

EXAMPLE 139

1-(2-{3-[3-(3,4-Dichloro-phenoxy)-pyrrolidin-1-yl]-2-hydroxy-propoxy}-phenyl)-ethanone APCI-MS m/z: 424, 426 [MH+]

EXAMPLE 140

N-(2-{3-[4-(3,4-Difluoro-phenoxy)-piperidin-1-yl]-2-hydroxy-propoxy}-phenyl)-acetamide APCI-MS m/z: 421 [MH+]

EXAMPLE 141

3-(2-{3-[4-(3,4-Difluoro-phenoxy)-piperidin-1-yl]-2-hydroxy-propoxy}-phenyl)-propionic acid methyl ester APCI-MS m/z: 450 [MH+]

EXAMPLE 142

2-{3-[4-(3,4-Difluoro-phenoxy)-piperidin-1-yl]-2-hydroxy-propoxy}-N,N-dimethyl-benzamide APCI-MS-m/z: 435 [MH+]

EXAMPLE 143

1-(2-{3-[4-(3,4-Difluoro-phenoxy)-piperidin-1-yl]-2-hydroxy-propoxy}-phenyl)-propan-1-one APCI-MS m/z: 420 [MH+]

EXAMPLE 144

(2-{3-[4-(3,4-Difluoro-phenoxy)-piperidin-1-yl]-2-hydroxy-propoxy}-benzoylamino)-acetic acid methyl ester APCI-MS m/z: 479 [MH+]

EXAMPLE 145

N-(2-{3-[3-(3,4-Difluoro-phenoxymethyl)-piperidin-1-yl]-2-hydroxy-propoxy}-phenyl)-acetamide APCI-MS m/z: 435 [MH+]

EXAMPLE 146

N-(2-{3-[4-(4-Fluoro-phenoxy)-piperidin-1-yl]-2-hydroxy-propoxy}-phenyl)-acetamide APCI-MS m/z: 403 [MH+]

EXAMPLE 147

3-(2-{3-[4-(4-Fluoro-phenoxy)-piperidin-1-yl]-2-hydroxy-propoxy}-phenyl)-propionic acid methyl ester APCI-MS m/z: 432 [MH+]

EXAMPLE 148

1-(2,6-Dimethoxy-phenoxy)-3-[4-(4-fluoro-phenoxy)-piperidin-1-yl]-propan-2-ol

APCI-MS m/z: 406 [MH+]

EXAMPLE 149

1-[4-(4-Fluoro-phenoxy)-piperidin-1-yl]-3-(2-methoxy-phenoxy)-propan-2-ol

APCI-MS m/z: 376 [MH+]

EXAMPLE 150

1-(2-{3-[4-(4-Fluoro-phenoxy)-piperidin-1-yl]-2-hydroxy-propoxy}-phenyl)-ethanone APCI-MS m/z: 388 [MH+]

EXAMPLE 151

2-{3-[4-(4-Fluoro-phenoxy)-piperidin-1-yl]-2-hydroxy-propoxy}-N,N-dimethyl-benzamide APCI-MS m/z: 417 [MH+]

EXAMPLE 152

1-(2-{3-[4-(4-Fluoro-phenoxy)-piperidin-1-yl]-2-hydroxy-propoxy}-phenyl)-propan-1-one APCI-MS m/z 402 [MH+]

EXAMPLE 153

(2-{3-[4-(4-Fluoro-phenoxy)-piperidin-1-yl]-2-hydroxy-propoxy}-benzoylamino)-acetic acid methyl ester APCI-MS m/z: 461 [MH+]

EXAMPLE 154

N-(2-{3-[3-(4-Fluoro-phenoxymethyl)-piperidin-1-yl]-2-hydroxy-propoxy}-phenyl)-acetamide APCI-MS m/z: 417 [MH+]

EXAMPLE 155

3-(2-{3-[3-(4-Fluoro-phenoxymethyl)-piperidin-1-yl]-2-hydroxy-propoxy}-phenyl)-propionic acid methyl ester APCI-MS m/z: 446 [MH+]

EXAMPLE 156

1-[3-(4-Fluoro-phenoxymethyl)-piperidin-1-yl]-3-(2-methoxy-phenoxy)-propan-2-ol

APCI-MS m/z: 390 [MH+]

EXAMPLE 157

1-(2-{3-[3-(4-Fluoro-phenoxymethyl)-piperidin-1-yl]-2-hydroxy-propoxy}-phenyl)-ethanone APCI-MS m/z: 402 [MH+]

EXAMPLE 158

2-(2-{3-[3-(4-Fluoro-phenoxymethyl)-piperidin-1-yl]-2-hydroxy-propoxy)-benzoylamino)-2-methyl-propionic acid methyl ester APCI-MS m/z: 503 [MH+]

EXAMPLE 159

2-{3-[3-(4-Fluoro-phenoxymethyl)-piperidin-1-yl]-2-hydroxy-propoxy}-N,N-dimethyl-benzamide APCI-MS m/z: 431 [MH+]

EXAMPLE 160

1-(2-{3-[3-(4-Fluoro-phenoxymethyl)-piperidin-1-yl]-2-hydroxy-propoxy}-methoxy-phenyl)-ethanone APCI-MS m/z: 432 [MH+]

EXAMPLE 161

N-(2-3-[4-(4-Acetylamino-phenoxy)-piperidin-1-yl]-2-hydroxy-propoxy}-phenyl)-acetamide APCI-MS m/z: 442 [MH+]

EXAMPLE 162

N-(4-{1-[3-(2-Acetyl-phenoxy)-2-hydroxy-propyl]-piperidin-4-yloxy}-phenyl)-acetamide APCI-MS m/z: 427 [MH+]

EXAMPLE 163

N-(4-cyano-2-{3-[4-(3,4-dichloroanilino)-1-piperidinyl]-2-hydroxypropoxy}phenyl)acetamide APCI-MS: m/z 477 [MH+]

EXAMPLE 164

3-(2-{3-[4-(4-Chloro-phenoxy)-piperidin-1-yl]-2-hydroxy-propoxy}-phenyl)-propionic acid methyl ester APCI-MS m/z: 448 [MH+]

EXAMPLE 165

1-[4-(4-Chloro-phenoxy)-piperidin-1-yl]-3-(2-methoxy-phenoxy)-propan-2-ol

APCI-MS m/z: 392 μMH+]

EXAMPLE 166

1-(2-{3-[4-(4-Chloro-phenoxy)-piperidin-1-yl]-2-hydroxy-propoxy}-phenyl)-ethanone APCI-MS m/z: 404 [MH+]

EXAMPLE 167

2-(2-{3-[4-(4-Chloro-phenoxy)-piperidin-1-yl]-2-hydroxy-propoxy}-benzoylamino)-2-methyl-propionic acid methyl ester APCI-MS m/z: 505 [MH+]

EXAMPLE 168

2-{3-[4-(4-Chloro-phenoxy)-piperidin-1-yl]-2-hydroxy-propoxy}-N,N-dimethyl-benzamide APCI-MS m/z: 433 [MH+]

EXAMPLE 169

1-(2-{3-[4-(4-Chloro-phenoxy)-piperidin-1-yl]-2-hydroxy-propoxy}-6-methoxy-phenyl)-ethanone APCI-MS m/z: 434 [MH+]

EXAMPLE 170

1-(2-{3-[4-(4-Chloro-phenoxy)-piperidin-1-yl]-2-hydroxy-propoxy}-phenyl)-propan-1-one APCI-MS m/z: 418 [MH+]

EXAMPLE 171

(2-{3-[4-(4-Chloro-phenoxy)-piperidin-1-yl]-2-hydroxy-propoxy}-benzoylamino)-acetic acid methyl ester APCI-MS m/z: 477 [MH+]

EXAMPLE 172

N-(2-{3-[3-(4-Chloro-phenoxymethyl)-piperidin-1-yl]-2-hydroxy-propoxy}-phenyl)-acetamide APCI-MS m/z: 433 [MH+]

EXAMPLE 173

3-(2-{3-[3-(4-Chloro-phenoxymethyl)-piperidin-1-yl]-2-hydroxy-propoxy}-phenyl)-propionic acid methyl ester APCI-MS m/z: 462 [MH+]

EXAMPLE 174

1-(2-{3-[3-(4-Chloro-phenoxymethyl)-piperidin-1-yl]-2-hydroxy-propoxy}-phenyl)-ethanone APCI-MS m/z: 418 [MH+]

EXAMPLE 175

2-{3-[3-(4-Chloro-phenoxymethyl)-piperidin-1-yl]-2-hydroxy-propoxy}-N,N-dimethyl-benzamide APCI-MS m/z: 447 [MH+]

EXAMPLE 176

1-(2-{3-[3-(4-Chloro-phenoxymethyl)-piperidin-1-yl]-2-hydroxy-propoxy}-phenyl)-propan-1-one APCI-MS m/z: 432 [MH+]

EXAMPLE 177

N-[2-({(1R,2R)-2-[4-(3,4-dichlorophenoxy)-1-piperidinyl]-1-hydroxycyclopentyl}methoxy)phenyl]acetamide

EXAMPLE 178

Methyl (2S,4R)-1-{3-[2-(acetylamino)phenoxy]-2-hydroxypropyl}-4-[(4-chlorobenzyl)oxy]-2-pyrrolidinecarboxylate hydrochloride

EXAMPLES 179–189

Starting Materials

A) (3,4-Dichloro-phenyl)-piperidin-4yl-amine

In a nitrogen filled reaction vessel 4-oxo-piperidine-1-carboxylic acid tert-butyl ester (2.46 g, 12.3 mmol) and 3,4-dichloro-phenylamine (1.0 g, 6.17 mmol) were dissolved in dichloromethane (28 ml) and acetic acid (2.12 ml). Sodium triacetoxyborohydride (3.67 g, 17.3 mmol) was added at room temperature. The reaction was stirred over night and then poured into a sodium hydrogencarbonate solution (5%). The water phase was shaken three times with ethyl acetate (EtOAc). The combined organic phase was dried over sodium sulfate, evaporated and purified by flash chromatography (EtOAc:Heptane 3:7) giving 1.7 g, 81% of pure compound. The BOC-protected title compound was dissolved in dichloromethane (26 ml) and trifluoro acetic acid (13 ml) and stirred at room temperature for 3 h, evaporated and dissolved in diethyl ether and sodium hydroxide (1 M). The organic layer was separated and the water phase washed twice with ether. The combined organic layer was washed with a small portion of brine, dried over sodium sulfate and evaporated to give 1.15 g (76%) of the title compound.

1H-NMR (400 MHz, DMSO-d6): δ 7.20 (d, 1H, J=8.9 Hz), 6.73 (d, 1H, J=2.7 Hz), 6.54 (dd, 1H, J=8.8, 2.7 Hz), 5.95 (d, 1H, J=8.1 Hz), 3.22 (m, 1H), 2.91 (bd, 2H, J=12.6 Hz), 2.51 (m, 2H), 2.02 (bs, 1H), 1.81 (bd, 2H, J=12.4 Hz), 1.18 (m).

APCI-MS: m/z 245 [M+]

B) (4-Chloro-phenyl)-piperidin-4yl-amine

Was synthesised in the same way as (A) from 4-oxo-piperidine-1-carboxylic acid tert-butyl ester (3.59 g, 18.0 mmol), 4-chloro-phenylamine (1.15 g, 9.0 mmol) and sodium triacetoxyborhydride (5.34 g, 25.2 mmol) in dichloromethane (40 ml) and acetic acid (3.1 ml). The deprotection was run in dichloromethane (37 ml) and trifluoro acetic acid (18 ml). Yield 1.5 g, 79%

$^1$H-NMR (400 MHz, DMSO-d6): δ 7.04 (d, 2H, J=8.9 Hz), 6.55 (d, 2H, J=8.9 Hz), 5.62 (d, 1H, J=8.1 Hz), 3.18 (m, 1H), 2.92 (bd, 2H, J=12.6 Hz), 2.50 (m, 2H), 1.99 (bs, 1H), 1.82 (d, 2H, J=12.7 Hz), 1.18 (m, 2H).

APCI-MS: m/z 211 [MH+]

C) (4-Fluoro-phenyl)-piperidin-4yl-amine

Was synthesised in the same way as (A) from 4-oxo-piperidine-1-carboxylic acid tert-butyl ester (3.59 g, 18.0 mmol), 4-fluoro-phenylamine (1.0 g, 9.0 mmol) and sodium triacetoxyborhydride (5.34 g, 25.2 mmol) in dichloromethane (40 ml) and acetic acid (3.1 ml). The deprotection was run in dichloromethane (37 ml) and trifluoro acetic acid (18 ml). Yield 1.1 g, 63%

$^1$H-NMR (400 MHz, DMSO-d6): δ 6.85 (t, 2H, J=9.0 Hz), 6.51 (dd, 2H, J=9.1, 4.6 Hz), 5.27 (d, 1H, J=8.2 Hz), 3.13 (m, 1H), 2.89 (bd, 2H, J=12.5 Hz), 2.48 (m, 2H), 1.80 (bd, 2H, J=12.3 Hz), 1.14 (m, 2H).

APCI-MS: m/z 195 [MH+]

D) (3,4-Difluoro-phenyl)-piperidin-4yl-amine

Was synthesised in the same way as (A) from 4-oxo-piperidine-1-carboxylic acid tert-butyl ester (3.59 g, 18.0 mmol), 3,4-difluoro-phenylamine (1.16 g, 9.0 mmol) and sodium triacetoxyborohydride (5.34 g, 25.2 mmol) in dichloromethane (40 ml) and acetic acid (3.1 ml). The deprotection was run in dichloromethane (37 ml) and trifluoro acetic acid (18 ml). Yield 1.26 g, 66%

$^1$H-NMR (400 MHz, DMSO-d6): δ 7.05 (dt, 1H, J=10.8, 9.2 Hz), 6.50 (ddd, 1H, J=14.1, 7.0, 2.8 Hz), 6.32 (bd, 1H, J=9.20 Hz), 5.64 (d, 1H, J=8.14 Hz), 3.17 (m, 1H), 2.90 (bd, 2H, J=12.6 Hz), 2.50 (m, 2H), 2.00 (bs, 1H), 1.81 (bd, 2H, J 12.6 Hz), 1.16 (m, 2)

APCI-MS: m/z 213 [MH+]

EXAMPLE 179

N-(2-{3-[4-(3,4-Dichloroanilino)-1-piperidinyl]-2-hydroxypropoxy}-4-methylphenyl)acetamide APCI-MS: m/z 466 [MH+]

EXAMPLE 180

N-(2-{3-[4-(4-Chloroanilino)-1-piperidinyl]-2-hydroxypropoxy}phenyl)acetamide

APCI-MS: m/z 418 [MH+]

EXAMPLE 181

N-(4-Chloro-2-{3-[4-(4-chloroanilino)-1-piperidinyl]-2-hydroxypropoxy}phenyl)-acetamide APCI-MS: m/z 452 [MH+]

EXAMPLE 182

N-(2-{3-[4-(4-Chloroanilino)-1-piperidinyl]-2-hydroxypropoxy}-4-cyanophenyl)acetamide APCI-MS: m/z 443 [MH+]

EXAMPLE 183

N-(2-{3-[4-(4-Chloroanilino)-1-piperidinyl]-2-hydroxypropoxy}-4-methylphenyl)acetamide APCI-MS: m/z 432 [MH+]

EXAMPLE 184

N-(5-Chloro-2-{3-[4-(4-fluoroanilino)-1-piperidinyl]-2-hydroxypropoxy}phenyl)acetamide APCI-MS: m/z 436 [MH+]

EXAMPLE 185

N-(5-Chloro-2-{3-[4-(3,4-difluoroanilino)-1-piperidinyl]-2-hydroxypropoxy}phenyl)acetamide APCI-MS: m/z 454 [MH+]

EXAMPLE 186

N-(5-Cyano-2-{3-[4-(4-fluoroanilino)-1-piperidinyl]-2-hydroxypropoxy}-phenyl)acetamide APCI-MS: m/z 427 [MH+]

EXAMPLE 187

N-(5-Cyano-2-{3-[4-(3,4-difluoroanilino)-1-piperidinyl]-2-hydroxypropoxy}phenyl)acetamide APCI-MS: m/z 445 [MH+]

EXAMPLE 188

N-(2-{3-[4-(4-Fluoroanilino)-1-piperidinyl]-2-hydroxypropoxy}-4-methylphenyl)acetamide APCI-MS: m/z 416 [MH+]

EXAMPLE 189

N-(2-{3-[4-(3,4-Difluoroanilino)-1-piperidinyl]-2-hydroxypropoxy}-4-methylphenyl)acetamide APCI-MS: m/z 434 [MH+]

EXAMPLE 190

N-(2-{3-[3(S)-(4-Chloro-phenoxy)-pyrrolidin-1-yl]-2-(R)-hydroxy-propoxy-phenyl}acetamide i) 3-(S)-(4-Chloro-phenoxy)-pyrrolidine CF$_3$COOH To a solution of triphenyl phosphine (4.2 g, 16.02 mmol) in THF (75 mL) was added diethyl azodicarboxalate (2.52 mL) at 0° C., after 15 min 4-chlorophenol (2.05 g, 16.02 mmol) was added and after another 10 min 3-hydroxy-pyrrolidine-1-carboxylic acid tert-butyl ester (3.0 g, 16.02 mmol) in THF (20 mL) was added slowly. After addition was complete the ice bath was removed and the reaction mixture was kept at room temperature overnight. The solvent was removed in vacuo and the residue was stirred with diethyl ether, the solid triphenyl phosphine was filtered off. The residue was purified by flash chromatography (0–0.5% MeOH in CHCl$_3$) to give the subtitled compound (3.65 g, 76%) which was dissolved in dichloromethane (60 mL) and trifluoroacetic acid (15 mL) was added. The reaction mixture was kept at room temperature for 30 min. The solvent was removed in vacuo. The residue was dissolved in dichloromethane, diethylether and hexane were added. The solid was filtered off to give the subtitled compound 3.70 g, 97%.

$^1$H-NMR (CDCl$_3$, 400 MHz): δ 10.20 (s, 1H), 9.99 (s, 1H), 7.25 (d, J 8.8 Hz, 2H), 6.78 (d, J 8.8 Hz, 2H), 4.99 (m, 1H), 3.41 (m, 4H), 2.30 (m 1H), 2.20 (m, 1H).

APCI-MS: m/z 198 (MH$^+$).

ii) N-(2-{3-[3(S)-(4-Chloro-phenoxy)-pyrrolidin-1-yl]-2-(R)-hydroxy-propoxy-phenyl}acetamide A mixture of 3-(S)-(4-chloro-phenoxy)-pyrrolidine. CF$_3$COOH (312 mg, 1.0 mmol), N-acetyl-2-(2,3-epoxypropoxy)aniline (207 mg, 1.0 mmol), K$_2$CO$_3$ (560 mg) in EtOH (10 mL) was stirred at 65° C. for 4 h. The solvent was removed in vacuo. The residue was partitioned between ethyl acetate and water. The organic layer was washed with aqueous NHCl solution, then with water. The organic layer was dried over Na$_2$SO$_4$, filtered, concentrated. The residue was purified by flash chromatography (0–3% MeOH in CHCl$_3$) to give a mixture of diastereomers (310 mg, 77%). The diastereomers were seperated by HPLC to give N-(2-{3-[3(S)-(4-chloro-phenoxy)-pyrrolidin-1-yl]-2-(R)-hydroxy-propoxy-phenol}acetamide (57 mg).

$^1$H-NMR (CDCl$_3$, 400 MHz): δ 8.36 (m, 1H), 8.25 (s, 1H), 7.25 (m, 2H), 6.99 (m, 2H), 6.93 (m, 1H), 6.75 (m, 2H), 4.80 (m, 1H), 4.08 (m, 2H), 3.96 (m, 1H), 3.11 (dd, J 5.9 10.5 Hz, 1H), 3.01 (m, 1H), 2.82 (m, 2H), 2.59 (m, 1H), 2.51 (dd, J 3.2, 12.0 Hz, 1H), 2.29 (m, 1H), 2.19 (s, 3H), 2.01 (m, 1H). APCI-MS: m/z 405 (MH$^+$).

EXAMPLE 191

N-(2-{3-[3S-(4-Chloro-phenoxy)-pyrrolidin-1-yl]-2S-hydroxy-propoxy}-phenyl)-acetamide hydrochloride The reaction was performed analogously to Example 190.

$^1$H-NMR (CDCl$_3$, 400 MHz): δ 8.35 (m, 1H), 8.26 (s, 1H), 7.24 (m, 2H), 6.99 (m, 2H), 6.92 (m, 1H), 6.75 (m, 2H), 4.80 (m, 1H), 4.12 (m, 2H), 3.95 (m, 1H), 2.95 (m, 2H), 2.80 (m, 3H), 2.52 (dd, 3.4, 12.2 Hz, 1H), 2.30 (m, 1H), 2.19 (s, 3H), 2.01 (m, 1H).

APCI-MS: m/z 405 (MH$^+$).

EXAMPLE 192

N-(2-{3-[3(R)-(4-Chloro-phenoxy)-pyrrolidin-1-yl]-2-(S)-hydroxy-propoxy-phenyl)acetamide The reaction was performed analogously to Example 190.

$^1$H-NMR (CDCl$_3$, 400 MHz): δ 8.36 (m, 1H), 8.25 (s, 1H), 7.25 (m, 2H), 6.99 (m, 2H), 6.93 (m, 1H), 6.75 (m, 2H), 4.80 (m, 1H), 4.08 (m, 2H), 3.96 (m, 1H), 3.11 (dd, J 5.9 10.5 Hz, 1H), 3.01 (m, 1H), 2.82 (m, 2H), 2.59 (m, 1H), 2.51 (dd, J 3.2, 12.0 Hz, 1H), 2.29 (m, 1H), 2.19 (s, 3H), 2.01 (m, 1H).

APCI-MS: m/z 405 (MH$^+$).

EXAMPLE 193

N-[5-Chloro-2-({(2S)-3-[(3S)-3-(4-chloro-phenoxy)pyrrolidinyl]-2-hydroxypropyl}oxy)phenyl]acetamide The reaction was performed analogously to Example 190.

$^1$H-NMR (CDCl$_3$, 400 MHz): δ 8.45 (m, 1H), 8.36 (br, S, 1H), 7.23 (m, 2H), 6.95 (m, 1H), 6.85 (m, 1H), 6.75 (m, 2H), 4.80 (m, 1H), 4.07 (m, 2H), 3.91 (m, 1H), 2.95 (m, 2H), 2.80 (m, 3H), 2.49 (dd, J 3.2, 12.0 Hz, 1H), 2.30 (m, 1H), 2.19 (s, 3H), 2.03 (m, 1H).

APCI-MS: m/z 439 (MH$^+$).

EXAMPLE 194

N-[5-Chloro-2-({(2R)-3-[(3R)-3-(4-chloro-phenoxy)pyrrolidinyl]-2-hydroxypropyl}oxy)phenyl]acetamide The reaction was performed analogous to Example 190.

$^1$H-NMR (CDCl$_3$, 400 MHz): δ 8.45 (m, 1H), 8.36 (br, S, 1H), 7.23 (m, 21), 6.95 (m, 1H), 6.85 (m, 1H), 6.75 (m, 2H), 4.80 (m, 1H), 4.07 (m, 2H), 3.91 (m, 1H), 2.95 (m, 2H), 2.80 (m, 3H), 2.49 (dd, J 3.2, 12.0 Hz, 1H), 2.30 (m, 1H), 2.19 (s, 3H), 2.03 (m, 1H).

APCI-MS: m/z 439 (MH$^+$).

EXAMPLE 195

N-[5-Chloro-2-({(2S)-3-[(3R)-3-(4-chloro-phenoxy)pyrrolidinyl]-2-hydroxypropyl}oxy)phenyl]acetamide The reaction was performed analogously to Example 190.

$^1$H-NMR (CDCl$_3$, 400 MHz): δ 8.45 (m, 1H), 8.34 (br. S, 1H), 7.22 (m, 2H), 6.94 (m, 1H), 6.85 (m, 1H), 6.75 (m, 2H), 4.80 (m, 1H), 4.08 (m, 2H), 3.90 (m, 1H), 3.11 (dd, J 5.9, 10.5 Hz, 1H), 3.02 (m, 1H), 2.81 (m, 2H), 2.58 (m 1H), 2.49 (dd, J 3.5, 12.1 Hz, 1H), 2.30 (m, 1H), 2.18 (s, 3H), 2.01 (m, 1H).

APCI-MS: m/z 439 (MH$^+$).

EXAMPLE 196

N-[5-Chloro-2-({(2R)-3-[(3S)-3-(4-chloro-phenoxy)pyrrolidinyl]-2-hydroxypropyl}oxy)phenyl]acetamide The reaction was performed analogous to Example 190.

$^1$H-NMR (CDCl$_3$, 400 MHz): δ 8.45 (m, 1H), 8.34 (br. S, 1H), 7.22 (m, 2H), 6.94 (m, 1H), 6.85 (m, 1H), 6.75 (m, 2H), 4.80 (m, 1H), 4.08 (m, 2H), 3.90 (m, 1H), 3.11 (dd, J 5.9, 10.5 Hz, 1H), 3.02 (m, 1H), 2.81 (m, 2H), 2.58 (m 1H), 2.49 (dd, J 3.5, 12.1 Hz, 11 H), 2.30 (m, 1H), 2.18 (s, 3H), 2.01 (m, 1H).

APCI-MS: m/z 439 (MH$^+$).

EXAMPLE 197

N-(2-{3-[3-(4-Chloro-phenoxy)-pyrrolidin-1-yl]-2-hydroxy-propoxy}-4,5-difluoro-phenyl)-acetamide i) 4,5-Difluoro-2-nitro-phenol In a flask was dissolved 3,4-Difluorophenol (3.10 g, 23.7 mmole) in acetic acid (15 ml). To the stirred solution was added dropwise a solution of fuming HNO, (1.25 g, 29.7 mmole) in acetic acid (6 ml). The temperature was kept under 50° C. during the entire addition. After completed addition, the mixture was stirred for another hour. The reaction mixture was then poured onto ice-water, giving precipitation of a yellowish solid. The solid was collected by filtration, and dried. The solid was purified on silica (Heptane:EtOAc 5:1), giving the sub-title compound (2.05 g, 50%) as a yellow oil, which crystallizes on standing.

$^1$H-NMR (400 MHz, CDCl$_3$) δ: 10.61 (1H, s); 8.00 (1H, dd, J 9.6 8.2 Hz); 7.00 (1H, dd, J 10.4 6.8 Hz)

ii) N-(4,5-Difluoro-2-hydroxy-phenyl)-acetamide

In a flask was added the product obtained in i) (0.59 g, 3.37 mmole), and acetic acid (10 ml). The solution was heated with stirring to 90° C., and Tin (powder, 1.60 g, 13.5 mmole) was added. The flask was sealed and heated with stirring for another hour, and the hot solution was filtered through celite. The filter was then washed with another 10 ml of hot acetic acid. To the filtrate was added water (25 ml) and acetic anhydride (0.5 ml, 5.29 mmole), and the resulting mixture was heated with stirring at 60° C. for 20 minutes. The mixture was allowed to cool, and was partitioned between EtOAc and water. The organic phase was collected and washed with water and brine. The organic phase was evaporated to give the 0.63 g (100%) of the sub-title compound as a solid.

$^1$H-NMR (400 MHz, DMSO-d6) δ: 10.25 (1H, s); 9.31 (1H, bs); 7.88 (1H, dd, J 12.8 7.9 Hz); 6.83 (1H, dd, J 12.1 7.7 Hz); 2.08 (3H, s)

iii) N-(4,5-Difluoro-2-oxiranylmethoxy-phenyl)-acetamide

In a vial was added the compound obtained in ii) (0.4 g, 2.137 mmole), epibromohydrine (0.35 g, 2.55 mmole), $K_2CO_3$ (0.6 g, 4.4 mmole) and DMF (2 ml). The vial was sealed and heated with stirring (2 hours, 60° C.). The mixture was then partitioned between EtOAc and water, and the organic phase was washed twice with water and once with brine, and was finally evaporated to give a brown solid. The crude epoxide was purified on silica, to give 0.27 g (52%) of the sub-title compound as a slightly pink solid.

$^1$H-NMR (400 MHz, $CDCl_3$) δ: 8.37 (1H, dd, J 12.2 8.8 Hz); 7.85 (1H, bs); 6.78 (1H, dd, J 11.2 7.1 Hz); 4.34 (1H, dd, 11.5 2.2 Hz); 3.90 (1H, dd, 11.6 6.3 Hz); 3.40–3.36 (1H, m); 2.98 (1H t, J 4.5 Hz); 2.81 (1H, dd, J 4.7 6.3 Hz); 2.22 (3H, s)

iv) N-(2-{3-[3-(4-Chloro-phenoxy)-pyrrolidin-1-yl]-2-hydroxy-propoxy)-4,5-difluoro-phenyl}-acetamide In a vial was added the compound obtained in iii) (0.059 g, 0.24 mmole), 3-(4-chlorophenoxy)-pyrrolidine (0.048 g, 0.24 mmole) and ethanol (2 ml, 99.5%). The vial was sealed and the content was heated with stirring to 75° C. for 2 hours. The crude solution was evaporated and the obtained oil purified on silica to the title compound which was lyophilized as the hydrochloride. The title compound was obtained as a white solid (0.075 g, 65%). The compound was a mixture of four stereoisomers, which had an effect on the NMR-spectra.

$^1$H-NMR (400 MHz, DMSO-$d_6$) δ: 10.78–10.30 (1H, m); 9.30 (1H, s); 8.07 (1H, dd, J 12.8 9.3 Hz); 7.40–7.34 (2H, m); 7.23 (1H, dd, J 12.7 7.5 Hz); 7.05–6.99 (2H, m); 6.19 (1H, bs); 5.23–5.11 (1H, m); 4.35 (1H, bs); 4.08–3.97 (1.5H, m), 3.96–3.90 (1H, m); 3.84–3.70 (1.5H, m); 3.63–3.23 (4H, m); 2.66–2.00 (5H, m)

APCI-MS: m/z 411.1 [MH+]

EXAMPLE 198

N-{5-Chloro-2-[2-hydroxy-3-(3-phenoxy-pyrrolidin-1-yl)-propoxy]-phenyl}-acetamide The compound was prepared analogously to Example 197.

$^1$H-NMR (400 MHz, DMSO-$d_6$) δ: 10.80–10.36 (1H, m); 9.26 (1H, s); 8.14 (1H, s); 7.32 (2H, t, J 8.35 Hz); 7.11–6.95 (5H, m); 6.31–6.02 (1H, m); 5.24–5.12 (1H, m); 4.37 (1H, bs); 4.10–3.97 (1.5H, m); 3.95–3.88 (1H, m) 3.84–3.68 (1.5H, m); 3.64–3.26 (4H, m); 2.65–2.52 (0.5H, m); 2.35–2.02 (4.5H, m)

APCI-MS: m/z 405.2 [MH+]

EXAMPLE 199

N-(5-Chloro-2-{2-hydroxy-3-[3-(4-nitro-phenoxy)-pyrrolidin-1-yl]-propoxy}-phenyl)-acetamide The compound was prepared analogously to Example 197.

$^1$H-NMR (400 MHz, DMSO-$d_6$) δ: 10.95–10.48 (1H, m); 9.26 (1H, s); 8.24 (2H, d, J 9.6 Hz); 8.13 (1H, bs); 7.23–7.17 (2H, m); 7.12–7.02 (2H, m); 6.20 (1H, bs); 5.43–5.30 (1H, m); 4.38 (1H, m); 4.18–4.06 (0.5H, m); 4.05–3.97 (1H, m); 3.95–3.87 (1H, m); 3.86–3.72 (1.5H, m); 3.69–3.27 (4H, m); 2.73–2.60 (0.5H, m); 2.46–2.08 (4.5H, m)

APCI-MS: m/z 450.1 [MH+]

EXAMPLE 200

N-(5-Acetyl-2-{3-[5-(3,4-dichloro-phenoxy)-pyrrolidin-1-yl]-2-hydroxy-propoxy}-phenyl)-acetamide The compound was prepared analogously to Example 197.

APCI-MS: m/z 481.2, 483.2 [MH+]

EXAMPLE 201

4-Acetylamino-3-{3-[3-(3,4-dichloro-phenoxy)-pyrrolidin-1-yl]-2-hydroxy-propoxy}-benzoic acid methyl ester The compound was prepared analogously to Example 197.

APCI-MS: m/z 497.1, 499.2 [MH+]

EXAMPLE 202

N-(3-{3-[3-(3,4-Dichloro-phenoxy)-pyrrolidin-1-yl]-2-hydroxy-propoxy}-naphthalen-2-yl)-acetamide The compound was prepared analogously to Example 197.

APCI-MS: m/z 489.2, 491.2 [MH+]

EXAMPLE 203

N-(2-{3-[3-(4-Chloro-phenoxy)-pyrrolidin-1-yl]-2-hydroxy-propoxy}-5-cyano-phenyl)-acetamide The title compound was prepared according to the method in Example 197.

APCI-MS: m/z 430.2 [MH+]

EXAMPLE 204

4-Acetylamino-3-{3-[3-(4-chloro-phenoxy)-pyrrolidin-1-yl]-2-hydroxy-propoxy}-benzoic acid methyl ester The compound was prepared analogously to Example 197.

APCI-MS: m/z 463.2 [MH+]

EXAMPLE 205

N-(3-{3-[3-(4-Chloro-phenoxy)-pyrrolidin-1-yl]-2-hydroxy-propoxy}-naphthalen-2-yl)-acetamide The title compound was prepared according to the method in Example 197.

APCI-MS: m/z 455.2 [MH+]

EXAMPLE 206

N-(5-Cyano-2-{3-[4-(3,4-dichloro-phenoxy)-piperidin-1-yl]-2-hydroxy-propoxy}-phenyl)-acetamide The title compound was prepared according to the method in Example 197.

APCI-MS: m/z 478.2 480.1 [MH+]

EXAMPLE 207

N-(2-{3-[4-(3,4-Dichloro-phenoxy)-piperidin-1-yl]-2-hydroxy-propoxy}-5-trifluoromethyl-phenyl)-acetamide The title compound was prepared according to the method in Example 197.

APCI-MS: m/z 521.1 523.2 [MH+]

EXAMPLE 208

N-(5-Chloro-2-{3-[3-(4-fluoro-phenoxy)-pyrrolidin-1-yl]-2-hydroxy-propoxy}-phenyl)-acetamide trifluoroacetate The title compound was prepared according to the method in Example 197.

APCI-MS: m/z 423.1, 424.9 [MH+]

EXAMPLE 209

N-(5-Acetyl-2-{3-[3-(4-chloro-phenoxy)-pyrrolidin-1-yl]-2-hydroxy-propoxy}-phenyl)-acetamide trifluoroacetate i) N-(5-Acetyl-2-oxiranylmethoxy-fenyl)-acetamide To a solution of 4-acetyl-2-nitrophenol (0.50 g, 2.76 mmol) in TI (20 ml) was added 10% Pd/C (0.15 g). The resultant mixture was hydrogenated with $H_2$ at 1 atm for 5 hours and was then filtered through celite and evaporated to give 0.63 g of a red oil. Water (20 ml) and acetic anhydride (0.35 g, 3.44 mmol) was added and the mixture was stirred vigorously for 5 minutes. The reaction mixture was then heated with stirring to 60° C. for 30 minutes, and was then allowed to cool. A red solid was formed and the precipitate was collected by filtration, washed with water and dried to give 0.27 g (1.40 mmol) of N-(5-Acetyl-2-hydroxy-phenyl)-acetamide. This was dissolved in DMF (5 ml). $K_2CO_3$ (0.34 g, 2.45 mmol) and epibromohydrin (0.21 g, 1.54 mmol) was added and the resulting mixture was heated with stirring at 50° C. for 3 hours. The mixture was partitioned between EtOAc and water 40+40 ml. The organic phase was washed twice with water and once with brine and finally concentrated in vacuo to give a red oil. The crude product was purified on silica (Heptane/EtOAc, 1:2–1:4) to give 110 mg (16%) of the subtitle compound.

$^1$H-NM (400 MHz, $CDCl_3$): δ 9.03 (1H, d, J1.9 Hz), 7.81 (1H, bs), 7.74 (1H, dd, J8.6, 2.3 Hz), 6.96 (1H, d, J8.6 Hz), 4.48 (1H, dd, J11.3, 2.4 Hz) 4.00 (1H, dd, J11.4, 6.4 Hz), 3.45–3.40 (1H, m), 2.99 (1H, t, J4.4 Hz), 2.79 (1H, dd, J4.7, 2.6 Hz), 2.59 (3H, s), 2.26 (3H, s).

ii) N-(5-Acetyl-2-{3-[3-(4-chloro-phenoxy)-pyrrolidin-1-yl]-2-hydroxy-propoxy}-phenyl)-acetamide trifluoroacetate The title compound was prepared according to the method described in Example 197.

APCI-MS: m/z 447, 449 [MH$^+$]

EXAMPLE 210

N-(2-{3-[3-(4-Chlorophenoxy)-1-pyrrolidinyl]-2-hydroxypropoxy}phenyl)-methanesulfonamide i) 1-(2-Aminophenoxy)-3-[3-(4-chlorophenoxy)-1-pyrrolidinyl]-2-propanol dihydrochloride A mixture of N-(2-{3-[3-(4-chlorophenoxy)-1-pyrrolidinyl]-2-hydroxypropoxy}phenyl)acetamide (0.95 g, 2.34 mmol) and concentrated hydrochloric acid (25 mL) was heated (100–105° C.) for 3 hours then allowed to stand at room temperature overnight. The mixture was concentrated at reduced pressure to a third of its volume basified with saturated sodium hydrogen carbonate. The resulting suspension was extracted twice with ethyl acetate. The organic extracts were dried, the solvent was evaporated at reduced pressure to give a pale brown oil. This oil was dissolved in a minimum amount of methanol, diluted with ethyl ether and the product precipitated by addition of HCl-saturated ethyl ether. The product was filtered to afford the subtitle product (0.93 g, 91.2%).

APCI-MS: m/z 363 [MH$^+$] for the free base.

ii) N-(2-{3-[3-(4-Chlorophenoxy)-1-pyrrolidinyl]-2-hydroxypropoxy}phenyl)-methanesulfonamide Methanesulfonyl chloride (35 mg, 0.3 mmol) was added to cold (0 C), stirred mixture of the above amine (110 mg, 0.25 mmol) and pyridine (0.4 mL) in dry dichloromethane (10 mL). The mixture was then stirred at room temperature for 1.5 hour then concentrated. The residue was partitioned between ethyl acetate and water. The organic phase was concentrated and the residue was purified by flash chromatography (silica gel, dichloromethane-methanol, 25:1) to afford the title compound (68 mg, 61.8%) as a foam.

$^1$H-NMR (400 MHz, $CDCl_3$): δ 7.51 (dd, 1H, J=1.4 and 8.0 Hz), 7.22 (m, 2H), 7,10 (m, 1H), 7.68 (m. 1H), 6.92 (d, 1H, J=9.0 Hz), 6.76 (m, 2H), 5.78 (very bs, 1H), 4.80 (m, 1H), 4.20 (m, 1H), 4.08 (m, 1H), 3.98 (m, 1H), 3.16 (m, 1H), 3.01 (m, 1H), 2.96 (s, 3H), 2.89 (m, 2H), 2.74 (m, M), 2.68 (dd, 1H, J=4.0 and 12.2 Hz), 2.3 (m, 1H), and 2.02 (m, 1H).

$^{13}$C-NMR, 400 MHz, $CDCl_3$): δ 155.9, 149.4, 129.4, 126.9, 125.8, 125.77, 125.75, 122.29, 122.26, 12217, 115.5, 113.52, 113.50, 76.52, 76.49, 72.15, 72.09, 67.18, 67.08, 60.24, 60.07, 57.96, 57.94, 53.18, 52.98, 39.1, 31.92, 31.90.

APCI-MS: m/z 441 [MH$^+$].

EXAMPLE 211

N-(5-Chloro-2-[3-[3,4-dichlorophenoxy)-1-pyrrodinyl]-2-hydroxypropoxy]-phenyl)urea i) N-(5-Chloro-2-hydroxyphenyl)urea A solution of potassium cyanate (6.14 g, 75.6 mmol) in water (50 mL) was added dropwise to a stirred suspension of 2-amino-4-chlorophenol (5.00 g, 34.8 mmol) in a mixture of acetic acid (350 mL) and water (250 mL) and the resulting solution was stirred at room temperature for 3 hours. The reaction mixture was extracted three times with ethyl ether. The ether extracts were combined and concentrated to a thick oil. A 10% solution of sodium hydrogen carbonate (250 mL) was added to the above oil. The solid product was filtered and washed several times with water and recrystallized (toluene containing a little methanol) to afford the subtitle compound (3.27 g, 50.4%)

$^1$H-NMR (400 MHz, DMSO-d6): δ 10.1 (s, 1H), 8.07 (d, 1H, J=2.2 Hz), 8.04 (s, 1H), 6.75–6.78 (m, 2H), 6.29 (bs, 2H).

$^{13}$C-NMR: δ 156.0, 144.1, 130.0, 122.5, 120.2, 117.5, 115.2.

ii) N-[5-Chloro-2-(2-oxiranylmethoxy)phenyl]urea

A suspension of N-(5-chloro-2-hydroxyphenyl)urea (53 mg, 0.28 mmol), cesium carbonate (92 mg, 0.28 mmol) and epibromohydrine (49 mg, 0.36 mmol) in dry DMF (0.6 mL) was stirred at room temperature for 24 hours. The mixture was then partitioned between ethyl acetate and water. The organic phase was washed with water three times, dried and concentrated to a solid residue. This crude product was recrystallized (ethyl ether and heptane to afford the subtitle compound (18 mg, 26.5%).

$^1$H-NMR (400 MHz, DMSO-d6): δ 8.20 (d, 1H, J=2.2 Hz), 8.00 (s, 1H), 7.00 (d, 1H, J=8.8 Hz), 6.88 (dd, 1H, J=2.4 and 8.6 Hz), 6.40 (bs, 2H), 4.40 (dd, 1H, J=2.2 and 12.0 Hz), 3.90 (dd, 1H, J=6.6 and 12.0 Hz), 3.37 (m, 1H), 2.88 (t, 1H, H=4.8 Hz), 2.74 (m, 1H).

iii) N-(5-Chloro-2-[3-[3,4-dichlorophenoxy)-1-pyrrodinyl]-2-hydroxypropoxy]-phenyl)urea A solution of the subtitle compound (ii) (16 mg, 0.07 mmol) and 3-(3,4-dichlorophenoxy)pyrrolidine (17 mg, 0.07 mmol) in absolute ethanol (1 mL) for 2 hours. The solvent was removed under reduced pressure and the residue was purified by flash chromatography (dichloromethane-methanol, 15:1) to afford the title compound (11 mg, 33%).

$^1$H-NMR (400 MHz, DMSO-d6): δ 8.18 (d, 1H, J=2.6 Hz), 7.94 (s, 1H), 7.5 (d, 1H, J=0.0 Hz), 7.16 (d, 1H, J=2.1 Hz), 6.82–6.98 (m, 3H), 6.33 (bs, 2H), 4.98 (m, 1H), 4.90 (m, 1H), 3.85–4.07 (m, 3H), 2.63–2.93 (m, 5H), 2.21–2.30 (m, 1H), 1.74 (m, 1H).

APCI-MS: m/z 198 [MH$^+$]

EXAMPLE 212

1-(3-{2-[(Aminocarbonyl)amino]phenoxy}-2-hydroxypropyl)-3-(4-chlorophenoxy)pyrrolidinium-2,2,2-trifluoroacetate i) N-(2-Hydroxyphenyl)urea A solution of potassium cyanate (3.94 g, 48.6 mmol) in water (30 mL) was added during 15 min. to suspension of 2-aminophenol (2.41 g, 22.1 mmol) in 50% aqueous acetic acid (160 mL). The resulting solution was allowed to stand at room temperature overnight and then extracted with ethyl ether (3 times). The combined organic extracts was concentrated to small volume and poured into cold saturated aqueous sodium hydrogen carbonate. The solid was filtered and washed with water to afford the subtitle compound (1.61 g, 47.9%).

$^1$H-NMR (400 MHz, DMSO-d$_6$): δ 9.88 (s, 1H), 7.97 (s, 1H), 7.80 (bd, 1H), 6.77 (m, 1 H), 6.68 (m, 1H), 6.17 (s, 2H), ii) N-[2-(2-Oxiranylmethoxy)phenyl]urea A solution of epibromohydrin (0.94 g, 6.84 mmol) in dry DMF (2 mL) was added dropwise to a stirred suspension of N-(2-hydroxyphenyl)urea (0.65 g, 4.27 mmol) and cesium carbonate (2.22 g, 6.84 mmol) in DMF (8 mL). After 2 hours the mixture was partitioned between water and ethyl acetate. The aqueous phase was extracted with ethyl acetate and the combined organic phase was washed with water (3 times), dried and concentrated. The semi-solid residue was disssolved in dichloromethane/ethyl ether, filtered and heptane was added to turbidity. After standing at room temperature overnight, the solid was filtered to afford the subtitle compound (0.28 g, 32%).

$^1$H-NMR (400 MHz, DMSO-d$_6$): δ 8.07(m, 1H), 7.82 (s, 1H), 6.97 (m, 1H), 6.85 (m, 2H), 6.24 (bs, 2H), 4.37 (dd, 1H, J=2.5 and 11.6 Hz), 3.89 (dd, 1H, J=6.4 and 11.6 Hz), 3.38 (m, 1H), 2.87 (t, 1H, J=4.6 Hz), 2.75 (dd, 1H, J=2.6 and 5.2 Hz).

APCI-MS: m/z 209 [MH$^+$].

iii) 1-(3-{2-[(Aminocarbonyl)amino]phenoxy}-2-hydroxypropyl)-3-(4-chlorophenoxy)pyrrolidinium 2,2,2-trifluoroacetate A solution of N-[2-(2-oxiranylmethoxy)phenyl]urea (78 mg, 0.37 mmol) and 3-(4-chlorophenoxy)pyrrolidine (70 mg, 0.36 mmol) in absolute ethanol (4 mL) was heated at reflux for 2.5 hours. The mixture was then concentrated and the residue was purified by HPLC to afford the title compound (102 mg, 54.5%).

$^1$H-NMR (400 MHz, DMSO-d$_6$+D$_2$O): δ 7.98 (bd, 1H, J=7.2 Hz), 7.36 (d, 2H, J=8.8 Hz), 6.95–7.02 (m, 3H), 6.88 (m, 2H), 5.15 (bd, 1H). 4.26 (m, 1H). The remaining 10 aliphatic protons appear as complicated overlapping multiplets between δ 2.04 and 4.04.

APCI-MS: m/z 406 [MH$^+$] and 408 [MH$^+$+2] for the free base.

EXAMPLE 213

1-(3-{2-[(Aminocarbonyl)amino]phenoxy}-2-hydroxypropyl)-3-(3,4-dichlorophenoxy)pyrrolidinium 2,2,2-trifluoroacetate A solution of N-[2-(2-oxiranylmethoxy)phenyl]urea (Described under example 22, step ii; 69 mg, 0.33 mmol) and 3-(3,4-dichlorophenoxy)pyrrolidine (77 mg, 0.33 mmol) in absolute ethanol (4.5 mL) was heated at 70° C. for 2 hours. The residue after evaporation of the solvent was purified by HPLC to afford the title compound (133 mg, 72.3%).

$^1$H-NMR (400 MHz, DMSO-d$_6$+D$_2$O): δ 7.96 (bd, 1H, J=7.4 Hz), 7.54 (bd, 1H, J=9.0 Hz), 7.27 (bs, 1H), 6.84–7.00 (m, 4H), 5.20 (bd, 1H), 4.26 (m, 1H). The remaining 10 aliphatic protons appear as complicated overlapping multiplets between δ 2.05 and 4.03.

APCI-MS: m/z 439.9 [M] and 442 [M+2] for the free base.

EXAMPLE 214

1-(3-{2-[(Aminocarbonyl)amino]-4-chlorophenoxy)-2-hydroxypropyl)-3-(4-chlorophenoxy)pyrrolidinium 2,2,2-trifluoroacetate A solution of N-[2-(2-oxiranylmethoxy)phenyl]urea (described under Example 212, step ii; 47 mg, 0.22 mmol) and 3-(4-chlorophenoxy)pyrrolidine (41 mg, 0.2 mmol) in absolute ethanol (3 mL) was heated at 70° C. for 1.5 hours. The solvent was then evaporated and the residue was purified by HPLC to afford the title compound (67 mg, 60.9%).

$^1$H-NMR (400 MHz, CD$_3$OD): δ 8.04(s, 1H), 7.31 (d, 2H, J=8.6 Hz), 6.94–6.98 (m, 4H), 5.20 (bs, 1H), 4.40 (m, 1H). The remaining 10 aliphatic protons appear as complicated overlapping multiplets between δ 2.25 and 4.13.

APCI-MS: m/z 440.1 [M] and 442.1 [M+2] for the free base.

EXAMPLE 215

N-(2-{3-[3-(4-Chlorophenoxy)-1-pyrrolidinyl]-2-hydroxypropoxy}phenyl)-N'-ethylurea hydrochloride An ether solution of N-(2-{3-[3-(4-chlorophenoxy)-1-pyrrolidinyl]-2-hydroxypropoxy}phenyl)urea [obtained from the hydrochloride (110 mg, 0.25 mmol) by treatment with 1M NaOH and extraction with ether] was treated with ethyl isocyanate (16 μl, 0.2 mmol) in a sealed vial for 15 h at ambient temperature. After evaporation and purification by flash chromatography on silica (EtOAc/MeOH 100/5) the appropriate fractions were acidified with 1M HCl and lyophilized from acetic acid to give the title compound as a white amorphous solid (35 mg, 37%). The substance is a mixture of two diastereomeric pairs.

APCI-MS: m/z 434 [MH$^+$]

EXAMPLE 216

N-(2-{3-[3-(4-Chlorophenoxy)-1-pyrrolidinyl]-2-hydroxypropoxy}phenyl)-N'-methylurea hydrochloride To a solution of N-(2-{3-[3-(4-chlorophenoxy)-1-pyrrolidinyl]-2-hydroxypropoxy}phenyl)urea [obtained from the hydrochloride (44 mg, 0.1 mmol) by treatement with 1M NaOH and extraction with ether] in DCM (3 ml) di(tert-butyl) tricarbonate (26 mg, 0.1 mmol) was added, and the solution was set aside for 15 min. Methylamine (2M in DCM, 100 μl, 0.2 mmol) was added and the solution was left to stand over night. After evaporation the crude product was purified by preparative RP-HPLC using acetonitrile and water containing 0.1% TFA as mobil phase. The appropriate fraction was concentrated in vacuo and extracted with 1M NaOH and ether. The residue from the organic phase was acidified with 1M HCl and lyophilized from acetic acid to afford the title compound as a white amorphous solid (15 mg, 30%). The substance is a mixture of two diastereomeric pairs.

APCI-MS: m/z 420 [MH$^+$]

EXAMPLE 217

(2S,4S)-1-{3-[2-(Acetylamino)phenoxy]-2-hydroxypropyl}-4-(4-chlorophenoxy)-2-pyrrolidinecarboxylic acid; compound with trifluoroacetic acid (i) Methyl (2S,4S)-1-{3-[2-(acetylamino)phenoxy]-2-hydroxypropyl}-4-(4-chlorophenoxy)-2-pyrrolidinecarboxylate hydrochloride Methyl (2S,4S)-4-(4-chlorophenoxy)-2-pyrrolidinecarboxylate (370 mg, 1.0 mmol) and N-[2-(2-oxiranylmethoxy)phenyl]acetamide (207 mg, 1.0 mmol) dissolved in tert-butanol (7 ml) was stirred in a sealed vial at 100° C. over night. Workup of the crude material by flash chromatography on silica (DCM/MeOH 100/2), acidification of the appropriate fractions with 1M HCl and lyophilization from acetic acid afforded the subtitled compound as a white amorphous solid (360 mg, 72%). The substance is a diastereomeric mixture.

APCI-MS: m/z 463 [MH$^+$]

ii) (2S,4S)-1-{3-[2-(Acetylamino)phenoxy]-2-hydroxypropyl}-4-(4-chlorophenoxy)-2-pyrrolidinecarboxylic acid; compound with trifluoroacetic acid Compound (i) (50 mg, 0.1 mmol) was dissolved in acetonitrile (2 ml) and water (3 ml). Lithium hydroxide hydrate (8 mg, 0.2 mmol) dissolved in water (0.5 ml) was added. The reaction was complete after 0.5 h as determined by analytical HPLC. The mixture was acidified with TFA and purified by preparative RP-HPLC using acetonitrile and water containing 0.1% TFA as mobile phase. The appropriate fraction was concentrated in vacuo and the residue lyophilized from acetic acid to give the title compound as a white amorphous solid (27 mg, 48%). The substance is a diastereomeric mixture.

APCI-MS: m/z 449 [MH$^+$], 431 [MH$^+$, lactone, minor amount]

EXAMPLE 218

Ethyl (2S,4S)-1-{3-[2-(acetylamino)phenoxy]-2-hydroxypropyl}-4-(3,4-dichlorophenoxy)-2-pyrrolidinecarboxylate; trifluoroacetic acid salt i) Methyl (2S,4S)-4-(3,4-dichlorophenoxy)-2-pyrrolidinecarboxylate The compound was prepared by analogy with Example 217(ii) from N-Boc-cis-4-hydroxy-L-proline methylester and 3,4-dichlorophenol.

$^1$H-NMR (400 MHz, DMSO-d$_6$): δ 9.64 (bs, 2H); 7.58 (d, 1H); 7.25 (d, 1H); 6.94 (dd, 1H); 5.24 (m, 1H); 4.66 (dd, 1H); 3.76 (s, 3H); 3.55 (dd, 1H); 3.47 (d, 1H); 2.67–2.58 (m, 1H); 2.38 (d, 1H)

APCI-MS: m/z 290, 292 [MH$^+$, isotope pattern]

ii) Ethyl (2S,4S)-1-{3-[2-(acetylamino)phenoxy]-2-hydroxypropyl}-4-(3,4-dichlorophenoxy)-2-pyrrolidinecarboxylate; trifluoroacetic acid salt The compound was prepared by analogy with Example 217 from compound i) (404 mg, 1.0 mmol) and N-[2-(2-oxiranylmethoxy)phenyl]acetamide (207 mg, 1.0 mmol), with the exception that ethanol was used as solvent. Reesterification occurred, and after work-up and purification the title compound was isolated as a white solid (209 mg, 33%). The substance is a diastereomeric mixture.

APCI-MS: m/z 511, 513 [MH$^+$, isotope pattern]

EXAMPLE 219

N-[2-({(2S)-3-[(2S,4S)-4-(4-Chlorophenoxy)-2-(hydroxymethyl)pyrrolidinyl]-2-hydroxypropyl}oxy)phenyl]acetamide; trifluoroacetic acid salt and N-[2-({(2R)-3-[(2S,4S)-4-(4-Chlorophenoxy)-2-(hydroxymethyl)pyrrolidinyl]-2-hydroxypropyl}oxy)phenyl]acetamide; trifluoroacetic acid salt i) [(2S,4S)-4-(4-Chlorophenoxy)pyrrolidinyl]methanol Methyl (2S,4S)-4-(4-chlorophenoxy)-2-pyrrolidinecarboxylate prepared from cis-4-hydroxy-L-proline methylester according to Example 217ii)) (850 mg, 3.32 mmol) in dry THF (20 ml) was added during 40 min to a mixture of lithium aluminiumhydride (505 mg, 13.3 mmol) in dry THF (10 ml) at 0° C. under an argon atmosphere. After stirring overnight at room temperature sodium sulfate decahydrate (1 g) was added, followed by dropwise addition of water (0.5 ml), sodium hydroxide (15% w/v, 0.5 ml) and water (1.5 ml). Filtration and evaporation gave a syrup which was purified by flash chromatography on silica gel (dichloromethane/methanol/concentrated ammonia 100/20/1) to give the subtitle compounds (0.60 g, 79%).

$^1$H-NMR (400 MHz, CDCl$_3$): δ 7.22 (m, 2H), 6.78 (m, 2H), 4.79 (m, 1H), 3.62 (m, 2H), 3.39 (m, 1H), 3.23 (bd, 1H), 3.14 (dd, 1H, J 5.0 Hz, 12.2 Hz), 2.28 (m, 1H), 1.72 (m, 1H).

MS-APCI+: m/z 228 [MH$^+$]

ii) N-[2-({(2S)-3-[(2S,4S)-4-(4-Chlorophenoxy)-2-(hydroxymethyl)pyrrolidinyl]-2-hydroxypropyl}oxy)phenyl]acetamide; trifluoroacetic acid salt and N-[2-({(2)-3-[(2S,4S)-4-(4-Chlorophenoxy)-2-(hydroxymethyl)pyrrolidinyl]-2-hydroxypropyl}oxy)phenyl]acetamide; trifluoroacetic acid salt

[(2S,4S)-4-(4-Chlorophenoxy)pyrrolidinyl]methanol (380 mg, 1.67 mmol) and N-[2-(2-oxiranylmethoxy)phenyl]acetamide (414 mg, 2.00 mmol) were dissolved in tert-butanol (5 ml) and stirred in a sealed vial at 100° C. for 3 h. The solution was concentrated and the residue was purified by flash chromatography on silica gel (dichloromethane/methanol 13/1) followed by preparative RP-HPLC using acetonitrile/water containing 0.1% trifluoroacetic acid as mobile phase. The appropriate fractions were lyophilized to give the title compounds (epimer A: 248 mg, 27%, epimer B: 115 mg, 13%; stereochemistry at epimeric centre not determined).

Epimer A:

1H-NMR (400 MHz,MeOD): δ 7.82 (dd, 1H; J 1.3 Hz, 8.0 Hz), 7.31 (m, 2H), 7.14 (m, 1H), 7.04 (m, 1H), 6.96 (m, 3H), 5.20 (m, 1H), 4.40 (m, 1H), 4.11 (bd, 2H), 3.79–4.05 (m, 5H), 3.73 (dd, 1H, J 5.2 Hz, 12.5 Hz), 3.43 (dd, 1H, J 2.6 Hz, 13.0 Hz), 2.80 (m, 1H), 2.18 (s, 3H), 2.12 (m, 1H).

MS-APCI+: m/z 435 [MH$^+$]

Epimer B:

1H-NMR (400 MHz,MeOD): δ 7.79 (dd, 1H, J 1.3 Hz, 7.9 Hz), 7.32 (m, 2H), 7.14 (m, 1H), 7.04 (m, 1H), 6.97 (m, 3H), 5.18 (m, 1H), 4.49 (m, 1H), 3.83–4.19 (m, 7H), 3.69 (dd, 1H, J 4.8 Hz, 13.2 Hz), 3.34 (m, 1H), 2.72 (m, 1H), 2.18 (s, 3H), 2.07 (m, 1H).

MS-APCI+: m/z 435 [MH$^+$]

EXAMPLE 220

N-(2-{3-[3-(4-Chlorophenoxy)-1-pyrrolidinyl]-2-hydroxy-2-methylpropoxy}phenyl)acetamide hydrochloride i) N-{2-[(2-Methyl-2-propenyl)oxy]phenyl}acetamide The compound (1.74 g, 85%) was prepared from 3-chloro-2-methylpropene (1.09 g, 11.9 mmol) and 2-acetamidophenol (1.50 g, 9.92 mmol) analogously to that described in Example 8(i).

$^1$H-NMR (400 MHz, CDCl$_3$): δ 8.36 (dd, 1H, J 1.7 Hz, 7.8 Hz), 7.80 (bs, 1H), 6.98 (m, 2H), 6.87 (dd, 1H, J 1.6 Hz, 7.9 Hz), 5.08 (s, 1H), 5.04 (s, 1H), 4.51 (s, 2H), 2.21 (s, 3H), 1.85 (s, 3H).

ii) N-{2-[(2-Methyl-2-oxiranyl)methoxy]phenyl}acetamide

The compound (0.56 g, 65%) was prepared from N-{2-[(2-methyl-2-propenyl)oxy]phenyl}acetamide (800 mg, 3.90 mmol) and m-chloroperbenzoic acid (80%, 1.10 g, 5.22 mmol) analogously to that described in Example 8 (ii).

$^1$H-NMR (400 MHz, CDCl$_3$): δ 8.36 (m, 1H), 8.01 (bs, 1H), 7.01 (m, 2H), 6.91 (m, 1H), 4.07 (m, 2H), 2.96 (d, 1H, J 4.8 Hz), 2.79 (d, 1H, J 4.8 Hz), 2.22 (s, 3H), 1.49 (s, 3H).

iii) N-(2-{3-[3-(4-Chlorophenoxy)-1-pyrrolidinyl]-2-hydroxy-2-methylpropoxy}phenyl)acetamide hydrochloride The title compound (255 mg, 110%) was prepared from N-{2-[(2-methyl-2-oxiranyl)methoxy]phenyl}acetamide (123 mg, 0.557 mmol) and 3-(4-chlorophenoxy)pyrrolidine (100 mg, 0.506 mmol) analogously to that described in Example 1 (iii).

$^1$H-NMR (400 MHz, MeOD): δ 7.61 (m, 1H), 7.29 (m, 2H), 7.18 (m, 1H), 7.10 (m, 1H), 6.96 (m, 3H), 5.18 (m, 1H), 3.91–4.22 (m, 4H), 3.37–3.76 (m, 4H), 2.66 (m, ½H), 2.37 (m, 1H), 2.25 (m, ½H), 2.15 (m, 3H), 1.45 (m, 3H).

MS-APCI+: m/z 419 [MH$^+$]

GENERAL PROCEDURES AND PREPARATION OF STARTING MATERIALS FOR EXAMPLES 221–230

Preparation of the Epoxides:

A) N-(2-{[(2S*,3S*)-3-Methyloxiranyl]methoxy}phenyl)acetamide i) N-{2-[(E)-1-Propenyloxy]phenyl}acetamide A heterogenic mixture of commercially available 1-chloro-2-butene (Aldrich, predominantly trans) (453 mg, 0.49 mL, 5.00 mmol), 2-acetamidophenol (756 mg, 5.00 mmol) and potassium carbonate (691 mg, 5.00 mmol) in aceton (10 ml) was heated to reflux over night. After evaporation of the solvent the residue was taken up by ethylacetate and water. Washing of the organic phase with water, 5-proz. sodium hyroxide and brine and evaporation of the solvent afforded the crude which was purified by flash chromatography on silica gel (heptane/EtOAc=3:2). Yield: 732 mg (71%) of a brownish yellow solid.Trans: cis=81:19 (ratio determined by $^1$H-NMR; 400 MHz, CDCl$_3$):

MS-APCI+: m/z 206.1 [MH$^+$].

ii) M-chloroperbenzoic acid (70-proz.; 270 mg, 1.92 mmol, 2.0 equiv.) was added to a ice bath cooled solution of compound i) (112 mg, 546 μmol) dissolved in dichloromethane (3 ml) and stirred without further cooling over night. After addition of ethylacetate the mixture was washed with sat. sodium sulfite, 5-proz. sodium hyroxide and brine. Drying over sodium sulfate, evaporation of the solvent and flash chromatography on silica gel afforded 86 mg (71%) of the product as a beige solid in a trans:cis-ratio of 83:17 as determined by $^1$H-NMR.

$^1$H-NMR (400 MHz, CDCl$_3$; only the signals of the major isomer are given): δ 8.35 (1H, m), 7.90 (1H, br.s), 7.00 (2H, m), 6.88 (1H, m), 4.30 (1H, dd, J 11.4, 2.5 Hz), 3.96 (1H, dd, J 11.4, 5.7 Hz), 3.08 (2H, m), 2.21 (3H, s), 1.40 (3H, d, J 5.2 Hz).

MS-APCI+: m/z 222.1 [MH$^+$].

B) N-(2-{[(2S,3R)-3-Methyloxiranyl]methoxy}phenyl)acetamide i) N-[2-(2-Butynyloxy)phenyl]acetamide A mixture of 1-bromo-2-butine (1.39 g (10.4 mmol), 2-acetamidophenol (1.58 mg, 10.4 mmol), anhydrous potassium carbonate (1.44 g, 10.4 mmol) and sodium iodide (30 mg) in butanone (50 ml) was heated over night to reflux. After that the reaction mixture was filtrated, the filtrate was evaporated and the resulting residue was taken up by ethyl acetate. The obtained solution was washed with 5-proz. sodium hydroxide, brine and water, dried over sodium sulfate and evaporated. The crude was recrystallized out of heptane/MTB (1:1) yielding in 1.57 g (74%) of a light brown needles.

MS-APCI+: m/z 204.1 [MH+].

ii) N-{2-[(Z)-2-Butenyloxy]phenyl}acetamide

A mixture of the alkyne i) (357 mg, 1.76 mmol) and 5-% Pd/BaSO$_4$ (22 mg) in pyridine (2.0 mL) was hydrogenated for 2 h 30 min under atmospheric pressure at room temperature. At this point the starting material was completely consumed, but some overreduction to the corresponding alkane was observed by LC/MS. The reaction mixture was filtered on celite which was thoroughly washed with ethylacetate. Thereafter the filtrate was washed with 1 N HCl to acidic reaction and finally washed neutral with brine. Drying over sodium sulfate, evaporation of the solvent yielded in 318 mg (88%) crude which contained beside the desired Z-olefin also some E-olefin and corresponding alkane as biproducts. The ratio as determined by $^1$H-NMR (400 MHz, CDC$_3$) was E:Z:alkane 83:10:7. The crude was used in the next step without further purification.

MS-APCI+: m/z 206.1 [MH+].

iii) The olefine ii) (310 mg, 1.51 mmol) was dissolved in dichloromethane (10 ml) and m-chloroperbenzoic acid (80-proz.; 587 mg, 2.72 mmol, 1.8 equiv.) was added at 0° C. Stirring over night at ambient temperature was followed by evaporation of the solvent and taking up the resulting residue with ethylacetate, washing with sat. sodium sulfite, 5-% sodium hydroxide and brine and drying over sodium sulfate. Evaporation of the solvent and flash chromatography on silica gel (ethylacetate/heptane=2:1 continued to ethylacetate) gave 269 mg (81%) of the epoxide in a E:Z-ratio of 82:18 (determined by $^1$H-NMR) as a white powder.

$^1$H-NMR (400 MHz, CDCl$_3$; only the signals of the major isomer are given): δ 8.37 (1H, dd, J 7.5, 2.1 Hz), 7.81 (1H, br.s), 7.02 (2H, m), 6.91 (1H, dd, J 7.4, 1.7 Hz), 4.32 (1H, dd, J 11.1, 3.6 Hz), 4.03 (1H, dd, J 11.1, 6.9 Hz), 3.33 (1H, dt, J 7.0, 4.0 Hz), 3.24 (1H, dt, J 9.9, 5.5 Hz), 2.21 (3H, s), 1.38 (3H, d, J 5.7 Hz).

MS-APCI+: m/z 222.1 [MH+].

C) N-{2-[(1R,2S,5R)*-6-Oxabicyclo[3.1.0]hex-2-yloxy]phenyl}acetamide i) (2-Cyclopenten-1-yloxy)(triisopropyl)silane A solution of 2-cyclopentenol (K. Alder, F. H. Flock, Chem. Ber. 1956, 89, 1732.) (2.31 g, 27.5 mmol), (triisopropyl)chlorsilane (5.30 g, 5.9 mL, 27.5 mmol), imidazole (2.06 g, 30.2 mmol) in DMF (50 mL) was stirred at room temperature for 3h and for an additional hour at 50° C. Then the solution was diluted with ethylacetate, washed 4 times with water and dried over sodium sulfate. Evaporation of the solvent yielded in 6.32 g (96%) of the silylether 513/13 as a colourless liquid. No major impurities were visible in the $^1$H-NMR-spectrum.

$^1$H-NMR (400 MHz, CDCl$_3$): δ 5.88 (1H, m), 5.76 (1H, m), 4.98 (1H, m), 2.48 (1H, m), 2.27–2.17 (2H, m), 1.70 (1H, m), 1.12–1.05 (21H, m).

ii) Triisopropyl[(1R,2R,5R)*-6-oxabicyclo[3.1.0]hex-2-yloxy]silane

M-chloroperbenzoic acid (70-%.; 5.41 g, 21.9 mmol, 1.7 equiv.) was added to a ice bath cooled solution of compound i) (3.10 g, 12.9 mmol) dissolved in dichloromethane (25 ml) and stirred without further cooling additional 90 min. After filtration of the reaction mixture, evaporation of the filtrate the residue was dissolved in ethylacetate, washed with sat. sodium sulfite, 5-proz. sodium hydroxide and brine and dried over sodium sulfate. Evaporation of the solvent afforded the crude as a mixture of the diastereomeric epoxides in trans/cis-ratio of 78:22 ($^1$H-NMR). Separation by flash chromatography on silica gel (heptane/ethylacetate=95:5 continued to 90:10) afforded 1.65 g (50%)

of the desired trans-epoxide (1R,2R,5R)* as the first eluated diastereomer. The total yield of both diastereomeric epoxides was 2.86 g (87%).

$^1$H-NMR (400 MHz, CDCl$_3$): δ 4.39 (1H, d, J 3.4 Hz), 3.54 (1H, d, J 2.5 Hz), 3.37 (1H, d, J 2.5 Hz), 1.94 (1H, m), 1.84 (dtd, J 13.7, 9.3, 1.1 Hz), 1.60–1.55 (2H, m), 1.13–1.04 (21H, m).

iii) (1S,2R,5R)*-6-Oxabicyclo[3.1.0]hexan-2-ol

To a solution of the silylether ii) (280 mg, 1.09 mmol) in THF (2.0 mL) tetrabutylammonium fluorid (1.0 M in THF; 1.2 mL, 1.20 mmol) was added. After stirring for 3 h at room temperature the mixture was diluted with ethylacetate, washed with brine and dried over sodium sulfate. Chromatographic filtration on silica gel (heptane/tertbutylmethylether 2:1 continued to ethylacetate) afforded 79 mg (72%) as a pale yellow oil.

$^1$H-NMR (400 MHz, CDCl$_3$): δ 4.36 (1H, d, J 5.1 Hz), 3.55 (1H, s), 3.42 (1H, J 1.5Hz), 1.99 (1H, m), 1.84 (1H, dddd, J 13.9, 10.1, 9.0, 1.1 Hz), 1.69–1.53 (3H, m).

iv) The title compound was prepared according to the general protocol (I) below.

$^1$H-NMR (400 MHz, CDCl$_3$): δ 8.38 (1H, m), 7.91 (1H, br.s), 7.02–6.98 (2H, m), 6.94 (1H, m), 4.78 (1H, td, J 8.0, 1.2 Hz), 3.61 (1H, m), 3.54 (1H, d, J 2.7 Hz), 2.21 (3H, s), 2.21 (1H, m), 2.10 (1H, dt, J 12.8, 12.0 Hz), 1.76 (H, dtd, J 14.3, 10.4, 1.4 Hz), 1.58 (1H, m).

MS-APCI+: m/z 234.1 [MH+].

General Protocol (I) for the Preparation of N-{2-[(1R,2S,5R)*-6-oxabicyclo[3.1.0]hex-2-yloxy]phenyl}acetamides Step 1—Mitsunobu Coupling To a ice bath cooled solution of the epoxyalcohol 546/16 (1.0 equiv.), triphenylphosphine (1.2 equiv.) and a 2-nitrophenol (1.0 equiv.) in dry THF (2 mL/mmol) diethyl diazodicarboxylic acid (1.2 equiv.) was added dropwise. Stirring was continued over night without further cooling. Aqueous, basic workup, followed by flash chromatography on silica gel (typical eluant: heptane/ethyl acetate=1:1) afforded the 2-nitrophenolic esters which contained often an equimolar amount of the biproduct diethyl 1,2-hydrazinedicarboxylate.

Step 2—Hydrogenation

A mixture of 2-nitrophenolic esters as obtained from step 1, diisopropyl(ethyl)amine (2.0 equiv.), acetic acid anhydrate (2.0 equiv.) and 5-proz. Pt/C (10 mg/mmol) in ethyl acetate (10 mL/mmol) was hydrogenated for 1 h under atmospheric pressure at room temperature. In the case of non-halogenated aromates Pd/C and shorter reaction times, typically about 5 min, could be applied. Thereafter the catalysator was filtered off by a celite filled filter funnel and washed with ethanol. The filtrate was evaporated and the remaining residue was subjected an aqueous, basic work-up. Subsequent flash chromatography on silica gel (typical eluant: ethyl acetate/heptane=2:1) afforded the respective acetamides in typical yields of 50–70% (2 steps).

D) N-{5-Chloro-2-[(1R,2S,5R)*-6-oxabicyclo[3.1.0]hex-2-yloxy]phenyl}acetamide

Preparation according to protocol (I).

$^1$H-NMR (400 MHz, CDCl$_3$): δ 8.47 (1H, d, J 2.5 Hz), 7.89 (1H, br.s), 6.97 (1H, dd, J 8.8, 2.5 Hz), 6.85 (1H, d, J 8.8 Hz), 4.74 (1H, td, J 8.0, 1.3 Hz), 3.58 (1H, m), 3.56 (1H, m), 2.21 (1H, m), 2.21 (3H, s), 2.09 (dt, J 13.0, 7.4 Hz), 1.76 (1H, dtd, J 14.3, 10.1, 1.3 Hz), 1.56 (1H, m)

MS-APCI+: m/z 268.0 [MH+].

E) N-{4-Fluoro-2-[(1R,2S,5R)*-6-oxabicyclo[3.1.0]hex-2-yloxy]phenyl}acetamide

Preparation according to protocol (I).

$^1$H-NMR (400 MHz, CDCl$_3$): δ 8.23 (1H, dd, J 10.7, 2.8 Hz), 7.99 (1H, br.s), 6.89 (1H, dd, J 9.0, 5.5 Hz), 6.69 (1H, ddd, J 11.1, 9.0, 3.1 Hz), 4.70 (1H, t, J 7.8 Hz), 3.56 (2H, s), 2.21 (1H, dd, J 14.7, 8.4 Hz), 2.21 (3H, s), 2:08 (1H, dt, J 13.0, 8.2 Hz), 1.75 (1H, dtm, J 14.3. 9.5 Hz).

MS-APCI+: m/z 252.1 [MH+].

General Protocol (II) for the Addition of Aminocycles to Substituted 2-(aryloxymethyl)oxiranes Equimolar amounts of aminocycle and epoxide, dissolved in a saturated solution of LiClO$_4$ in acetonitrile (1 ml/100 μmol), were heated to 100° C. in a sealed tube. Typical reaction times ranged from 3 h for open chained epoxides to 18 h for oxabicyclo[3.1.0]hexanes. After cooling down to ambient temperature the reaction mixture was diluted with ethyl acetate and subjected to an aqueous work-up. The crude products were usually obtained in quantitative yields and were purified by flash chromatography on silica gel (typical eluants: ethyl acetate/methanol=80:20).

The Examples 221–230 below were prepared according to the general protocols (I) and (II).

EXAMPLE 221

N-(2-{(1S,2R*,3S*)-3-[3-(4-Chloro-phenoxy)-pyrrolidin-1-yl]-2-hydroxy-cyclopentyloxy}-phenyl)-acetamide $^1$H-NMR (400 MHz, CDCl$_3$): δ 8.20 (1H, d, J 7.4 Hz), 8.07 (1H, br.s), 7.21 (2H, m), 7.01–6.96 (2H, m), 6.92 (1H, dm, J 7.4 Hz), 6.77 (2H, dm, J 8.8 Hz), 4.77 (1H, m), 4.54 (1H, br. q, J 4.8 Hz), 4.15 (1H, m), 3.04–2.91 (3H, m), 2.81 (1H, q, J 6.8 Hz), 2.62 (1H, quint, J 7.3 Hz), 2.29 (1H, m), 2.16 (3H, s), 2.13–1.90 (5H, m),1.63 (1H, m).

MS-APCI+: m/z 431.2 [MH+].

EXAMPLE 222

N-(2-{(1R*;2R*,3S*)-3-[3-(4-Chloro-phenoxy)-pyrrolidin-1-yl]-2-hydroxy-cyclopentyloxy}-phenyl)-acetamide $^1$H-NMR (400 MHz, CDCl$_3$): δ 8.26 (1H, m), 7.90 (1H, br.d, J 9.5 Hz), 7.20 (2H, m), 6.97 (2H, m), 6.88 (1H, br.d, J 7.3 Hz), 6.76 (2H, m), 4.76 (1H, m), 4.50 (1H, m), 4.21 (1H, dt, J 14.1, 5.5 Hz), 3.00–2.89 (3H, m), 2.67–2.54 (2H, m), 2.28 (1H, m), 2.15 (3H, s), 2.11 (1H, m), 1.97 (2H, m), 1.87 (2H, m).

MS-APCI+: m/z 431.2 [MH+].

EXAMPLE 223

N-(2-{(2R*,3R*)-3-[4-(3,4-Dichloro-phenoxy)-piperidin-1-yl]-2-hydroxy-butoxy}-phenyl)-acetamide $^1$H-NNR (400 MHz, CDCl$_3$): δ 8.27 ((1H, dd, J 7.6, 1.6 Hz), 8.07 (1H, br.s), 7.30 (1H, d, J 8.8 Hz), 7.04–6.92 (4H, m), 6.74 (1H, dd, J 8.8, 2.9 Hz), 4.26 (1H, m), 4.23 (1H, dd J 9.9, 2.7 Hz), 4.06 (1H, m), 3.96 (1H, dd, J 9.9, 8.0 Hz), 2.86–2.72 (3H, m), 2.58 (1H, m), 2.47 (1H, m), 2.18 (3H, s), 1.99 (2H, m), 1.80 (2H, m), 1.12 (3H, d, J 6.9 Hz).

MS-APCI+: m/z 469.1 [MH+].

EXAMPLE 224

N-(2-{(1S*,2R*,3S*)-3-[4-(4-Chloro-phenoxy)-piperidin-1-yl]-2-hydroxy-cyclopentyloxy}-phenyl)-acetamide $^1$H-NMR (400 MHz, CDCl$_3$): δ 8.26 (1H, m), 8.20 (1H, br.s), 7.19 (2H, m), 7.02 (2H, m), 6.95 (1H, m), 6.84 (2H, m), 4.49 (1H, q, J 5.2 Hz), 4.31 (1H, m), 4.15 (1H, m), 2.95 (2H, q, J 7.8 Hz), 2.87 (1H, m), 2.51 (2H, br.q, J 10.2 Hz), 2.19 (3H, s), 2.10–1.95 (5H, m), 1.86 (2H, m), 1.60 (1H, m).

MS-APCI+: m/z 445.0 [MH+].

EXAMPLE 225

N-(2-{(2R*,3S*)-3-[4-(3,4-Dichloro-phenoxy)-piperidin-1-yl]-2-hydroxy-butoxy}-phenyl)-acetamide $^1$H-NMR (400 MHz, CDCl$_3$): δ 8.47 (1H, br.s), 8.36 (1H, dd, J 7.2, 1.3 Hz), 7.32 (1H, d, J 9.0), 7.04–6.93 (4H, m), 6.75 (1H, dd, J 9.0, 2.9 Hz), 4.34 (1H, m), 4.11 (1H, m), 3.96 (1H, dd, J 10.5, 5.2 Hz), 3.66 (1H, m), 3.00–2.80 (2H, m), 2.71 (2H, m), 2.42 (1H, m), 2.19 (3H, s), 2.05 (1H, m), 1.94–1.81 (2H, m), 1.08 (3H, d, J 6.7 Hz).

MS-APCI+: m/z 466.9 [MH+].

EXAMPLE 226

N-(2-{(2R*,3R*)-3-[3-(4-Chloro-phenoxy)-pyrrolidin-1-yl]-2-hydroxy-butoxy}-phenyl)-acetamide $^1$H-NMR (400 MHz, CDCl$_3$): δ 8.34 (1H, t, J 4.5 Hz), 8.18 (1H, br.s), 7.22 (2H, m), 6.99 (2H, m), 6.93 (1H, m), 6.76 (2H, m), 4.78 (1H, m), 4.20 (1H, m), 4.07 (1H, dt, J 10.1, 2.9 Hz), 3.95 (1H, dd, J 10.1, 8.2 Hz), 3.15 (0.5H, dd, J 10.7, 6.1 Hz), 2.97–2.94 (1.5H, m), 2.89 (0.5H, q, J 7.6 Hz), 2.82 (0.5H, dd, J 10.5, 2.5 Hz), 2.73 (0.5H, qm, J 7.5 Hz), 2.65 (0.5H, m), 2.58 (1H, m), 2.26 (1H, m), 2.01 (1H, m), 1.09 (3H, appears as dd, J 6.7, 1.7 Hz).

MS-APCI+: m/z 419.1 [MH+].

EXAMPLE 227

N-(2-{(2R*,3S*)-3-[3-(4-Chloro-phenoxy)-pyrrolidin-1-yl]-2-hydroxy-butoxy}-phenyl)-acetamide $^1$H-NMR (400 MHz, CDCl$_3$): δ 8.48 (1H, m), 8.37 (1H, m), 7.22 (2H, m), 7.04–6.93 (3H, m), 6.77 (2H, m), 4.80 (1H, m), 4.12 (1H, m), 3.97 (1H, dd, J 10.5, 5.3 Hz), 3.65 (1H, m), 3.09 (0.5H, dd, J 10.3, 6.0 Hz), 3.06–2.99 (1.5H, m), 2.94 (0.5H, q, J 8.0 Hz), 2.87–2.67 (2.5H, m), 2.25 (1H, m), 2.02 (1H, m), 1.05 (3H, appears as dd, J 6.7, 5.2 Hz).

MS-APCI+: m/z 418.9 [MH+].

EXAMPLE 228

N-(2-{(1S*,2R*,3S*)-3-[4-(3-Chloro-phenoxy)-piperidin-1-yl]-2-hydroxy-cyclopentyloxy}-phenyl)-acetamide $^1$H-NMR (400 MHz, CDCl$_3$): δ 8.25 (1H, m), 8.17 (1H, br.s), 7.18 (1H, t, J 8.1Hz), 7.01 (2H, m), 6.97–6.90 (3H, m), 6.79 (1H, dm, J 9.0 Hz), 4.48 (1H, q, J 5.5 Hz), 4.34 (1H, hept, J 3.5 Hz), 4.15 (1H, dd, J 7.2, 5.5 Hz), 2.95 (2H, q, J 7.4 Hz), 2.87 (1H, m), 2.52 (2H, br.q), J 9.6 Hz), 2.19 (3H, s), 2.09–1.94 (6H, m), 1.86 (2H, m), 1.59 (1H, m).

MS-APCI+: m/z 445.1 [MH+].

EXAMPLE 229

N-[5-Chloro-2-({(1S,2R,3S)*-3-[4-(3,4-dichlorophenoxy)-1-piperidinyl]-2-hydroxycyclopentyl}oxy)phenyl]acetamide $^1$H-NMR (400 Mz, CDCl$_3$): δ 8.38 (2H, m), 7.31 (1H, d, J 8.7 Hz), 6.99 (1H, d, J 8.8 Hz), 6.95 (1H, dd, J 8.8, 2.6 Hz), 6.86 (1H, d, J 8.8 Hz), 6.75 (1H, dd, J 8.8, 2.9 Hz), 4.38 (1H, q, J 4.0 Hz), 4.31 (1H, hept, J 3.7 Hz), 4.10 (1H, dd, J≈7, 6 Hz), 3.00 (1H, q, J 7.1 Hz), 2.91–2.82 (1H, m), 2.53 (2H, m), 2.17 (3H, s), 2.08–1.93 (5H, m), 1.85 (2H, m), 1.60 (1H, m).

MS-APCI+: m/z 513.1 [MH+].

EXAMPLE 230

N-[4-Fluoro-2-({(1S,2R,3S)*-3-[4-(3,4-dichlorophenoxy)-1-piperidinyl]-2-hydroxycyclopentyl}oxy)phenyl]acetamide $^1$H-NMR (400 MHz, CDCl$_3$): δ 8.58 (1H, br.s), 8.19 (1H, dd, J 10.9, 3.2 Hz), 7.31 (1H, d, J 8.8 Hz), 7.00 (1H, d, J 2.9 Hz), 6.89 (1H, dd, J 9.0, 5.2 Hz), 6.75 (1H, dd, J 9.0, 2.9 Hz), 6.67 (1H, td, J 8.8, 3.1 Hz), 4.35–4.29 (2H, m), 4.09 (1H, dd, J 7.8, 5.0 Hz), 3.04 (1H, q, J 7.8 Hz), 2.88 (2H, m), 2.54 (2H, m), 2.18 (3H, s), 2.08 (5H, m), 1.85 (2H, m), 1.61 (1H, m).

MS-APCI+: m/z 497.2 [MH+].

Preparation of Starting Materials for Examples 231–248

A) (S*R*)-1-(3,4-Dichloro-benzyl)-2,5-dimethyl-piperazine

A solution of 1,2-dichloro-4-chloromethyl-benzene (1.1 ml 7.89 mmol) in DMF (5 ml) was added to 2,5-dimethyl-piperazine (1.0 g, 8.77 mmol) dissolved in DMF (25 ml). The reaction was stirred over night, poured into a mixture of EtOAc and sodium carbonate (5%). The water phase was washed twice with EtOAc and the combined organic phase once with brine, and dried over sodium sulfate. After evaporation the crude was dissolved in methanol. The dibensylated piperazine does not dissolve. The filtrate was filtered through a short silica column, using methanol as eluant and evaporated to give the pure product. Yield 812 mg, 38%

$^1$H-NMR (400 MHz, DMSO-d6): δ 7.56 (d, 1H, J=8.1 Hz), 7.52 (d, 1H, J=1.8 Hz), 7.20 (dd, 1H, J=8.2, 1.8 Hz), 3.97 (d, 1H, J=14.1 Hz), 3.04 (d, 1H, J=14.2 Hz), 2.76 (dd, 1H, J=11.9, 3.0 Hz), 2.59 (m), 2.48 (dd, 1H, J=11.9, 2.6 Hz), 2.37 (t, 1H, J=10.8 Hz), 2.12 (m), 1.89 (s), 1.57 (t, 1H, J=10.4 Hz), 1.00 (d, 1H, J=6.1 Hz), 0.82 (d, 1H, J=6.3 Hz).

APCI-MS: m/z 273 [M$^+$]

B) (S*R*)-1-(4-Chloro-benzyl)-2,5-dimethyl-piperazine

Was synthesized in the same way as A) from 1-chloro-4-chloromethyl-benzene (1.27 g, 7.89 mmol) and 2,5-dimethyl-piperazine (1.0 g, 8.77 mmol) in DMF. Yield 701 mg, 37%

$^1$H-NMR (400 MHz, DMSO-d6): δ 7.36 (d, 2H, J 8.4 Hz), 7.30 (d, 2H, J=8.4 Hz), 3.97 (d, 1H, J=13.9 Hz), 3.01 (d, 1H, J=13.8 Hz), 2.75 (dd, 1H, J=11.9, 3.0 Hz), 2.57 (m, 1H, J=10.8, 2.6 Hz), 2.47 (dd, 1H, J=10.9, 2.6 Hz), 2.36 (dd, 1H, J=11.6, 10.1 Hz), 2.10 (m, 1H), 1.88 (bs, 1H), 1.53 (t, 1H, J=10.5 Hz), 1.01 (d, 3H, J=6.1 Hz), 0.80 (d, 3H, J=6.4 Hz).

APCI-MS: m/z 239 [MH$^+$]

C) 1-(3,4-Chlorobenzyl)piperazine 3,4-chlorobenzyl chloride (170 mg, 0.872 mmol) was added to a solution of piperazine (150 mg, 1.74 mmol) and triethyl amine (1 ml) in DMF (10 ml) at room temperature. After 2 hrs the solution was concentrated in vacuo. The resulting residue was triturated under ether and the obtained solid was washed with water and then dissolved in methanol and co-evaporated with toluene to give the product, 89 mg, as a solid.

APCI-MS: m/z 245, 247 [MH$^+$]

$^1$HNMR (400 MHz, CD$_3$OD) δ 7.41 (d, 1H, J=2.0 Hz), 7.37 (d, 1H, J=8.2 Hz), 7.13 (dd, 1H, J=8.2, J=2.0 Hz), 3.5 (s, 2H), 3.05 (m, 4H), 2.57 (m, 4H)

D) 1-(4-Chlorobenzyl)piperazine

Was prepared by analogy to C) above.

EXAMPLE 231

N-(2-{3-[4-(3,4-Dichlorobenzyl)-1-piperazinyl]-2-hydroxypropoxy}-phenyl)acetamide dihydrochloride A solution of N-acetyl-2-(2,3-epoxypropoxy)aniline (87.53 mg, 0.422 mmol) and 1-(3,4-chlorobenzyl)piperazine in ethanol (10 ml 99.5%) was refluxed for 3 hrs. The solvent was distilled off under reduced pressure and the resulting residue was purified by silica gel column chromatography (dichloromethane/methanol 20:1) to give the title compound as a gum. Addition of 11.0M ethereal HCl solution gave a white solid product 78 mg (40%).

APCI-MS: m/z 452, 454 [MH$^+$]

$^1$HNMR (400 MHz, CD$_3$OD) δ 8.0 (1H, dd, J=1.53 Hz, J=8.01 Hz), 7.5 (1H, d, J=1.91 Hz), 7.45 (1H d, J=8.2 Hz), 7.23 (1H, dd, J=6.1 Hz, J=2.1 Hz), 6.89–7.08(4H, m), 4.15(1H, m), 3.9–4.1 (2H, m), 3.48 (2H, S) 2.45–2.60 (10H, m), 2.17 (3H, S).

Examples 232–248 were synthesized according to example 231 with the starting materials A) to D) above.

EXAMPLE 232

N-(2-{3-[4-(3,4-Dichlorobenzyl)-1-piperazinyl]-2-hydroxypropoxy}-4-fluorophenyl)acetamide APCI-MS: m/z 470 [MH$^+$]

EXAMPLE 233

N-(2-{3-[4-(3,4-Dichlorobenzyl)-2,5-dimethyl-1-piperazinyl]-2-hydroxypropoxy}phenyl)acetamide APCI-MS: m/z 480 [MH$^+$]

EXAMPLE 234

N-(5-Chloro-2-{3-[4-(3,4-dichlorobenzyl)-1-piperazinyl]-2-hydroxypropoxy}phenyl)acetamide APCI-MS: m/z 486 [MH$^+$]

EXAMPLE 235

N-(5-Chloro-2-{3-[4-(3,4-dichlorobenzyl)-2,5-dimethyl-1-piperazinyl]-2-hydroxypropoxy}phenyl)acetamide APCI-MS: m/z 480 [MH$^+$]

EXAMPLE 236

N-(2-{3-[4-(3,4-Dichlorobenzyl)-2,5-dimethyl-1-piperazinyl]-2-hydroxypropoxy}-4-methylphenyl)acetamide APCI-MS: m/z 494 [MH$^+$]

EXAMPLE 237

N-(2-{3-[4-(3,4-Dichlorobenzyl)-2,5-dimethyl-1-piperazinyl]-2-hydroxypropoxy}-4-fluorophenyl)acetamide APCI-MS: m/z 498 [MH$^+$]

EXAMPLE 238

N-(2-{3-[(S*R*)-4-(3,4-Dichlorobenzyl)-2,5-dimethyl-1-piperazinyl]-2-hydroxypropoxy}phenyl)acetamide APCI-MS: m/z 480 [MH$^+$]

EXAMPLE 239

N-(2-{3-[(S*R*)-4-(4-Chlorobenzyl)-2,5-dimethyl-1-piperazinyl]-2-hydroxypropoxy}phenyl)acetamide APCI-MS: m/z 446 [MH$^+$]

EXAMPLE 240

N-(5-Chloro-2-{3-[(S*R*)-4-(3,4-dichlorobenzyl)-2,5-dimethylpiperazinyl]-2-hydroxypropoxy}phenyl)acetamide APCI-MS: m/z 514 [MH$^+$]

EXAMPLE 241

N-(-Chloro-2-{3-[(S*R*)-4-(4-chlorobenzyl)-2,5-dimethylpiperazinyl]-2-hydroxypropoxy}phenyl)acetamide APCI-MS: m/z 480 [MH$^+$]

EXAMPLE 242

1-(5-Chloro-2-{3-[4-(4-chlorobenzoyl)-1-piperazinyl]-2-hydroxypropoxy}phenyl)-1-ethanone APCI-MS: m/z 451 [MH$^+$]

EXAMPLE 243

N-(5-Cyano-2-{3-[(S*R*)-4-(3,4-dichlorobenzyl)-2,5-dimethylpiperazinyl]-2-hydroxypropoxy}phenyl)acetamide APCI-MS: m/z 505 [MH$^+$]

EXAMPLE 244

N-(2-{3-[(S*R*)-4-(4-Chlorobenzyl)-2,5-dimethylpiperazinyl]-2-hydroxypropoxy}-5-cyanophenyl)acetamide APCI-MS: m/z 471 [MH$^+$]

EXAMPLE 245

N-(5-Chloro-2-{3-[4-(4-chlorobenzyl)-1-piperazinyl]-2-hydroxypropoxy}-phenyl)acetamide APCI-MS: m/z 452 [MH$^+$]

EXAMPLE 246

N-(4-Chloro-2-{3-[4-(4-chlorobenzyl)-2,5-dimethyl-1-piperazyl]-2-hydroxypropoxy}phenyl)acetamide APCI-MS: m/z 460 [MH$^+$]

EXAMPLE 247

N-(2-{3-[4-(4-Chlorobenzoyl)-1-piperazinyl]-2-hydroxypropoxy}-5-cyanophenyl)acetamide APCI-MS: m/z 457 [MH$^+$]

EXAMPLE 248

N-(2-{3-[4-(4-Chlorobenzoyl)-1-piperazinyl]-2-hydroxypropoxy}-4-methylphenyl)acetamide APCI-MS: m/z 446 [MH$^+$]

EXAMPLE 249

N-[5-Chloro-2-({(1R,2S,3R)-3-[(3S)-3-(4-chlorophenoxy)pyrrolidinyl]-2-hydroxycyclopentyl}oxy)phenyl]acetamide MS-APCI+: m/z 464.9 [MH+].

[α]$^{22}$=−47.6 (CH$_2$C$_2$).

EXAMPLE 250

N-{2-[(2S)-(3-{(3S)-3-[(4-Chlorophenyl)oxy]-1-pyrrolidinyl}-2-hydroxypropyl)oxy]-4-fluorophenyl}acetamide APCI-MS: m/z 423.1 [M+]

EXAMPLE 251

N-[2-({(2S)-3-[(3S)-3-(4-Chlorobenzyl)pyrrolidinyl]-2-hydroxypropyl}oxy)phenyl]acetamide hydrochloride i) 3-(4-Chlorobenzyl)pyrrolidine To a solution of 3-(4-chlorobenzyl)-2-pyrrolidinone (420 mg, 2 mmol) in dry THF (25 mL) and under $N_2$ LAH (190 mg, 5 mmol) was added in portions with stirring over a period of a couple of minutes. The temperature was increased to 60° C. and the stirring continued for 2.5 h. The mixture was quenched with 200 µL water, 200 µL 5M NaOH and 600 µL water. The solid Li- and Al-salts were filtered off and the filtrate was evaporated to give a colourless oil (387 mg, 99%).

APCI-MS: m/z 196, 198 [MH+]

ii) (2S)-1-[3-(4-Chlorobenzyl)-1-pyrrolidinyl]-3-(2-nitrophenoxy)-2-propanol

A solution of compound (i) (387 mg, 2 mmol) and (2S)-2-[(2-nitrophenoxy)-methyl]oxirane (390 mg, 2 mmol) in ethanol (6 mL) was refluxed until the reaction was complete (2 h), as determined by LCMS. The solvent was evaporated to give an orange oil (650 mg, 83%) which was used without further purification.

APCI-MS: m/z 391, 393 [MH+]

ii) (2S)-1-(2-Aminophenoxy)-3-[3-(4-chlorobenzyl)-1-pyrrolidinyl]-2-propanol

To a solution of compound (ii) (650 mg, 1.67 mmol) in ethanol (10 mL) at 60° C. a mixture of tin(II)chloride dihydrate (2.25 g, 10 mmol) and 35% hydrochloric acid (2.5 mL) was added. The temperature increased rapidly to 75° C. The mixture was stirred at 60° C. for further 30 min. After evaporation of the solvent the residue was extracted with 5M NaOH and ether. The organic phase was washed with water, dried and evaporated. The residue was purified by RP-HPLC with acetonitrile and water containing 0.1% TFA as mobile phase. The appropriate fraction was evaporated and the residue extracted with 1M NaOH and ether. The subtitle compound was obtained from the organic phase as a colourless oil (400 mg, 66%).

APCI-MS: m/z 361, 363 [MH+]

iv) To a solution of compound (iii) (400 mg, 1.1 mmol) in DCM (10 mL) acetic anhydride (200 µL, 2.1 mmol) was added and the mixture was left overnight. After evaporation the residue was dissolved in methanol and 1.5M sodium-methoxid in methanol (2 mL) was added. The mixture was left for 2 h, evaporated and taken up in ether and water. A mixture of the two diastereomers was obtained from the organic phase. The diastereomers were separated by HPLC on a chiral column using a mixture of isohexane, 2-propanol and methanol as mobile phase. The isolated enantiomers were dissolved in methanol (1 mL), acidified with 1M hydrochloric acid (1 mL), diluted with water and lyophilized to give the title compounds as white amorphous solids (156 mg and 173 mg).

The absolute stereoisomerism was not assigned.

APCI-MS: m/z 403, 405 [MH+]

EXAMPLE 252

N-(5-Chloro-2-{3-[3-(4-chloro-benzyl)-pyrrolidin-1-yl]-2-hydroxy-propoxy}-phenyl)-acetamide trifluoroacetic acid salt i) 3-(4-Chloro-benzyl)-pyrrolidin-2-one In a flask was added diisopropylamine (3.22 g, 31.8 mmole) and dry THF (60 ml). The content of the flask was kept under nitrogen, and was then cooled to −76° C. To the cool solution was dropwise added n-butyllithium (n-BuLi, 32 mmole, 20 ml, 1.6 M in hexane). After completed addition, the solution was stirred for 10 minutes, and a solution of 1-Trimethylsilanyl-pyrrolidin-2-one (5.00 g, 31.8 mmole, prepared according to literature methods) in dry THF (5 ml) was added dropwise. The solution was then stirred for an additional 20 minutes and a solution of 4-Chlorobenzyl chloride (5.13 g, 32 mmole) in THF (5 ml) was added via a syringe during 5 minutes. The resulting mixture was stirred at −76° C. for 1 hour, and was then allowed to reach the ambient temperature and was stirred over night. Water (40 ml) was added and the mixture was stirred vigorously for 60 minutes. The phases were separated and the organic phase was washed with brine, and was finally evaporated, giving an oil which crystallized on standing. The solid was triturated with heptane:EtOAc 2:1 and was filtered, giving a partly purified solid. The solid was purified on silica (DCM to DCM:MeOH 99:1 to 98:2 to 97:3 gradient) giving 1.3 g (20%) of the sub-title compound.

$^1$H-NMR (400 MHz, CDCl$_3$) δ: 7.27 (2H, d, J 8.4 Hz); 7.16 (2H, d, J 8.4 Hz); 5.43 (1H, bs); 3.31–3.13 (3H, m); 2.74–2.61 (2H, m); 2.20–2.12 (1H, m); 1.88–1.77 (1H, m)

ii) 3-(4-Chloro-benzyl)-pyrrolidine

In a flask was dissolved the compound obtained in a) (0.20 g, 0.95 mmole), in dry THF (10 ml). LiAlH$_4$ (0.17 g, 4.53 mmole) was added in small portions over 10 minutes. After completed addition, the mixture was heated to 60° C. for approximately 3 h under nitrogen, and the reaction was monitored by LC-MS, and was quenched after completed reaction. Before quenching, the reaction was allowed to reach the ambient temperature, and water (0.160 ml) was added cautiously drop by drop. NaOH (10% solution in water, 0.16 ml) was added dropwise, and finally another portion of water (0.48 ml). The mixture was stirred for 1 hour and was then filtered. The filtrate was concentrated in vaccuo giving the sub-title compound (0.18 g, 97%) as a colorless oil.

APCI-MS: m/z 196.1 [M+H]

iii) N-(5-Chloro-2-{3-[3-(4-chloro-benzyl)-pyrrolidin-1-yl]-2-hydroxy-propoxy}-phenyl)-acetamide trifluoroacetic acid salt The title compound was prepared according to the method described in Example 1 iii) from the compound obtained in ii).

$^1$H-NMR (400 MHz, DMSO) δ: 9.93–9.62 (1H, m); 9.12 (1H, s); 8.11 (1H, s); 7.38 (2H, d, J 8.9 Hz); 7.29–7.23 (2H, m); 7.13–7.02 (2H, m); 6.11–6.02 (1H, m); 4.29–4.16 (1H, bs); 4.05–3.95 (1H, m); 3.95–3.87 (1H, m); 3.75–3.50 (2H, m); 3.40–3.22 (3H, m); 2.91–2.65 (3H, m); 2.62–2.52 (1H, m); 2.13 (3H, s); 2.11–1.94 (1H, m); 1.81–1.55 (1H, m)

EXAMPLE 253

N-(2-{3-[3-(4-Chlorophenoxy)-1-pyrrolidinyl]-2-hydroxypropoxy}-4-methylphenyl)-1-pyrrolidinecarboxamide trifluoroacetate i) 2-[(5-Methyl-2-nitrophenoxy)methyl]oxirane A mixture of 5-Methyl-2-nitrophenol (7.7 g, 50 mmol), potassium carbonate (13.8 g, 0.1 mmol) and epibromohydrine (8.25 mL, 0.1 mmol) was dissolved in DMF (100 mL) and stirred 2–3 h at 100° C. under an atmosphere of nitrogen. The mixture was diluted with ether (0.5 L) and extracted with water until pH=7. The organic phase was evaporated and the residue was purified by flash-chromatography on silica (DCM) to give the sub-title compound as a yellow solid (8.65 g, 83%).

¹H-NMR (400 MHz, CDCl₃): δ 7.80 (d, 1H); 6.91 (s, 1H); 6.86 (d, 1H); 4.39 (dd, 1H); 4.15 (dd, 1H); 3.43–3.37 (m, 1H); 2.93 (dd, 1H); 2.89 (dd, 1H); 2.42 (s, 3H)

ii) 1-[3-(4-Chlorophenoxy)-1-pyrrolidinyl]-3-(5-methyl-2-nitrophenoxy)-2-propanol A mixture of compound i) (1.05 g, 5.0 mmol) and 3-(4-chlorophenoxy)pyrrolidine (988 mg, 5.0 mmol) in ethanol (12 mL) was refluxed for 2h. The solvent was evaporated to give the crude product as an orange oil, which was used without further purification.

APCI-MS: m/z 407, 409 [MH⁺]

iii) 1-(2Amino-5-methylphenoxy)-3-[3-(4-chlorophenoxy)-1-pyrrolidinyl]-2-propanol To a stirred solution of compound ii) (2.1 g, 5.0 mmol) in ethanol (10 mL) tin(II) chloride dihydrate (5.6 g, 25 mmol) in 35% hydrochloric acid (6 mL) was added at 50° C. An exothermic reaction started and the temperature increased rapidly to 75° C. The mixture was maintained at 60° C. for 0.5 h. The cooled mixture was alkalized with 1M sodium hydroxide (180 mL) and extracted with ether, the organic phase washed with water, dried and evaporated to give the subtitle compound as a pale yellow oil (1.34 g, 71%).

NMR: Due to a mixture of two diastereomeric pairs integration will result in parts of protons.

¹H-NMR (400 MHz, CDCl₃): δ 7.23 (d, 2H); 6.77 (d, 2H); 6.67–6.65 (m, 1H); 6.64–6.63 (m, 1H); 4.83–4.76 (m, 1H); 4.14–4.06 (m, 1H); 4.01 (d, 2H); 3.71 (bs, 2H); 3.41 (bs, 1H); 3.10 (dd, 0.5H); 3.01–2.90 (m, 1.75H); 2.87–2.70 (m, 2.7H); 2.66–2.57 (m, 1.5H); 2.28 (h, 1H); 2.25 (s, 3H); 2.06–1.95 (m, 1H)

APCI-MS: 377, 379 [MH⁺]

iv) N-(2-{3-[3-(4-Chlorophenoxy)-1-pyrrolidinyl]-2-hydroxypropoxy}-4-methylphenyl)-1-pyrrolidinecarboxamide trifluoroacetate A solution of compound (iii) (75 mg, 0.2 mmol) and di(tert-butyl) tricarbonate (53 mg, 0.2 mmol) in DCM (3 mL) was stirred for 1 h at ambient temperature. Pyrrolidine (33 μL, 0.4 mmol) was added and the stirring continued for 1 h. The reaction was complete as determined by LCMS. TFA (1 mL) was added and the solution was left for 1 h. The volatile parts were evaporated and the crude product purified by preparative RP-HPLC using acetonitrile and water containing 0.1% TPA as mobile phase. The appropriate fraction was concentrated in vacuo and the residue lyophilized to give the title compound as a white amorphous solid (85 mg, 72%).

NMR: Due to a mixture of two diastereomeric pairs integration will result in parts of protons. Data are from the free base.

¹H-NMR (400 MHz, CDCl₃): δ 8.03 (dd, 1H); 7.24 (d, 2H); 6.94 (bs, 1H); 6.82–6.74 (m, 2H); 6.78 (d, 2H); 6.73–6.68 (m, 1H); 4.85–4.76 (m, 1H); 4.11–3.94 (m, 3H); 3.52–3.42 (m, 5.6H); 3.11 (dd, 0.5H); 3.05–2.92 (m, 0.45H) 2.95 (d, 1H); 2.87–2.72 (m, 2.5H); 2.62–2.52 (m, 1.4H); 2.37–2.21 (m, 0.7H); 2.29 (s, 3H); 2.08–1.90(m, 4.6H)

APCI-MS: m/z 474, 476 [MH⁺]

EXAMPLE 254

N-(2-{3-[3-(4-Chlorophenoxy)-1-pyrrolidinyl]-2-hydroxypropoxy}-4-hydroxyphenyl)acetamide trifluoroacetate To a stirred solution of the free base of compound Example 265 iii) following (128 mg, 0.29 mmol) in DCM (4 mL) under N₂ 1M boron tribromide in DCM (0.58 mL, 0.58 mmol) was added at ambient temperature. The heterogeneous mixture was stirred overnight and poured into methanol. After evaporation the crude product was purified by RP-HPLC using acetonitrile and water containing 0.1% TFA as mobile phase. The appropriate fraction was lyophilized to give the title compound as a white amorphous solid (113 mg, 73%).

APCI-MS: m/z 421, 423 [MH⁺]

EXAMPLE 255

N-[2-({(2S)-3-[4-(3,4-Dichlorophenoxy)-1-piperidinyl]-2-hydroxypropyl}oxy)-4-fluorophenyl] acetamide trifluoroacetic acid salt i) (2S)-2-[(5-Fluoro-2-nitrophenoxy)methyl]oxirane In a flask was added (R)-glycidol (0.994 g, 13.4 mmole) and triphenylphosphine (3.52 g, 13.4 mmole) and THF (20 ml, dried over molecular sieves), and 5-fluoro-2-nitrophenol (2.10 g, 13.4 mmole). The mixture was stirred until a homogeneous solution was obtained. The solution was cooled in an ice bath and diethylazodicarboxylate (DEAD, 2.11 ml, 13.4 mmole) was added dropwise over a few minutes. After completed addition, the flask was allowed to reach room temperature and stirred for an additional 2 hours. The solvent was removed in vaccuo and to the residue was added chloroform (5–10 ml). The precipitate (PPh₃O) was removed by filtration and the solid was washed with an additional amount of chloroform (5–10 ml). The filtrate was added to a flash column (SiO₂, Heptane:Ethyl acetate 4:1), and purified to give 2.02 g (71%) of the sub-title compound as a crystalline material after concentration of pure fractions.

¹H-NMR (400 MHz, CDCl₃) δ: 7.97 (1H, dd, J 9.3, 6.0 Hz); 6.86 (1H, dd, J 10.0, 2.5 Hz); 6.80–6.74 (1H, m); 4.44 (1H, dd, J 1 1.4, 2.6 Hz); 4.12 (1H, dd, J 11.2, 5.1 Hz); 3.44–3.38 (1H, m); 2.95 (1H, t, J 4.5 Hz); 2.90 (1H, dd, J 4.8, 2.6)

ii) (2S)-1-[4-(3,4-Dichlorophenoxy)-1-piperidinyl]-3-(5-fluoro-2-nitrophenoxy)-2-propanol In a vial was added 4-(3,4-dichlorophenoxy)-piperidine (0.123 g, 0.5 mmole) and the compound obtained in i) (0.106 g, 0.5 mmole) and ethanol (99.5%, 3 ml). The vial was sealed and the content was heated with stirring at 65° C. for 3 hours, and the reaction was monitored on LC-MS. The vial was allowed to cool and the solvent was evaporated, giving an oil, which was purified on silica (DCM to DCM:MeOH 99:1 to 98:2 to 97:3 as a stepwise gradient). Evaporation of pure fractions gave 0.22 g (96%) of the sub-title compound as an oil.

APCI-MS (m/z): 459.1 [M+H]

iii) N-[2-({(2S)-3-[4-(3,4-Dichlorophenoxy)-1-piperidinyl]-2-hydroxypropyl}oxy)-4-fluorophenyl]acetamide trifluoroacetic acid salt The compound obtained in ii) (0.22 g, 0.48 mmole) was dissolved in ethanol (99.5%, 7 ml) and heated with stirring to 60° C. A solution of SnCl₂×2H₂O (0.56 g, 5 equivalents) in concentrated hydrochloric acid (0.63 ml) was added and was stirred at 60° C. for 1 hour. The mixture was then allowed to cool. The solution was alkalized by the addition of excess 2M NaOH, and the solution was extracted with diethyl ether (3×50 ml). The combined ethereal solutions were washed with brine an evaporated. The obtained oil was dissolved in THF (8 ml), and water (8 ml) was added, followed by the addition of acetic anhydride (50□l, 0.52 mmole). The mixture was stirred at 40° C. for 15 minutes. The organic solvent was removed in vaccuo, and the residue was extracted with EtOAc (3×30 ml). The combined organic phases were washed with brine and were then concentrated in vaccuo. The residual oil was purified on preparative HPLC giving 55 g (20%, 98% purity) of the title compound as the trifluoro acetate, and as a white solid after lyophilization of pure fractions.

APCI-MS (m/z): 471.0, 472.0, 473.0 and 474.0 [M+H]

EXAMPLE 256

N-(2-(3-(4-Chloro-phenoxy)-pyrrolidin-1-yl)-2-hydroxy-propoxy)-4,6-difluoro-phenyl)-acetamide hydrochloride i) 3,5-Difluoro-6-nitrophenol To a stirred solution of 2,3,4-trifluoronitrobenzene (5 g, 28.23 mmol) in dry methanol (70 ml) was added a solution of sodium (0.68, 29.46) in dry methanol (30 ml). The solution was stirred until all starting material was consumed (~2 h). After concentration water was added and the solution was extracted with ether, dried over $Na_2SO_4$, filtered and concentrated to a yellow residue (4.65 g). To the solution of the yellow residue in dichloromethane (140 ml) was added boron tribromide (1M in dichloromethane, 40 ml) and stirred at room temperature overnight. Water was then added and the solution stirred for further 30 min. The organic phase was separated and the water phase was extracted with ether. The combined organic phase were dried over $Na_2SO_4$, filtered and concentrated in vacuo to give a brownish residue. The residue was taken up into ether and washed with 2M sodium hydroxide and water. The water and sodium hydroxide washings were combined and neutralized with 6M HCl and extracted with ether, dried over $Na_2SO_4$ and evaporated to give a yellow residue which was purified by flash chromatography on silica gel with EtOAc:Heptan; 1:2 as eluent to give the desired product 2 g, 11.42 mmol.

GC-MS: m/z 175(M+)

$^1$HNMR (400 MHz, $CD_3OD$) δ ppm, 6.63–6.68(1H, m), 6.60–6.67(1H, dt)

ii) 2-[(3,5-Difluoro-2-nitrophenoxy)methyl]oxirane

To a mixture of 3,5-difluoro-6-nitrophenol (100 mg, 0.571 mmol) and potassium carbonate (394 mg) in DMF (5 ml) was added epibromohydrin (80 mg, 0.582 mmol) and was stirred at 70° C. for 3 hr. Water and ethyl acetate were added, the organic phase separated, dried and concentrated. The resulting residue was purified by chromatography (ethyl acetate: heptan 1:3) to give the desired product as a solid 161 mg (0.696 mmol).

GC-MS: m/z 231 (M+)

iii) 1-[3-(4-Chlorophenoxy)-1-pyrrolidinyl]-3-(3,5-difluoro-2-nitrophenoxy)-2-propanol A solution of 3-(4-chlorophenoxy)pyrrolidine and 2-[(3,5-difluoro-2-nitrophenoxy)methyl]oxirane (50 mg, 0.21 mmol) in ethanol was refluxed for 3 hrs. The solvent was distilled off under reduced pressure and the resulting residue purified by silica gel column chromatography (dichloromethane/methanol 20:1) to give 45 mg (0.105 mmol) of the title compound as solid.

iv) N-(2-(3-(4-Chloro-phenoxy)-pyrrolidin-1-yl)-2-hydroxy-propoxy)-4,6-difluoro-phenyl)-acetamide hydrochloride Platinum oxide on carbon was added to a solution of 1-[3-(4-chlorophenoxy)-1-pyrrolidinyl]-3-(3,5-difluoro-2-nitrophenoxy)-2-propanol (40 mg, 0.0932 mmol) in ethanol and the mixture was hydrogenated for 4 hrs at 1 atm. The mixture was filtered through Celite and washed several times with warm ethanol and the combined filtrate were concentrated in vacuo. To the resulting yellow residue was taken up in dichloromethane and acetic anhydride was added to the solution. The solution was stirred at room temperature for 2 hrs then concentrated. Addition of 1.0M ethereal hydrogen chloride solution gave the title product as solid 20 mg APCI-MS: m/z 441 [$MH^+$]

EXAMPLE 257

N-[2-({(2S)-3-[(2S,4S)-4-(4-Chlorophenoxy)-2-methylpyrrolidinyl]-2-hydroxypropyl}oxy)-4-fluorophenyl]acetamide trifluoroacetic acid salt The title compound was prepared according to the procedure described in Example 260 following.

$^1$H-NMR (400 MHz, DMSO-$d_6$) δ: 9.89 (1H, bs); 9.05 (1H, s); 7.79 (1H, dd, J 8.8, 66 Hz); 7.37 (2H, d, J 9.6 Hz); 7.00–6.94 (3H, m); 6.75 (1H, dt, J 8.6, 2.6 Hz); 6.00 (1H, bs); 5.17–5.10 (1H, m); 4.32–4.20 (1H, m); 4.05 (1H, dd, J 10.1, 4.6 Hz); 3.97 (1H, J 9.9, 5.7 Hz); 3.78–3.50 (3H, m); 3.47 (1H, t, J 11.6 Hz); 3.17 (1H, t, J 13.3 Hz); 2.83 (1H, p, J 6.9 Hz); 2.07 (3H, s); 1.90–1.80 (1H, m); 1.42 (3H, d, J 6.4 Hz)

EXAMPLE 258

N-[2-({(2S)-3-[(3R)-3-(4-Chlorobenzyl)pyrrolidinyl]-2-hydroxypropyl}oxy)phenyl]acetamide hydrochloride Prepared by the method described in Example 251.

EXAMPLE 259

N-{2-[(2R)-(3-{(3S)-3-[(4-Chlorophenyl)oxy]-1-pyrrolidinyl}-2-hydroxypropyl)oxy]-4-fluorophenyl}acetamide APCI-MS: m/z 423.1 [M+]

EXAMPLE 260

N-[2-({(2S)-3-[(2R,4S)-4-(4-chlorophenoxy)-2-methylpyrrolidinyl]-2-hydroxypropyl}oxy)phenyl] acetamide trifluoroacetic acid salt i) 1-(tert-Butyl) 2-methyl (2S,4R)-4-hydroxy-1,2-pyrrolidinedicarboxylate In a flask was dissolved (2S,4R)-4-Hydroxy-proline hydrochloride (5.4 g, 30 mmole) in a mixture of THF (200 ml), water (170 ml) and NaOH (30 ml, 2 M in water, 60 mmole). To this emulsion was added di-tert-butyldicarbonate ($Boc_2O$, 6.54 g, 30 mmole), and the mixture was stirred vigorously for 1 hour. Ether (100 ml) was added and the phases were allowed to separate. The aqueous phase was extracted with an additional 100 ml of ether. The aqueous phase was discarded and the combined organic phases were washed with 1M HCl (aq.) and potassium carbonate (saturated, aq.) and brine. The extract was dried with $Na_2SO_4$ and was concentrated in vaccuo to give a residue, which was purified on silica (Heptane:EtOAc 5:1 to 3:1 to 1:1 stepwise gradient, spots visualized with $I_2$/MeOH). Evaporation of pure fractions were concentrated in vaccuo to give 4.2 g (57%) of the subtitle compound as a colorless oil.

$^1$H-NMR (400 MHz, $CDCl_3$) δ: 4.50 (1H, bs); 4.45–4.35 (1H, m); 3.74 (3H, s); 3.64 (1H, dd, J 11.7, 4.3 Hz); 3.59–3.42 (1H, m); 2.35–2.20 (1H, m); 2.14–2.03 (1H, m); 1.97 (1H, dd, J 23.3, 3.7 Hz); 1.44 (9H, d, J 18.9 Hz)

ii) 1-(tert-Butyl) 2-methyl (2S,4S)-4-(4-chlorophenoxy)-1,2-pyrrolidinedicarboxylate In a flask was dissolved the compound obtained in i) (2.54 g, 10.3 mmole), triphenylphosphine (2.71 g, 10.3 mmole) and 4-Chlorophenol (1.33 g, 10.3 mmole) in THF (50 ml, dried over molecular sieves) under magnetic stirring. The flask was cooled in an ice bath and, to this stirred solution was added diethylazodicarboxylate (DEAD, 1.8 g, 10.3 mmole) dropwise under a few minutes. The reaction was allowed to stand over night, allowing the ice to melt and the reaction to reach room temperature. The solvents were evaporated and the residue was treated with ether (30 ml), allowing the phosphine oxide to precipitate. The solid was removed by filtration and the filtrate concentrated in vaccuo. The residue was purified on silica (Heptane:EtOAc 8:1 to 6:1 to 3:1, stepwise gradient. Spots on TLC were visualized by Seebach's reagent). Concentration of pure fractions gave 2.51 g (68%) of the sub-title compound as a colorless viscous oil.

$^1$H-NMR (400 MHz, CDCl$_3$) δ: 7.26–7.20 (2H, m); 6.77–6.70 (2H, m); 4.86 (1H, bs); 4.55 (½H, dd, J 8.6, 2.6 Hz); 4.43 (½H, dd, J 7.6, 3.9 Hz); 3.84–3.60 (5H, m); 2.53–2.36 (2H, m); 1.47 (9H, d, J 18.2 Hz)

iii) tert-Butyl (2S,4S)-4-(4-chlorophenoxy)-2-(hydroxymethyl)-1-pyrrolidinecarboxylate In a flask was dissolved the compound obtained in ii) (0.951 g, 2.67 mmole) in THF (10 ml, dried over sieves). The solution was cooled in an ice bath and LiBH$_4$ (0.09 g, 4.07 mmole) was added. The mixture was stirred over night, allowing the ice to cool, and the solution to reach room temperature. The crude mixture was then partitioned between EtOAc (100 ml) and water (100 ml). The aqueous phase was discarded and the organic solution was washed with 0.5M HCl (aq.), NaHCO$_3$ (sat, aq) and brine. The solution was evaporated to give an oil which seem to be contaminated with inorganic salts. Dissolution in DCM and filtration through Celite® afforded 0.82 g (94%) of the sub-title compound as a colorless oil.

$^1$H-NMR (400 MHz, DMSO-d$_6$) δ: 7.33 (2H, d, J 9.5 Hz); 6.95 (2H, d, J 9.5); 4.96 (1H, bs); 4.71 (1H, bs); 3.84–3.55 (3H, m); 3.32 (2H, bs); 2.29–2.07 (2H, m); 1.41 (9H, s)

iv) tert-Butyl (2S,4S)-4-(4-chlorophenoxy)-2-{[(methylsulfonyl)oxy]methyl}-1-pyrrolidine carboxylate In a flask was dissolved the compound obtained in iii) (0.82 g, 2.5 mmole) in dichloromethane (10 ml, dried over molecular sieves). The flask was cooled on ice, and triethylamine (0.69 ml, 5.0 mmole) was added from a syringe. Methanesulfonylchloride (0.30 ml, 3.86 mmole) was added dropwise over a few minutes, and the obtained mixture was stirred over night, allowing the ice to melt. To the mixture was added DCM (60 ml), and the solution was washed with 1M HCl (aq), NaHCO$_3$ (sat, aq), and brine. The solution was evaporated giving 0.876 g (86%) of the sub-title compound as a yellow oil, which was used in the next step without any further purification.

$^1$H-NMR (400 MHz, DMSO-d6) δ: 7.35 (2H, d, J 9.4 Hz); 6.99 (2H, d, J 9.4 Hz); 5.07–5.01 (1H, m); 4.37 (1H, dd, J 8.9, 4.2 Hz); 4.20–4.05 (2H, m); 3.71 (1H, dd, J 11.8, 5.0 Hz); 3.32 (2H, s); 3.15 (3H, s); 2.07 (1H, d, J 14.4 Hz); 1.41 (9H, s)

v) tert-Butyl (2R,4S)-4-(4-chlorophenoxy)-2-methyl-1-pyrrolidinecarboxylate

In a flask was dissolved the compound obtained in iv) (0.876 g, 2.16 mmole) in THF (10 ml, dried over molecular sieves). The reaction mixture was kept under an inert atmosphere and was then cooled in an ice bath. LiB(Et)$_3$H (1M Lithium triethylborohydride in THF, 9 ml, 9 mmole) was added with a syringe over 15 minutes. The ice bath was removed and the mixture was stirred over night. The crude mixture was partitioned between EtOAc (100 ml) and water (100 ml). The aqueous phase was removed, and the organic phase was washed with 1M HCl (aq), NaHCO$_3$ (sat, aq), and brine. The solution was evaporated and the residue was purified on silica (Heptane:EtOAc 10:1 to 5:1 to 4:1 to 2:1 gradient. TLC spots were visualized by Seebach's reagent), giving 0.401 g (60%) of the sub-title compound as a colorless oil.

$^1$H-NMR (400 MHz, DMSO-d$_6$) δ: 7.33 (2H, d, J 8.7 Hz); 6.96 (2H, d, J 8.7 Hz); 5.00–4.94 (1H, m); 3.89 (1H, bs); 3.64 (1H, dd, J 12.5, 5.2 Hz); 3.38 (1H, d, J 12.2 Hz); 2.41–2.28 (1H, m); 1.79 (1H, d, J 13.7 Hz); 1.40 (9H, s); 1.23 (3H, d, J 6.6 Hz)

vi) (2R,4S)-4-(4-Chlorophenoxy)-2-methylpyrrolidine trifluoroacetic acid salt

In a flask was dissolved the compound obtained in v) (0.390 g, 1.25 mmole) in dichloromethane (DCM, 15 ml). To this solution was added TFA (trifluoroacetic acid, 6 ml) and the mixture was allowed to stand for 3 hours, after which the volatiles were removed in vaccuo. The residue was co-evaporated twice with DCM, giving the sub-title compound as an oil.

APCI-MS (m/z): 212 [M+H]

vii) N-[2-({(2S)-3-[(2R,4S)-4-(4-Chlorophenoxy)-2-methylpyrroldinyl]-2-hydroxypropyl}oxy)phenyl] acetamide trifluoroacetic acid salt The title compound was prepared according to the method outlined in Example 255 starting from the material obtained in vi) and (2S)-2-[(2-nitrophenoxy)methyl]oxirane. The compound was obtained in 25% yield.

$^1$H-NMR (400 MHz, DMSO-d$_6$) δ: 9.88 (1H, bs); 9.02 (1H, s); 7.89 (1H, d, J 7.7 Hz) 7.37 (2H, d, J 7.7 Hz); 7.09–6.88 (5H, m); 6.02 (1H, bs); 5.18–5.11 (1H, m); 4.34–4.22 (1H, m); 4.02 (1H, dd, J 10.2, 4.3 Hz); 3.94 (1H, dd, J 9.8, 5.7 Hz); 3.77–3.30 (4H, m); 3.19 (1H, t, J 10.7 Hz); 2.84 (1H, p, J 6.7 Hz); 2.09 (3H, s); 1.91–1.81 (1H, m); 1.43 (3H, d, J 6.4 Hz)

APCI-MS (m/z): 419.2 [M+H]

EXAMPLE 261

N-{2-[(2S)-(3-{(3R)-3-[(4-Chlorophenyl)oxy]-1-pyrrolidinyl}-2-hydroxypropyl)oxy]-4-fluorophenyl}acetamide APCI-MS: m/z 423.1 [M+]

EXAMPLE 262

N'-(2-{3-[3-(4-Chlorophenoxy)-1-pyrrolidinyl]-2-hydroxypropoxy}-4-methylphenyl)-N,N-trifluoroacetate The title compound was prepared by analogy to the methods described in Example 253 starting from compound iii) (75 mg, 0.2 mmol) and dimethyl amine (2M in THF, 200 µL, 0.4 mmol). The substance was obtained as a white amorphous solid (73 mg, 65%).

$^1$H-NMR (400 MHz, MeOH-d4): δ 7.54 (dd, 1H); 7.51 (d, 2H); 7.16 and 7.15 (d, 2H); 7.05 (bs, 1H); 6.96 (bd, 1H); 5.40–5.35 (m, 1H); 4.544.46 (m, 1H); 4.27 (d, 2H); 4.16–3.56 (m, 6H); 3.20 (bs, 6H); 2.84–2.59 (m, 1H); 2.59–2.44 (m, 1H); 2.50 (s, 3H).

APCI-MS: m/z 448, 450 [MH$^+$]

EXAMPLE 263

N-(2-{3-[3-(4-Chloroanilino)-1-pyrrolidinyl]-2-hydroxypropoxy}phenyl)acetamide i) tert-Butyl-3-hydroxy-1-pyrrolidinecarboxylate To a solution of 3-hydroxy-1-pyrrolidine (871 mg, 10 mmol) in THF (30 mL) was added di-(tert.butyl) dicarbonate (2.18 g, 10 mmol) in THF (2 mL) and the reaction mixture kept on stirring at room temperature for overnight. The solvent was removed in vacuo and the residue was purified by flash chromatography (0–2% MeOH in CHCl$_3$) to give the subtitled compound (1.7 g).

$^1$H-NMR (CDCl$_3$, 400 MHz): δ 4.45 (m, 1H); 3.55–3.25 (m, 4H); 2.18–1.85 (m, 3H); 1.45 (s, 9H).

APCI-MS: m/z 166 (M-Boc).

ii) tert-Butyl-2-oxo-1-pyrrolidinecarboxylate

Chromium (vi) oxide (800 mg, 8.0 mmol) was added to pyridine (1.6 mL) in CH$_2$Cl$_2$ (10 mL) and the resulting solution was stirred for 15 min at room temperature. A solution of is tert.butyl-3-hydroxy-1-pyrrolidinecarboxylate (374.5 mg, 2.0 mmol) in CH$_2$Cl$_2$ (5 mL) was added, immediately followed by acetic anhydride and the reaction mixture kept at room temperature for 15 min. After addition of ethyl acetate, decanted and filtered through a short column of silica gel. The filtrate was concentrated to give the subtitled product (193 mg) and was used directly in the next step.

ii) tert-Butyl-3-(4-chloroanilino)-1-pyrrolidinecarboxylate

Tert butyl-2-oxo-1-pyrrolidinecarboxylate (190 mg, 1.02 mmol), 4-chloroaniline (64 mg, 0.5 mmol) and acetic acid (184 mg) were mixed in dichloroethane (5 mL). Sodium triacetoxyborohydride (326.5 mg) was added and the reaction mixture kept on stirring at room temperature for overnight. After addition of aq. NaHCO$_3$ the reaction mixture was diluted by addition of ethyl acetate. Two layers were separated. The organic layer was dried over Na$_2$SO$_4$, filtered, concentrated. The residue was purified by flash chromatography (0–15% ethyl acetate in petroleum spirit, 40–60) to give the subtitled product (140 mg).

$^1$H-NMR (CDCl$_3$, 400 MHz): δ 7.18 (m, 2H); 6.50 (m, 2H); 3.99 (m, 1H); 3.70 (m, 2H); 3.46 (m, 2H); 3.20 (m, 1H); 2.18 (m, 1H); 1.87 (m, 1H); 1.45 (s, 9H).

APCI-MS: m/z 197 (M-Boc).

iv) N-(4-Chlorophenyl)-3-pyrrolidinamine (2×CF$_3$COOH)

To a solution of tert.butyl-3-(4-chloroanilino)-1-pyrrolidinecarboxylate (130 mg, 0.438 mmol) in CH$_2$Cl$_2$ (5 mL) was added CF$_3$COOH (1 mL). After 30 min the volatiles were removed in vacuo to give the subtitled product (186 mg) and was used directly in the next step.

v) N-(2-{3-[3-(4-Chloroanilino)-1-pyrrolidinyl]-2-hydroxypropoxy}phenyl)acetatamide A mixture of N-(4-chlorophenyl)-3-pyrrolidinamine (2×CF$_3$COOH), (186 mg, 0.438 mmol), N-[2-(2-oxiranylmethoxy)phenyl]acetamide (91 mg, 0.438 mmol) and K$_2$CO$_3$ (200 mg) in ethanol (6 mL) was kept on stirring at 65° C. for 2.5 h. The volatiles were removed in vacuo. The residue was partitioned between ethyl acetate and aq. NH$_4$Cl solution. The organic layer was washed with water, dried over Na$_2$SO$_4$, filtered and concentrated. The residue was purified by flash chromatography (0–3% MeOH in CHCl$_3$) to give the titled product (70 mg).

$^1$H-NMR (CDCl$_3$, 400 MHz): δ 8.35 (m, 1H); 8.21 (br.s, 1H); 7.12 (m, 2H); 7.01 (m, 2H); 6.92 (m, 1H); 6.48 (m, 2H); 4.13–3.92 (m, 4H); 3.84 (br. s, 1H); 2.99 (m, 2H); 2.87–2.30 (m, 6H); 2.18 (s, 3H); 1.66 (m, 1H).

APCI-MS: m/z 446 (MH$^+$).

EXAMPLE 264

N-{2-[(3-{3-[(4-Chlorophenyl)oxy]-1-pyrrolidinyl}-2-hydroxy-1-methylpropyl)oxy]phenyl}acetamide hydrochloride i) N-{2-[(1-Methyl-2-propenyl)oxy]phenyl}acetamide The compound (557 mg, 40%) was prepared from 3-chloro-1-butene (747 ml, 7.42 mmol) and 2-acetamidophenol (1.02 g, 6.75 mmol) analogously to that described in Example 8 i).

$^1$H-NMR (400 MHz, CDCl$_3$): δ 8.37 (m, 1H), 7.80 (bs, 1H), 6.94 (m, 3H), 5.93 (m, 1H), 5.25 (m, 2H), 4.84 (m, 1H), 2.21 (s, 3H), 1.49 (d, J 6.3 Hz, 3H).

ii) N-{2-[1-(2-Oxiranyl)ethoxy]phenyl}acetamide

The compound was prepared from N-{2-[(1-Methyl-2-propenyl)oxy]phenyl}acetamide (549 mg, 2.67 mmol) and m-chloroperbenzoic acid (80%, 923 mg, 4.28 mmol) analogously to that described in Example 8 (ii). Purification wag done on silica gel with petroleum ether/ethyl acetate 10/15 as eluent. This gave separation of the two diastereomeric pairs.

Diastereomer 1: (53 mg, 9%), Rf=0.27
Diastereomer 2: (406 mg, 69%), Rf=0.20

$^1$H-NMR (400 MHz, CDCl$_3$): δ 8.39 (m, 1H), 8.01 (bs, 1H), 7.00 (m, 3H), 3.98 (m, 1H), 3.24 (m, 1H), 2.94 (t, J 4.5 Hz, 1H), 2.71 (dd, J 2.6 Hz, J 4.5 Hz, 1H), 2.23 (s, 3H), 1.47 (d, J 6.3 Hz, 3H).

iii) N-{2-[(3-{3-[(4-Chlorophenyl)oxy]-1-pyrrolidinyl}-2-hydroxy-1-methylpropyl)oxy]phenyl}acetamide hydrochloride The title compound (230 mg, 100%) was prepared from N-[2-(1-oxiranylethoxy)phenyl]acetamide diasteromer 2 (123 mg, 0.557 mmol) and 3-(4-chlorophenoxy)pyrrolidine (100 mg, 0.506 mmol) analogously to that described in Example 1 (iii).

$^1$H-NMR (400 MHz, MeOD): δ 7.86 (m, 1H), 7.30 (m, 2H), 7.09 (m, 2H), 6.97 (m, 3H), 5.21 (m, 1H), 4.51 (m, 1H), 3.83–4.22 (m, 3H), 3.37–3.62 (m, 4H), 2.68 (m, 1H), 2.27 (m, ½H), 2.19 (m, 3H), 1.32 (m, 3H).

MS-APCI+: m/z 419 [MH$^+$]

EXAMPLE 265

N-(2-{3-[3-(4-Chlorophenoxy)-1-pyrrolidinyl]-2-hydroxypropoxy}-4-methoxyphenyl)acetamide hydrochloride i) 1-[3-(4-Chlorophenoxy)-1-pyrrolidinyl]-3-(5-methoxy-2-nitrophenoxy)-2-propanol The subtitle compound was prepared in analogy of Example 253 ii) from 2-[(5-methoxy-2-nitrophenoxy)methyl]oxirane (320 mg, 1.6 mmol) and 3-(4-chlorophenoxy)pyrrolidine (365 mg, 1.6 mmol). The crude product was obtained as a yellow oil (580 mg) and was used without further purification.

APCI-MS: m/z 423, 425 [MH$^+$]

ii) 1-(2-Amino-5-methoxyphenoxy)-3-[3-(4-chlorophenoxy)-1-pyrrolidinyl]-2-propanol The subtitle compound was prepared in analogy of Example 253 iii) from compound i) (290 mg, 0.7 mmol). The crude compound was obtained as a colourless oil (233 mg, 85%) and was used without further purification.

APCI-MS: m/z 393, 395 [MH$^+$]

iii) N-(2-{[3-3-(4-Chlorophenoxy)-1-pyrrolidinyl]-2-hydroxypropoxy}-4-methoxyphenyl)acetamide hydrochloride To a solution of compound (ii) (157 mg, 0.4 mmol) in pyridine (3 mL) acetic anhydride (1 mL) was added. The mixture was stirred for 1 h at ambient temperature. After evaporation the residue was dissolved in methanol (mL) and 1.5M sodium methoxide in methanol (1 mL) was added. The mixture was left overnight at ambient temperature. After evaporation the residue was taken up in ether and water. The free base of the title compound was obtained from the organic phase as a colourless oil (171 mg, 98%). The free base (43 mg) was dissolved in methanol (5 mL), acidified with 1M hydrochloric acid till pH<2, diluted with water (50 mL) and lyophilized. The title compound was obtained as a white amorphous solid (30 mg, 64%).

APCI-MS: m/z 435, 437 [MH$^+$]

EXAMPLE 266

N(2-[3-(4-Chloro-benzyloxy)-pyrrolidin-1-yl]-2-hydroxy-propoxy)-phenyl)-acetamide trifluoroacetic acid salt.

i) 3-(4-Chloro-benzyloxy)-pyrrolidine-1-carboxylic acid tert-butyl ester

A solution of tert-butyl 3-hydroxy-1-pyrrolidinecarboxylic acid (0.27 g, 1.44 mmol) in dry THF (4 mL) was added dropwise to a cold (0° C.), stirred suspension of sodium hydride (0.078 g, 2.17 mmol, ca. 50% suspension in oil) in THF (10 mL). After 30 min. a solution of 4-chlorobenzyl bromide (0.36 g, 1.74 mmol) in THF (2 mL) was added and the resulting suspension was stirred at R.T. overnight. The reaction mixture was partitioned between water and ethyl acetate. The aqueous phase was extracted with ethyl acetate and the combined organic phase was washed with saturated aqueous sodium chloride, dried and concentrated. The residue was subjected to flash chromatography (heptane-ethyl acetate, 6:1) to afford the subtitle compound 3-(4-Chloro-benzyloxy)-pyrrolidine-1-carboxylic acid tert-butyl ester as an oil (0.30 g, 66.8%).

$^1$H-NMR (CDCl$_3$): δ 7.30 (m, 4H), 4.49 (bs, 2H), 4.11 (m, 1H), 3.45 (m, 4H), 1.90–2.08 (m, 2H), 1.46 (s, 9H).

ii) 3-(4-Chloro-benzyloxy)-pyrrolidine

A solution of 3-(4-Chloro-benzyloxy)-pyrrolidine-1-carboxylic acid tert-butyl ester (0.28 g, 0.9 mmol) in aqueous 90% formic acid (7.5 mL) was stirred at (0° C.) for 30 min. then at room temperature overnight. The solvents were removed under reduced pressure and the residue was treated with saturated aqueous potassium carbonate and extracted twice with n-butanol. The combined organic extracts was concentrated and the residue was purified by flash chromatography (SiO$_2$, dichloromethane-methanol-ammonium hydroxide, 8:8:1 then 50:10:1) to afford the subtitle compound 3-(4-Chloro-benzyloxy)-pyrolidine (0.13 g, 70%).

$^1$H-NMR (DMSO-d$_6$): δ 7.32–7.41 (m, 4H), 4.42 (s, 2H), 4.02 (m, 1H), 3.18 (bs, 3H), 2.75–2.86 (m, 3H), 2.68 (m, 1H), 1.66–1.81 (m, 2H).

APCI-MS: m/z 212 [MH$^+$].

iii) N-(2-[3-(4-Chloro-benzyloxy)-pyrrolidin-1-yl]2-hydroxy-propoxy)-phenyl)-acetamide trifluoroacetic acid salt A solution of 3-(4-chloro-benzyloxy)-pyrrolidine (0.050 g, 0.24 mmol) and N-(2-oxiranylmethoxy-phenyl)-acetamide (0.049 g, 0.24 mmol) in absolute ethanol (3 mL) was heated in a closed vial at 70° C. for 2h. The product was purified by HPLC to afford the title compound (0.60 g, 47%).

$^1$H-NMR (CD$_3$OD): δ 7.85 (m, 1H), 7.35 (m, 4H), 7.12 (m, 1H), 7.02 (d, 1H, J=8 Hz), 6.96 (m, 1H), 4.56 (m, 2H), 4.39 (m, 2H), 4.05 (d, 2H, J 5.9 Hz), 3.85 (m, 2h), 3.48 (m, 4H), 2.10–2.55 (m, 5H).

APCI-MS: m/z 419 [MH$^+$] and 421 [MH+2$^+$].

EXAMPLE 267

N-(2-{3-[3-(4-Chloro-phenoxy)-pyrrolidin-1-yl]-2-hydroxy-2-methyl-propoxy}-phenyl)-acetamide The compound was prepared by a method analogous to that of Example 270 following.

APCI-MS: m/z 419 [MH$^+$]

EXAMPLE 268

N-(2-{(1S,2R,3S)*-3-[(3S-3-(3,4-Difluoro-phenoxy)-pyrrolidin-1-yl]-2-hydroxy-cyclopentyloxy}-5-chloro-phenyl)-acetamide (diastereomeric mixture)

Was prepared by analogy to Example 271 following from N-{5-chloro-2-[(1R,2S,5R)*-6-oxabicyclo[3.1.0]hex-2-yloxy]phenyl}acetamide (5.3 mg, 20 μmol) and (3S)-3-(3,4-difluoro-phenoxy)-pyrrolidine (4.0 mg, 20 μmol).

MS-APCI+: m/z 467 [M+].

EXAMPLE 269

N-[2-({(2R,3S)*-3-[(3)-3-(4-Chlorophenoxy) pyrrolidinyl-2-hydroxybutyl}oxy)-4-methylphenyl] acetamide (diastereomeric mixture)

Was prepared analogies to Example 271 following from N-(4-methyl-2-{[(2S,3R)*-3-methyloxiranyl] methoxy}phenyl)acetamide (4.7 mg, 20 μmol) and (3S)-3-(4-Chloro-phenoxy)-pyrrolidine (4.0 mg, 20 μmol).

MS-APCI+: m/z 433 [M+].

EXAMPLE 270

N-{2-[(3-{4-[(3,4-Dichlorophenyl)oxy]-1-piperidinyl}-2-hydroxy-2-methylpropyl)oxy]-4-fluorophenyl}acetamide hydrochloride i) N-[4-Fluoro-2-(2-methyl-allyloxy)-phenyl]-acetamide 3-Chloro-2-methylpropene (1.36 g, 15 mmol) was added to a mixture of 5-fluoro-2-nitro-phenol (1.57 g, 10 mmol), potassium carbonate (2.76 g, 20 mmol), tetrabutylammonium hydrogen sulfate (0.068 g, 0.2 mmol) and acetonitrile (30 ml), and the mixture was heated under reflux for 18 h. The cold reaction mixture was diluted with toluene and washed with 5% aqueous potassium carbonate, dried and evaporated. A part of the residue (0.631 g, 3 mmol), sodium dithionite (1.04 g, 6 mmol) in EtOH-THF-H$_2$O (2:1:1, 3 ml) was heated at 75° C. for 4 h. The mixture was portioned between dichloromethane and 15% aqueous potassium carbonate and the organic solution dried and concentrated. The obtained residue was diluted with methanol (1.5 ml) and reacted with acetic anhydride (1.5 ml) at 50° C. for 2 min and allowed to attend room temperature during 20 min, then pyridine (4 ml) was added and the solution heated again at 50° C. for 3 min, cold and concentrated. The material was purified by silica gel chromatography (light petroleum-ethyl acetate 2:1) to give 95 mg of the subtitle compound.

$^1$H-NMR (300 MHz, CDCl$_3$): δ 8.28 (dd, 1H,), 7.62 (bs, 1H), 6.70–6.60 (m, 2H), 5.07 (dd, 2H), 4.49 (s, 2H), 2.20 (s, 3H), 1.84 (s, 3H).

ii) N-(4-Fluoro-2-{[(2-methyl-2-oxiranyl)methyl] oxy}phenyl)acetamide

The subtitle compound was prepared from N-[4-fluoro-2-(2-methyl-allyloxy)-phenyl]-acetamide analogously as described in Example 8 ii).

$^1$H-NMR (300 MHz, CDCl$_3$): δ 8.31–8.26 (dd, 1H,), 7.79 (bs, 1H), 6.75–6.65 (m, 2H), 4.14 (d, 1H), 3.97 (d, 1H), 2.93 (d, 1H), 2.80 (d, 1H), 2.21 (s, 3H), 1.50 (s, 3H).

APCI-MS: m/z 240 [MH$^+$]

iii) N-{2-[(3-{4-[(3,4-Dichlorophenyl)oxy]-1-piperidinyl}-2-hydroxy-2-methylpropyl)oxy]-4-fluorophenyl}acetamide hydrochloride A solution of 4-(3,4-dichloro-phenoxy)-piperidine (36 mg, 0.146 mmol), N-(4-fluoro-2-{[(2-methyl-2-oxiranyl) methyl]oxy}phenyl)acetamide (35 g, 0.146 mmol) in EtOH (1 ml, 95%) was stirred for 2.5 hours at 77° C. in a sealed vial. The solvent was evaporated and the residue was purified on silica (dichloromethane-methanol, 15:1, containing 1% of NH$_4$OH (25%)) to give 45 mg of the corresponding free amine of the title compound.

$^1$H-NMR of the corresponding free amine of the title compound, (400 MHz, CDCl$_3$): δ 8.26–8.22 (dd, 1H), 7.89 (bs, 1H), 7.31 (d, 1H), 7.01 (d, 1H), 6.77–6.65 (m, 3H), 4.30 (m, 1H), 3.80 (dd, 2H), 2.93–2.81 (m, 2H), 2.67 (d, 1H), 2.63–2.51 (m, 2H), 2.45 (d, 1H), 2.19 (s, 3H), 1.96 (m, 2H), 1.83 (m, 2H), 1.62 (bs, 1H), 1.31 (s, 3H).

iv) N-{2-[(3-{4-[(3,4-Dichlorophenyl)oxy]-1-piperidinyl]-2-hydroxy-2-methylpropyl)oxy]-4-fluorophenyl}acetamide hydrochloride A solution of the free amine in methanol (10 ml) was acidified with HCl (conc., 0.020 ml) to pH 3 and concentrated. The residue was coevaporated three times with toluene to give the title hydrochloride compound as a white powder.

APCI-MS: m/z 485, 487 [MH$^+$]

EXAMPLE 271

N-(2-{(1S,2R,3S)*-3-[(3S)-3-(4-Chloro-phenoxy)-pyrrolidin-1-yl]-2-hydroxy-cyclopentyloxy}-4-fluoro-phenyl)-acetamide (diastereomeric mixture)

N-{4-fluoro-2-[(1R,2S,5R)*-6-oxabicyclo[3.1.0]hex-2-yloxy]phenyl}acetamide (5.0 mg, 20 µmol) and (3S)-3-(4-Chloro-phenoxy)-pyrrolidine (3.9 mg, 20 µmol) were dissolved in a 2M solution of LiClO$_4$ in acetonitrile (0.2 ml) and heated in a sealed tube to 100° C. Dilution by ethyl acetate, neutral aqueous workup and evaporation of the solvent gave a crude product which was used without further purification.

MS-APCI+: m/z 449 [M+].

EXAMPLE 272

N-(5-Chloro-2-(3-[3-(3,4-difluoro-phenoxy)-pyrrolidin-1-yl]-2-hydroxy-propoxy}-phenyl)-acetamide APCI-MS: m/z 441.1 [MH$^+$]

EXAMPLE 273

N-(5-Chloro-2-{3-[3-(4-fluoro-phenoxy)-pyrrolidin-1-yl]-2-hydroxy-propoxy}-phenyl)-acetamide APCI-MS: m/z 423.1 [MH$^+$]

EXAMPLE 274

N-(4-Cyano-2-{3-[4-(3,4-dichloroanilino)-1-piperidinyl]-2-hydroxypropoxy}phenyl)acetamide APCI-MS: m/z 477 [MH$^+$]

EXAMPLE 275

N-(4-Hydroxy-2-{(1S,2R,3S)*-3-[(3S)-3-(4-chloro-phenoxy)-pyrrolidin-1-yl]-2-hydroxy-cyclopentyloxy}-phenyl)-acetamide (disatereomeric mixture)

i) N-{4-methoxy-2-[(1R,2S,R)*-6-oxabicyclo[3.1.0]hex-2-yloxy]phenyl}acetamide (32 mg, 122 µmol) and (3S)-3-(4-Chloro-phenoxy)-pyrrolidine (24 mg, 122 µmol) were dissolved in a 2M solution of LiClO$_4$ in acetonitrile (1 ml) and heated in a sealed tube to 100° C. Dilution by ethylacetate, neutral aqueous workup and evaporation of the solvents gave 62 mg (110%) of the crude addition product which was reacted with bortribromide (1M in CH$_2$Cl$_2$, 0.37 mL, 371 µmol) in dichloromethane (1 mL) at room temperature over night. The reaction was quenched with methanol (1.0 mL) and all volatile components were evaporated. The remaining crude was subjected to a reversed phase TPLC giving 30 mg (54%) of the title compound as a diastereomeric mixture.

MS-APCI+: m/z 447.1 [MH+].

ii) Separation of the Diastereomers

The above under i) described diastereomeric mixture was subjected to chiral phase HPLC (stationary phase: Chiralpak AD; mobile phase: iso-hexane/iso-propanol/methanol/diethylamine=80:16:4:0.1) with the compound of Example 276 as the first and the compound of Example 277 as the second eluted stereoisomer. The assignment of the absolute configuration of the respective stereoisomer beneath is set by will and exchangeable.

EXAMPLE 276

N-(4-Hydroxy-2-{(1S,2R,3S)-3-[(3S)-3-(4-chloro-phenoxy)-pyrrolidin-1-yl]-2-hydroxy-cyclopentyloxy}-phenyl)-acetamide $^1$H-NMR (400 MHz, CDCl$_3$; OH-protons are neglected): δ 8.02 (1H, s), 7.49 (1H, d, J 8.4 Hz), 7.17 (2H, d, J 8.9 Hz), 6.71 (2H, d, J 8.8 Hz), 6.43 (1H, s), 6.34 (1H, d, J 7.2 Hz), 4.76 (1H, m), 4.39 (1H, m), 4.09 (1H, m), 3.10–2.95 (3H, m), 2.89 (1H, m), 2.77 (1H, m), 2.24 (1H, m), 2.08 (3H, s), 2.10–1.84 (3H, m), 1.75 (1H, m), 1.59 (1H, m).

MS-APCI+: m/z 447.1 [MH+].

$[\alpha]^{22}$+49.5 (CH$_2$C$_2$).

EXAMPLE 277

N-(4-Hydroxy-2-{(1R,2S,3R)-3-[3S-3-(4-chloro-phenoxy)-pyrrolidin-1-yl]-2-hydroxy-cyclopentyloxy}-phenyl)-acetamide $^1$H-NMR (400 MHz, CDCl$_3$; OH-protons are neglected): δ 7.75 (1H, s), 7.60 (1H, d, J 8.4 Hz), 7.19 (2H, d, J 8.3 Hz), 6.73 (2H, d, J 8.6 Hz), 6.57 (1H, s), 6.38 (1H, d, J 8.4 Hz), 4.77 (1H, m), 4.43 (1H, m), 4.21 (1H, m), 3.09–2.94 (3H, m), 2.79 (1H, m), 2.68 (1H, m), 2.28 (1H, m), 2.08 (3H, s), 2.05–1.90 (3H, m), 1.86 (1H, m), 1.53 (1H, m).

MS-APCI+: m/z 447.1 [MH+].

$[\alpha]^{22}$=−45.2 (CH$_2$C$_2$).

The diastereomers of Examples 278 and 279 were prepared by methods analogous to those used to prepare the compounds of Examples 221–230 and separated as described in Example 275 above. The absolute configuration of the respective isomers is assigned by will as mentioned above and therefore exchangeable.

EXAMPLE 278

N-[2-({(1S,2R,3S)-3-[(3S)-3-(4-Chlorophenoxy) pyrrolidinyl]-2-hydroxycyclopentyl}oxy)phenyl] acetamide First eluted isomer.

MS-APCI+: m/z 431.1 [MH+].

$[\alpha]^{22}$=+72.2 (CH$_2$C$_2$).

EXAMPLE 279

N-[2-({(1R,2S,3R)-3-[(3S)-3-(4-Chlorophenoxy) pyrrolidinyl]-2-hydroxycyclopentyl}oxy)phenyl] acetamide Second eluted isomer.

MS-APCI+: m/z 431.1 [MH+].

$[\alpha]^{22}$=−51.4 (CH$_2$C$_2$).

The diastereomers of Examples 280 and 249 were prepared by methods analogous to those used to prepare the compounds of Examples 221–230 and separated as described in Example 275 above. The compound of Example 280 is the first eluted isomer whilst the compound of Example 249 is the second eluted isomer. The absolute configuration of the respective isomers is assigned by will as mentioned above and therefore exchangeable.

EXAMPLE 280

N-[5-Chloro-2-({(1S,2R,3S)-3-[(3S)-3-(4-chlorophenoxy)pyrrolidinyl]-2-hydroxycyclopentyl}oxy)phenyl]acetamide MS-APCI+: m/z 464.9 [MH+].
$[\alpha]^{22}$=+53.0 (CH$_2$C$_2$).

EXAMPLE 281

N-{5-Chloro-2-[((1S,2R,3S)*-3-{[1-(4-chlorobenzyl)-4-piperidinyl]amino}-2-hydroxycyclopentyl)oxy]phenyl}acetamide (racemic mixture)

Was prepared by analogy to Example 271 from N-{5-chloro-2-[(1R,2S,5R)*-6-oxabicyclo[3.1.0]hex-2-yloxy]phenyl}acetamide (5.3 mg, 20 μmol) and 1-(4-chlorobenzyl)-4-piperidinamine (4.5 mg, 20 μmol).

MS-APCI+: m/z 492 [M+].

EXAMPLE 282

N-[2-({(2S)-3-[(3S)-3-(4-Chlorophenoxy)pyrrolidinyl]-2-hydroxypropyl}oxy)-4-hydroxyphenyl]acetamide i) (2S)-2-[(5-Methoxy-2-nitrophenoxy)methyl]oxirane The subtitle compound was prepared under Mitsunobu conditions from R-(+)-glycidole (198 mg, 1 mmol), 5-methoxy-2-nitrophenol (169 mg, 1 mmol), triphenylphosphine (263 mg, 1 mmol) and DEAD (157 μL, 1 mmol) using dry THF as solvent. The crude material was purified by flashchromatography on silica using mixtures of ethylacetate and heptane as mobile phase. The appropriate fractions were pooled to give impure product as white crystals (175 mg). The product was contaminated with reduced DEAD in molar ratio 1:1, which is equal to a yield of the desired product of 100 mg, 44%.

$^1$H-NMR (400 MHz, CDCl$_3$): δ 8.00 (d, 1H); 6.60 (d, 1H); 6.55 (dd, 1H); 6.4 (bs, 1H, red.DEAD); 4.41 (dd, 1H); 4.22 (q, 4H, red.DEAD); 4.13 (dd, 1H); 3.89 (s, 3H); 3.44–3.39 (m, 1H); 2.95 (dd, 1H); 2.92 (dd, 1H); 1.29 (t, 6H, red. DEAD)

APCI-MS: m/z 226 [MH$^+$]

ii) (2S)-1-[(3S)-3-(4-Chlorophenoxy)pyrrolidinyl]-3-(5-methoxy-2-nitrophenoxy)-2-propanol The subtitle compound was prepared by analogy to Example 1(ii) from (i) (169 mg, 0.43 mg) and (3S)-3-(4-chlorophenoxy)pyrrolidine (85 mg, 0.43 mmol). The product was obtained as a yellow oil and was used without further purification.

APCI-MS: m/z 423, 425 [MH$^+$]

iii) (2S)-1-(2-Amino-5-methoxyphenoxy)-3-[(3S)-3-(4-chlorophenoxy)pyrrolidinyl]-2-propanol The subtitle compound was prepared in analogy of Example 253 iii) from (ii) (0.43 mmol). The product obtained (colourless oil, 163 mg) was a mixture of the desired product and reduced DEAD in molar ratio 5:1. The substance was used as it was.

$^1$H-NMR (400 MHz, CDCl$_3$): δ 7.23 (d, 2H); 6.77 (d, 2H); 6.67 (d, 1H); 6.49 (d, 1H); 6.41 (bs, red.DEAD); 6.39 (dd, 1H); 4.83–4.77 (m, 1H); 4.22 (q, red.DEAD); 4.14–4.07 (m, 1H); 4.01 (d, 2H); 3.75 (s, 3H); 3.01–2.91 (m, 2H); 2.88–2.72 (m, 3H); 2.62 (dd, 1H); 2.29 (hex, 1H); 2.06–1.96 (m, 1H); 1.29 (t, red.DEAD)

APCI-MS: m/z 393, 395 [MH$^+$]

iv) N-[2-({(2S)-3-[(3S)-3-(4-Chlorophenoxy)pyrrolidinyl]-2-hydroxypropyl}oxy)-4-methoxyphenyl]acetamide To a solution of compound iii) (157 mg) in a mixture of acetonitrile (10 mL) and water (2 mL) acetic anhydride (1 mL) was added and the mixture was stirred at ambient temperature overnight. 1.5M sodiummethoxid in methanol (1 mL) was added and the stirring continued for 1 h. After evaporation the residue was taken up in ether and water. The subtitle product was obtained from the organic phase as a colourless oil (155 mg).

$^1$H-NMR (400 MHz, CDCl$_3$): δ 8.18 (d, 1H); 7.95 (bs, 1H); 7.24 (d, 2H); 6.78 (d, 2H); 6.56–6.52 (m, 2H); 4.85–4.78 (m, 1H); 4.22 (q, red.DEAD); 4.10–4.02 (m, 2H); 4.00–3.92 (m, 1H); 3.78 (s, 3H); 3.00–2.91 (m, 2H); 2.87–2.73 (m, 3H); 2.53 (dd, 1H); 2.36–2.25 (m, 1H); 2.17 (s, 3H); 2.07–1.99 (m, 1H); 1.29 (t, red.DEAD)

APCI-MS: m/z 435, 437 [MH$^+$]

v) N-[2-({(2S)-3-[(3S)-3-(4-Chlorophenoxy)pyrrolidinyl]-2-hydroxypropyl}oxy)-4-hydroxyphenyl]acetamide The title compound was prepared by analogy to Example 254 from iv) (150 mg). The product obtained after lyophilization was a white amorphous solid (101 mg, 57%).

$^1$H-NMR (400 MHz, CDCl$_3$+1 drop DMSO-d$_6$): δ 8.7 (bs, 1H); 8.34 (s, 1H); 8.73 (d, 1H); 7.18 (d, 2H); 6.73 (d, 2H); 6.40–6.31 (m, 2H); 4.99–4.93 (m, 1H) 4.4–1.9 (bm, 6H); 4.31–4.23 (m, 1H); 3.88–3.78 (m, 2H); 3.39–3.25 (m, 2H); 2.4–2.2 (m, 2H); 2.07 (s, 3H)

APCI-MS: m/z 421, 423 [MH$^+$]

THP-1 Chemotaxis Assay

Introduction

The assay measured the chemotactic response elicited by MIP-1α chemokine in the human monocytic cell line THP-1. The compounds of the Examples were evaluated by their ability to depress the chemotactic response to a standard concentration of MIP-1α chemokine.

Methods

Culture of THP-1 Cells

Cells were thawed rapidly at 37° C. from frozen aliquots and resuspended in a 25 cm flask containing 5 ml of RPMI-1640 medium supplemented with Glutamax and 10% heat inactivated fetal calf serum without antibiotics (RPMI+ 10% HIFCS). At day 3 the medium is discarded and replaced with fresh medium.

THP-1 cells are routinely cultured in RPMI-1640 medium supplemented with 10% heat inactivated fetal calf serum and glutamax but without antibiotics. Optimal growth of the cells requires that they are passaged every 3 days and that the minimum subculture density is 4×10+5 cells/ml.

Chemotaxis Assay

Cells were removed from the flask and washed by centrifugation in RPMI+10% HIFCS+glutamax. The cells were then resuspended at 2×10+7 cells/ml in fresh medium (RPMI+10% HIFCS+glutamax) to which was added calcein-AM (5 μl of stock solution to 1 ml to give a final concentration of 5×10$^{-6}$M). After gentle mixing the cells were incubated at 37° C. in a CO$_2$ incubator for 30 minutes. The cells were then diluted to 50 ml with medium and washed twice by centrifugation at 400×g. Labelled cells were then resuspended at a cell concentration of 1×10+7 cells/ml and incubated with an equal volume of MIP-1α antagonist (10$^{-10}$M to 10$^{-6}$M final concentration) for 30 minutes at 37° C. in a humidified CO$_2$ incubator.

Chemotaxis was performed using Neuroprobe 96-well chemotaxis plates employing 8 μm filters (cat no. 101-8).

Thirty microlitres of chemoattractant supplemented with various concentrations of antagonists or vehicle were added to the lower wells of the plate in triplicate. The filter was then carefully positioned on top and then 25 µl of cells preincubated with the corresponding concentration of antagonist or vehicle were added to the surface of the filter. The plate was then incubated for 2 hours at 37° C. in a humidified $CO_2$ incubator. The cells remaining on the surface were then removed by adsorption and the whole plate was centrifuged at 2000 rpm for 10 minutes. The filter was then removed and the cells that had migrated to the lower wells were quantified by the fluorescence of cell associated calcein-AM. Cell migration was then expressed in fluorescence units after subtraction of the reagent blank and values were standardized to % migration by comparing the fluorescence values with that of a known number of labelled cells. The effect of antagonists was calculated as % inhibition when the number of migrated cells were compared with vehicle.

What is claimed is:

1. A compound of formula:

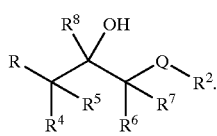

(I''')

wherein,

R represents a group:

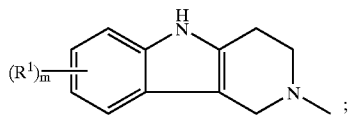

m is 0, 1, 2 or 3;

each $R^1$ independently represents halogen, cyano, nitro, carboxyl, hydroxyl, $C_3$–$C_6$ cycloalkyl, $C_1$–$C_6$ alkoxy, $C_1$–$C_6$ alkoxycarbonyl, $C_1$–$C_6$ haloalkyl, $C_1$–$C_6$ haloalkoxy, —$NR^9R^{10}$, $C_3$–$C_6$ cycloalkylamino, $C_1$–$C_6$ alkylthio, $C_1$–$C_6$ alkylcarbonyl, $C_1$–$C_6$ alkylcarbonylamino, sulphonamido, $C_1$–$C_6$ alkylsulphonyl, —$C(O)NR^{11}R^{12}$, —$NR^{13}C(O)$—$(NH)_p$ $R^{14}$, phenyl, or $C_1$–$C_6$ alkyl optionally substituted by carboxyl or $C_1$–$C_6$ alkoxycarbonyl;

p is 0 or 1;

Q represents an oxygen or sulphur atom or a group $CH_2$ or NH;

$R^2$ represents a group

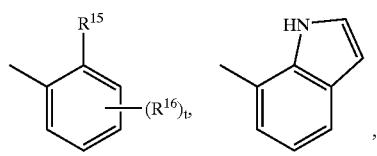

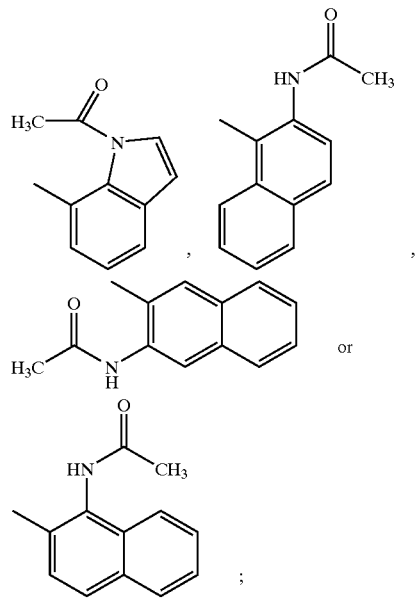

$R^4$, $R^5$, $R^6$ and $R^7$ each independently represent a hydrogen atom or a $C_1$–$C_6$ alkyl group, or $R^4$, $R^5$, $R^6$ and $R^7$ together represent a $C_1$–$C_4$ alkylene chain linking the two carbon atoms to which they are attached to form a 4- to 7-membered saturated carbocycle, or $R^5$, $R^6$ and $R^7$ each represent a hydrogen atom and $R^4$ and $R^8$ together with the carbon atoms to which they are attached form a 5- to 6-membered saturated carbocycle;

$R^8$ represents a hydrogen atom, a $C_1$–$C_6$ alkyl group or is linked to $R^4$ as defined above;

$R^9$ and $R^{10}$ each independently represent a hydrogen atom or a $C_1$–$C_6$ alkyl group, or $R^9$ and $R^{10}$ together with the nitrogen atom to which they are attached form a #4- to 7-membered saturated heterocycle;

$R^{11}$ and $R^{12}$ each independently represent a hydrogen atom or a $C_1$–$C_6$ alkyl group optionally substituted by $C_1$–$C_6$ alkoxycarbonyl;

$R^{13}$ represents a hydrogen atom or a $C_1$–$C_6$ alkyl group;

$R^{14}$ represents a hydrogen atom, or a $C_1$–$C_6$ alkyl group optionally substituted by carboxyl, $C_1$–$C_6$ alkoxy or $C_1$–$C_6$ alkoxycarbonyl;

$R^{15}$ represents carboxyl, $C_1$–$C_6$ alkylcarbonyl, $C_1$–$C_6$ alkoxycarbonyl, $C_1$–$C_6$ alkoxycarbonyl$C_1$–$C_6$ alkyl or a group —$NR^{17}R^{18}$, —$NHSO_2CH_3$, —$NHC(O)CH_3$, —$C(O)NR^{17}R^{18}$, —$NHC(O)NR^{17}R^{18}$, —$OC(O)NR^{17}R^{18}$, —$OCH_2C(O)NR^{17}R^{18}$, —$NHC(O)OR^{17}$ or —$OR^{17}$;

t is 0, 1, 2 or 3;

each $R^{16}$ independently represents halogen, cyano, nitro, carboxyl, hydroxyl, $C_3$–$C_6$ cycloalkyl, $C_1$–$C_6$ alkoxy, $C_1$–$C_6$ alkoxycarbonyl, $C_1$–$C_6$ haloalkyl, $C_1$–$C_6$ haloalkoxy, —$NR^{19}R^{20}$, $C_3$–$C_6$ cycloalkylamino, $C_1$–$C_6$ alkylthio, $C_1$–$C_6$ alkylcarbonyl, $C_1$–$C_6$ alkylcarbonylamino, sulphonamido (—$SO_2NH_2$), $C_1$–$C_6$ alkylsulphonyl, —$C(O)NR^{21}R^{22}$, —$NR^{23}C(O)(NH)_vR^{24}$, phenyl, or $C_1$–$C_6$ alkyl optional substituted by carboxyl or $C_1$–$C_6$ alkoxycarbonyl;

$R^{17}$ and $R^{18}$ each independently represent (i) a hydrogen atom, (ii) a 5- to 6-membered saturated or unsaturated ring which may have at least one heteroatom chosen from nitrogen, oxygen and sulphur, the ring being optionally substituted with at least one substituent selected from halogen, methyl and trifluoromethyl, or
(iii) a $C_1$–$C_6$ alkyl group optionally substituted by at least one substituent selected from halogen, trifluoromethyl, carboxyl, $C_1$–$C_6$ alkoxycarbonyl and a 5- to 6-membered saturated or unsaturated ring which may have at least one heteroatom chosen from nitrogen, oxygen and sulphur, the ring being optionally substituted with at least one substituent selected from halogen, methyl and trifluoromethyl, or $R^{17}$ and $R^{18}$ together with the nitrogen atom to which they are attached form a 4- to 7-membered saturated heterocycle;

$R^{17'}$ represents a hydrogen atom, or a $C_1$–$C_6$ alkyl group optionally substituted by carboxyl or $C_1$–$C_6$ alkoxycarbonyl;

$R^{17''}$ is defined as for $R^{17}$ above except that $R^{17''}$ does not represent a hydrogen atom;

$R^{19}$ and $R^{20}$ each independently represent a hydrogen atom or a $C_1$–$C_6$ alkyl group, or $R^{19}$ and $R^{20}$ together with the nitrogen atom to which they are attached form a 4- to 7-membered saturated heterocycle;

$R^{21}$ and $R^{22}$ each independently represent a hydrogen atom or a $C_1$–$C_6$ alkyl group optionally substituted by $C_1$–$C_6$ alkoxycarbonyl;

v is 0 or 1;

$R^{23}$ represents a hydrogen atom or a $C_1$–$C_6$, alkyl group; and $R^{24}$ represents a hydrogen atom, or a $C_1$–$C_6$ alkyl group optionally substituted by carboxyl, $C_1$–$C_6$ alkoxy or $C_1$–$C_6$ alkoxycarbonyl;

or a pharmaceutically acceptable salt or solvate thereof.

2. A compound according to claim 1, wherein Q represents an oxygen atom.

3. A compound according to claim 1, wherein $R^2$ represents a group

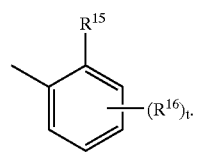

4. A compound according to claim 3, wherein $R^{15}$ represents $C_1$–$C_4$ alkoxy, $C_1$–$C_4$ alkylcarbonyl, $C_1$–$C_4$ alkoxycarbonyl$C_1$–$C_4$ alkyl, —NHC(O)CH$_3$, —C(O)NR$^{17}$R$^{18}$, —NHSO$_2$CH$_3$ or —NHC(O)NR$^{17}$R$^{18}$.

5. A compound according to claim 3, wherein each $R^{16}$ independently represents halogen, cyano, hydroxyl, $C_1$–$C_4$ alkoxy, $C_1$–$C_4$ alkoxycarbonyl, $C_1$–$C_4$ haloalkyl, $C_1$–$C_4$ alkylcarbonyl, phenyl or $C_1$–$C_4$ alkyl.

6. A compound of formula (I'''), or a pharmaceutically acceptable salt or solvate thereof, as defined in claim 1 being selected from:

N-{5-Chloro-2-[3-(8-chloro-1,3,4,5-tetrahydro-pyrido[4,3-b]indol-2-yl)-2-hydroxy-propoxy]-phenyl}-acetamide,
N-{3-Acetyl-2-[3-(8-chloro-1,3,4,5-tetrahydro-pyrido[4,3-b]indol-2-yl)-2-hydroxy-propoxyl]-5-methyl-phenyl}-acetamide,
N-{2-[3-(8-Chloro-1,3,4,5-tetrahydro-pyrido[4,3-b]indol-2-yl)-2-hydroxy-propoxy]-4-methyl-phenyl}-acetamide,
N-{2-[3-(8-Chloro-1,3,4,5-tetrahydro-pyrido[4,3-b]indol-2-yl)-2-hydroxy-propoxy]-5-fluoro-phenyl}-acetamide,
1-(8-Chloro-1,3,4,5-tetrahydro-pyrido[4,3-b]indol-2-yl)-3-(1H-indol-7-yloxy)-propan-2-ol,
1-{7-[3-(8-Chloro-1,3,4,5-tetrahydro-pyrido[4,3-b]indol-2-yl)-2-hydroxy-propoxy]-indol-1-yl}-ethanone,
N-{4-[3-(8-Chloro-1,3,4,5-tetrahydro-pyrido[4,3-b]indol-2-yl)-2-hydroxypropoxy]-biphenyl-3-yl}-acetamide,
N-{2-[3-(8-Chloro-1,3,4,5-tetrahydro-pyrido[4,3-b]indol-2-yl)-2-hydroxy-propoxy]-4-fluoro-phenyl}-acetamide,
N-{2-[3-(8-Chloro-1,3,4,5-tetrahydro-pyrido[4,3-b]indol-2-yl)-2-hydroxy-propoxy]-5-methyl-phenyl}-acetamide,
N-{2-[3-(8-Chloro-1,3,4,5-tetrahydro-pyrido[4,3-b]indol-2-yl)-2-hydroxy-propoxy]-phenyl}-acetamide,
N-{5-Chloro-2-[3-(8-fluoro-1,3,4,5-tetrahydro-pyrido[4,3-b]indol-2-yl)-2-hydroxy-propoxy]-phenyl}-acetamide,
N-{3-Acetyl-2-[3-(8-fluoro-1,3,4,5-tetrahydro-pyrido[4,3-b]indol-2-yl)-2-hydroxy-propoxy]-5-methyl-phenyl}-acetamide,
N-{2-[3-(8-Fluoro-1,3,4,5-tetrahydro-pyrido[4,3-b]indol-2-yl)-2-hydroxy-propoxy]4-methyl-phenyl}-acetamide,
N-{5-Fluoro-2-[3-(8-fluoro-1,3,4,5-tetrahydro-pyrido[4,3-b]indol-2-yl)-2-hydroxy-propoxy]-phenyl}-acetamide,
1-(8-Fluoro-1,3,4,5-tetrahydro-pyrido[4,3-b]indol-2-yl)-3-(1H-indol-7-yloxy)-propan-2-ol,
1-{7-[3-(8-Fluoro-1,3,4,5-tetrahydro-pyrido[4,3-b]indol-2-yl)-2-hydroxy-propoxy]-indol-1-yl}-ethanone,
N-{4-[3-(8-Fluoro-1,3,4,5-tetrahydro-pyrido[4,3-b]indol-2-yl)-2-hydroxy-propoxy]-biphenyl-3-yl}-acetamide,
N-{4-Fluoro-2-[3-(8-fluoro-1,3,4,5-tetrahydro-pyrido[4,3-b]indol-2-yl)-2-hydroxy-propoxy]-phenyl}-acetamide,
N-{2-[3-(8-Fluoro-1,3,4,5-tetrahydro-pyrido[4,3-b]indol-2-yl)-2-hydroxy-propoxy]-5-methyl-phenyl}-acetamide, and
N-{2-[3-(8-Fluoro-1,3,4,5-tetrahydro-pyrido[4,3-b]indol-2-yl)-2-hydroxy-propoxy]-phenyl}-acetamide.

7. A process for the preparation of a compound of formula (I''') as defined in claim 1 which comprises, (a) reacting a compound of formula:

wherein R is as defined in formula (I'''), with a compound of general formula:

wherein Q, $R^2$, $R^4$, $R^5$, $R^6$, $R^7$ and $R^8$ are as defined in formula (I'''); or (b) reacting a compound of formula:

wherein R, $R^4$, $R^5$, $R^6$, $R^7$ and $R^8$ are as defined in formula (I'''), with a compound of formula:

wherein $L^1$ represents a hydrogen atom or an activating group and Q and $R^2$ are as defined in formula (I''');

and optionally thereafter converting the compound of formula (I''') to a further compound of formula (I'''); and, if desired, forming a pharmaceutically acceptable salt or solvate of the compound of formula (I''').

8. A pharmaceutical composition comprising a compound of formula (I'''), or a pharmaceutically acceptable salt or solvate thereof, as claimed in claim 1 in association with a pharmaceutically acceptable adjuvant, diluent or carrier.

9. A process for the preparation of a pharmaceutical composition, the process comprising mixing a compound of formula (I'''), or a pharmaceutically acceptable salt or solvate thereof, as claimed in claim 1 with a pharmaceutically acceptable adjuvant, diluent or carrier.

10. A method of treating rheumatoid arthritis in a patient suffering from arthritis, which method comprises administering to the patient a therapeutically effective amount of a compound of formula (I'''), or a pharmaceutically acceptable salt or solvate thereof, as claimed in claim 1.

11. A method of treating asthma in a patient suffering from asthma, which method comprises administering to the patient a therapeutically effective amount of a compound of formula (I'''), or a pharmaceutically acceptable salt or solvate thereof, as claimed in claim 1.

12. A method of treating multiple sclerosis in a patient suffering from multiple sclerosis, which method comprises administering to the patient a therapeutically effective amount of a compound of formula (I'''), or a pharmaceutically acceptable salt or solvate thereof, as claimed in claim 1.

* * * * *